United States Patent [19]

Maki et al.

[11] Patent Number: 5,662,906

[45] Date of Patent: Sep. 2, 1997

[54] NON-A NON-B HEPATITIS-SPECIFIC ANTIGEN AND ITS USE IN HEPATITIS DIAGNOSIS

[75] Inventors: Noboru Maki; Kenjiro Yamaguchi, both of Iruma-gun; Ayumi Toyoshima, Kamifukuoka; Michinori Kohara, Tokorozawa, all of Japan

[73] Assignee: Tonen Corporation, Tokyo, Japan

[21] Appl. No.: 449,093

[22] Filed: May 24, 1995

Related U.S. Application Data

[62] Division of Ser. No. 81,072, Jun. 22, 1993, which is a continuation of Ser. No. 726,141, Jul. 8, 1991, abandoned.

[30] Foreign Application Priority Data

| Jul. 9, 1990 | [JP] | Japan | 2-180889 |
| Nov. 30, 1990 | [JP] | Japan | 2-339589 |
| Dec. 20, 1990 | [JP] | Japan | 2-413844 |

[51] Int. Cl.⁶ ............................................. A61K 39/29
[52] U.S. Cl. .............................. 424/184.1; 424/189.1; 424/228.1; 530/324; 530/350
[58] Field of Search ......................... 530/324, 350; 436/548; 435/252.33, 252.3; 536/22.1; 424/184.1, 185.1, 186.1, 189.1, 204.1, 228.1

[56] References Cited

FOREIGN PATENT DOCUMENTS

| 0318216 | 5/1989 | European Pat. Off. . |
| 0388232 | 9/1990 | European Pat. Off. . |
| 0 464 287 A1 | 12/1995 | European Pat. Off. . |

OTHER PUBLICATIONS

Kubo et al., *Nucleic Acids Research*, vol. 17, No. 24, 1989 pp. 10367–10372.

Okamoto et al., *Japan J. Exp. Med.*, vol. 60, No. 3, 1990, pp. 167–177.

Kato et al., *Proceedings of the National Academy of Sciences of the USA*, vol. 87, No. 24, Dec. 1990, pp. 9524–9528.

Kato et al., *Proc. Japan. Acad.*, vol. 65 Ser. 3, No. 1989, pp. 219–223.

Arima et al., *Gastroenterologica Japonica*, vol. 24, No. 5, 1989, pp. 540–544.

Ogata et al., *Proceedings of the National Academy of Sciences of the USA* vol. 88, No. 15, Apr. 1991 pp. 3392–3396.

Takamigawa et al., *Journal of Virology*, vol. 65, No. 3, Mar. 1991, pp. 1105–1113 Press (1979).

Choo et al., *Proceedings of the National Academy of Sciences of the USA*, vol. 88, Mar. 1991, pp. 2451–2455.

Arima et al., *Gastroenterologia Japonica*, vol. 24, No. 6, 1989, pp. 687–691.

Kubo et al. 1989. Nucleic Acids Research 17(24) 10367–10371.

Kato et al. 1989 Proc. Japan Acad. 65 SerB pp. 219–223.

*Primary Examiner*—James Ketter
*Assistant Examiner*—Irem Yucel
*Attorney, Agent, or Firm*—David G. Conlin; David S. Resnick

[57] ABSTRACT

This invention relates to a DNA fragment comprising a base sequence encoding a non-A non-B hepatitis-specific antigen polypeptide, said base sequence being obtained using genetic engineering techniques from non-A non-B hepatitis virus RNA which is isolated directly from blood plasma from non-A non-B hepatitis patients, to an expression vector and a transformant for use in the expression of the DNA fragment, to a single strand DNA sequence for PCR primer, and to use of said polypeptide and said single strand DNA sequence in the detection of the non-A non-B hepatitis virus. The recombinant polypeptide and the single strand DNA sequence for PCR primer make it possible to detect the non-A non-B hepatitis virus with extremely high accuracy.

2 Claims, 30 Drawing Sheets

Fig. 1a

```
         10         20         30         40         50         60
CGCAGTCATTCCAAGTGGCCCATCTACACGCTCCCACTGGCAGCGGGCAAGAGTACTAAAG
 GlnSerPheGlnValAlaHisLeuHisAlaProThrGlySerGlyLysSerThrLysVal 70         80         90        100        110        120
TGCCGGGCTGCATATGCCAGCCAAGGGTACAAGGTGCTCGTCCTCAACCCGTCCGTTGCCG
 ProAlaAlaTyrAlaSerGlnGlyTyrLysValLeuValLeuAsnProSerValAlaAla 130        140        150        160        170        180
CCACCTTAGGTTTTGGAGGCTATATGTCTAAGGCACATGGCACCCCAACATCAGAA
 ThrLeuGlyPheGlyAlaTyrMetSerLysAlaHisGlyThrAspProAsnIleArgThr 190        200        210        220        230        240
CTGGGGTAAGGACTATCACCACAGGCGCCCCATCACGTACTCCACTTACGGCAAGTTCC
 GlyValArgThrIleThrThrGlyAlaProIleThrTyrSerThrTyrGlyLysPheLeu 250        260        270        280        290        300
TTGCCGACGGGTGGTTGTTCTGGGGGGCGCTTATGACATCATAAATGTGTGATGAGTGCCACT
 AlaAspGlyGlyCysSerGlyGlyAlaTyrAspIleIleMetCysAspGluCysHisSer 310        320        330        340        350        360
CAACTGACGGCGACTTCCATCTTGGGCATCGGCACGGTCCTGGACCAAGCGGGAGACGGCTG
 ThrAspAlaThrSerIleLeuGlyIleGlyThrValLeuAspGlnAlaGluThrAlaGly
```

Fig. 1b

```
          370       380       390       400       410       420
GAGCACGGCTCGTCGTCGCTGCTCGCCACCGCTACCGCCTCCGGGATCGTCACCGTGCCACC
 AlaArgLeuValValLeuAlaThrAlaThrAlaThrProProGlySerValThrValProHisPro 430       440       450       460       470       480
CGAATATTGAGGAGGTGGCCCTGTCTAACACTGGAGAGATCCCCTTCTATGGCAAAGGCA
 AsnIleGluGluValAlaLeuSerAsnThrGlyGluIleProPheTyrGlyLysGlyIle 490       500       510       520       530       540
TCCCCATTGAAGTCATCAAGGGGGAAGGCATCTCATTTTCTGCCATTCCAAGAAGAAGT
 ProIleGluValIleLysGlyGlyArgHisLeuIlePheCysHisSerLysLysLysCys 550       560       570       580       590       600
GCGACAGTCGCCGCGAAGTTGTCAGGCCTCGGGATTAATGCTGTGGCATACTACCGGG
 AspGluLeuAlaAlaLysLeuSerGlyLeuGlyIleAsnAlaValAlaTyrTyrArgGly 610       620       630       640       650       660
GTCTTGATGTGTCCGTCATACCGACCAGCGGAGACGTCGTTGTCGTGGCAACAGACGCTC
 LeuAspValSerValIleProThrSerGlyAspValValValAlaThrAspAlaLeu 670       680       690       700       710       720
TAATGACGGGCTATACCGGCGATTTTGACTCAGTGATCGATCTGTAACACATGGTCACCC
 MetThrGlyTyrThrGlyAspPheAspSerValIleAspCysAsnThrCysValThrGln 730       740       750       760
AGACAGTCGACTTCAGTTGGACCCCACCTTCACCATTGAGAC
 ThrValAspPheSerLeuAspProThrPheThrIleGlu
```

Fig. 2

```
         10        20        30        40        50        60
CACGCCCGGTTTGCCCGTGTGTCAAGACCACCTGGAGTTCTGGGAAGCGGTCTTCACAGG
ThrProGlyLeuProValCysGlnAspHisLeuGluPheTrpGluAlaValPheThrGly 70        80        90       100       110       120
TCTCACGCACATTGATGCCCACTTCCTCTCCCAGACAAAGCAAGGAGGAGACAACTTCGC
LeuThrHisIleAspAlaHisPheLeuSerGlnThrLysGlnGlyGlyAspAsnPheAla 130       140       150       160       170       180
GTATCTAACGGCCTACCAGGCCACAGTGTGCGCTAGGGCAAAGGCCCCTCCTCCCTCGTG
TyrLeuThrAlaTyrGlnAlaThrValCysAlaArgAlaLysAlaProProProSerTrp 190       200       210       220       230       240
GGATGTGATGTGGAAATGTCTAGCTAGGCTGAAGCCTACACTAATTGGTCCTACCCCCCT
AspValMetTrpLysCysLeuAlaArgLeuLysProThrLeuIleGlyProThrProLeu 250       260       270       280       290       300
CCTGTACCGCTTGGGTGCCGTGACCAACGAGGTTACCCTGACGCACCCCGTGACGAAATA
LeuTyrArgLeuGlyAlaValThrAsnGluValThrLeuThrHisProValThrLysTyr 310       320       330       340       350       360
CATCGCCACGTGCATGCAAGCTGACCTCGAGATCATGACGAGCACATGGGTCCTAGCAGG
IleAlaThrCysMetGlnAlaAspLeuGluIleMetThrSerThrTrpValLeuAlaGly 370       380       390       400       410       420
GGGGGTGCTAGCCGCCGTGGCAGCTTACTGCCTGGCAACCGGCTGTGTTTCCATCATCGG
GlyValLeuAlaAlaValAlaAlaTyrCysLeuAlaThrGlyCysValSerIleIleGly 430       440       450       460       470       480
CCGCCTACACCTGAATGATCAAGTGGTTGTGACTCCTGACAAAGAAATCTTATATGAGGC
ArgLeuHisLeuAsnAspGlnValValValThrProAspLysGluIleLeuTyrGluAla 490       500       510       520       530       540
CTTTGATGAGATGGAAGAATGCGCCTCCAAAGCCGCCCTCATTGAGGAAGGGCAGCGGAT
PheAspGluMetGluGluCysAlaSerLysAlaAlaLeuIleGluGluGlyGlnArgMet 550       560       570       580       590       600
GGCGGAGATGCTCAAGTCTAAGATACAAGGCCTCCTACAACAGGCCACAAGACAGGCCCA
AlaGluMetLeuLysSerLysIleGlnGlyLeuLeuGlnGlnAlaThrArgGlnAlaGln

610
AGACATACAGCCAGC
AspIleGlnPro
```

Fig. 3a

```
         10         20         30         40         50         60
GTGAGGCGAGCCTCAGGAATGTTTGACAGTGTAGTGCTCTGTGAGTGCTATGACGCAGGGG
 GluArgAlaSerGlyMetPheAspSerValValLeuCysGluCysTyrAspAlaGlyAla 70         80         90        100        110        120
CTGCATGGTACGAGCTTACACCAGGGAGACCACCGTCAGGCTCAGAGGCTATTTCAACA
 AlaTrpTyrGluLeuThrProAlaGluThrThrValArgLeuArgAlaTyrPheAsnThr 130        140        150        160        170        180
CACCTGGCTTGCCTGTGTCAAGACCATCTTGAGTTCTGGGAGGCAGTTTTCACCGGCC
 ProGlyLeuProValCysGlnAspHisLeuPheTrpGluAlaValPheThrGlyLeu 190        200        210        220        230        240
TCACACACATAGATGCCCACTTCCTTTCCCAGACAAAGCAAGGGGACAATTTCGCAT
 ThrHisIleAspAlaHisPheLeuSerGlnThrLysGlnAlaGlyAspAsnPheAlaTyr 250        260        270        280        290        300
ACTTGACAGCCTACCAGGCTGTGCGCCAGAGCCAAAGCCCCTCCCCCGTCCTGGG
 LeuThrAlaTyrGlnAlaThrValCysAlaArgAlaAlaLysAlaProProSerTrpAsp 310        320        330        340        350        360
ACGTCATGTGGAAGTGCCTGACTCGGCTCAAGCCCACGCTTGTGCCCTACACCCCTTC
 ValMetTrpLysCysLeuThrArgLeuLysProThrLeuValAlaProThrProLeuLeu
```

Fig. 3b

```
           370       380       390       400       410       420
TGTACCGTTTAGGCTCTGTTACTAACGAGGTCACCCTCACACATCCTGTGACGAAATACA
  TyrArgLeuGlySerValThrAsnGluValThrLeuHisProValThrHisProValThrLysTyrIle 430       440       450       460       470       480
TCGCCACTTGCATGCAAGCTGACCTTGAGGTCATGACCAGCACGTGGGTCCTAGCTGGGG
  AlaThrCysMetGlnAlaAspLeuGluValMetThrSerThrTrpValLeuAlaGlyGly 490       500       510       520       530       540
GGGTCTTGGCAGCCGTCGCCGCGTATTGCCTGGCGACTGGGTGTGTCTCCATCATCGGCC
  ValLeuAlaAlaValAlaAlaAlaTyrCysLeuAlaThrGlyCysValSerIleIleGlyArg 550       560       570       580       590       600
GCTTGCACATCAATCAGCAGCCGTCGTTGCACCAGACAAGGAGGTCCTTTATGAGGCTT
  LeuHisIleAsnGlnArgAlaValAlaProAspLysGluValLeuTyrGluAlaPhe 610       620       630       640       650       660
TTGATGAGATGGAGGAGTGTGCCCTCTAAAGCGGCTCTCATTGAAGAGGGCACCGGATAG
  AspGluMetGluGluCysAlaSerLysAlaAlaLeuIleGluGluGlyGlnArgIleAla 670       680       690       700       710       720
CCGAGATGCTGAAGTCCAAGATCCAAGGCTTATTGCACCAAGCCCTCTAAACAGGCCCAGG
  GluMetLeuLysSerLysIleGlnGlyLeuLeuGlnGlnAlaSerLysGlnAlaGlnAsp 730       740       750       760       770
ACATACAACCCGCTGTGCAGCCTCATGCCCAAGGTGGAGCAATTCTGGC
  IleGlnProAlaValGlnProHisGlyProArgTrpSerAsnSerGly
```

Fig. 4

```
         10         20         30         40         50         60
CTGGTATGAACTTACGCCTGCTGAGACTACGGTGAGACTCCGGGCCTATTTCAACACGCC
 TrpTyrGluLeuThrProAlaGluThrThrValArgLeuArgAlaTyrPheAsnThrPro 70         80         90        100        110        120
CGGCCTGCCTGTGTGTCAAGACCACCTGGAATTCTGGGAGGCGGTCTTCACAGGTCTCAC
 GlyLeuProValCysGlnAspHisLeuGluPheTrpGluAlaValPheThrGlyLeuThr 130        140        150        160        170        180
ACACATCGATGCCCACTTCCTCTCCCAGACGAAGCAAGGAGGAGATAACTTTGCATATTT
 HisIleAspAlaHisPheLeuSerGlnThrLysGlnGlyGlyAspAsnPheAlaTyrLeu 190        200        210        220        230        240
AACAGCCTACCAGGCCACAGTCTGCGCTAGGGCAAAGGCTCCCCCTCCTTCGTGGGACGT
 ThrAlaTyrGlnAlaThrValCysAlaArgAlaLysAlaProProProSerTrpAspVal 250        260        270        280        290        300
GATGTGGAAGTGTTTGATTAGGCTCAAACCTACACTGACTGGTCCTACCCCCTCCTGTA
 MetTrpLysCysLeuIleArgLeuLysProThrLeuThrGlyProThrProLeuLeuTyr 310        320        330        340        350        360
CCGCTTGGGTGCCGTGACCAACGAGGTTACCCTGACTCACCCCATGACGAAATATATCGC
 ArgLeuGlyAlaValThrAsnGluValThrLeuThrHisProMetThrLysTyrIleAla 370        380        390        400        410        420
CACTTGTATGCAAGCTGATCTTGAGATCATGACAAGCACATGGGTCTTGGCGGGGGGGGT
 ThrCysMetGlnAlaAspLeuGluIleMetThrSerThrTrpValLeuAlaGlyGlyVal 430        440        450        460        470        480
GCTAGCCGCTGTGGCAGCTTACTGCCTAGCGACCGGCTGCATTTCCATCATTGGCCGCCT
 LeuAlaAlaValAlaAlaTyrCysLeuAlaThrGlyCysIleSerIleIleGlyArgLeu 490        500        510        520        530        540
TCACCTGAATGATCGGGTGGTCGTGACCCCTGATAAGGAAATTTTATATGAGGCCTTTGA
 HisLeuAsnAspArgValValValThrProAspLysGluIleLeuTyrGluAlaPheAsp 550        560        570        580        590        600
TGAGATGGAAGAGTGCGCCTCCAAAGCCGCCCTCATTGAGGAAGGGCAGCGGATGGCGGA
 GluMetGluGluCysAlaSerLysAlaAlaLeuIleGluGluGlyGlnArgMetAlaGlu 610        620        630
GATGCTGAAGTCTAAAATACAAGGCCTCTT
 MetLeuLysSerLysIleGlnGlyLeu
```

Fig. 5a

```
          10         20         30         40         50         60
GGGATCAACCCTAACATCAGGACCGGAGTACGGACCGTGACCACCGGGACTCCATCACC
GlyIleAsnProAsnIleArgThrGlyValArgThrValThrGlyAspSerIleThr 70         80         90        100        110        120
TACTCCACTTATGGCAAGTTTATCGCAGATGGAGGTTGCCACGTGGTGCCTATGACGTC
TyrSerThrTyrGlyLysPheIleAlaAspGlyGlyCysAlaArgGlyAlaTyrAspVal 130        140        150        160        170        180
ATCATATGCGACGAATGCCATTCAGTGGACGCTACTACCATCCTTGGCATTGGAACAGTC
IleIleCysAspGluCysHisSerValAspAlaThrThrIleLeuGlyIleGlyThrVal 190        200        210        220        230        240
CTTGACCAGGCTGAGACCCAGGCTGCCAGGCTAGTGGTTTTAGCCACACAGCCACCGCCACCC
LeuAspGlnAlaGluThrAlaGlyAlaArgLeuValValLeuAlaThrAlaThrProPro 250        260        270        280        290        300
GGTACGGTAACAACTCCCCACGCTAACATAGAGGAGGTGGCCCTTGGTCACGAAGGCGAG
GlyThrValThrThrProHisAlaAsnIleGluGluValAlaLeuGlyHisGluGlyGlu 310        320        330        340        350        360
ATTCCTTTTATGGCAAGGCTATTCCCTAGCTTTCATCAAGGGGGCAGACACCTAATT
IleProPheTyrGlyLysAlaIleProLeuAlaPheIleLysGlyGlyArgHisLeuIle
```

Fig. 5b

```
           370       380       390       400       410       420
TTTTGCCATTCAAAGAAGAAGTGCAAGAGCTCGGACGAGCAGCCCTTCGGGGCATGGGTATC
Phe Cys His Ser Lys Lys Cys Asp Glu Leu Ala Ala Leu Arg Gly Met Gly Ile 430       440       450       460       470       480
AATGCCGTTGCCTACTACAGGGGTCTCGACGTCTCCGTTATACCAACTCAAGGAGACGTG
Asn Ala Val Ala Tyr Tyr Arg Gly Leu Asp Val Ser Val Ile Pro Thr Gln Gly Asp Val 490       500       510       520       530       540
GTGGTTGTCGCCACCGATGCCCTAATGACTGGATACACCGGTGACTTTGACTCTGTCATC
Val Val Val Ala Thr Asp Ala Leu Met Thr Gly Tyr Thr Gly Asp Phe Asp Ser Val Ile 550       560       570       580       590       600
GACTGCAACGTTGCACTCAGATTGTTGACTTTAGCCTAGACCCAACTTTTACCATC
Asp Cys Asn Val Ala Val Thr Arg Gln Ile Ile Val Asp Phe Ser Leu Asp Pro Thr Phe Phe Thr Ile 610       620       630       640       650       660
ACCACTCAAACCGTCCCCTCAGGAGGCTGTCTCCCGTAGTCAACGTAGTAGCGGAGAACTGGG
Thr Thr Gln Thr Val Pro Gln Gly Cys Leu Pro Val Val Asn Val Val Ser Arg Arg Gly Arg Thr Gly 670       680       690       700       710       720
AGGGGGCGACTGGGACTTACAGGTATGTCTCCTCAGGCGAGAGGCCGTCTGGATGTTC
Arg Gly Arg Leu Gly Thr Tyr Arg Tyr Val Ser Ser Gly Glu Arg Pro Ser Gly Met Phe 730       740       750       760       770       780
GACAGGCGTAGTACTCTGCGAGTGCTATGATGCCGGGCAGCCTGGTACGAGCTTACACCT
Asp Ser Val Val Leu Cys Glu Cys Tyr Asp Ala Gly Ala Ala Trp Tyr Glu Leu Thr Pro
```

Fig. 5c

```
        790       800       810       820       830       840
GCTGAGACCACAGTGAGACTCCGGGCTTATTTCAACACGCCCGGTTTGCCCGTGTGTCAA
AlaGluThrThrValArgLeuArgAlaTyrPheAsnThrProGlyLeuProValCysGln 850       860       870       880       890       900
GACCACCTGGAGTTCTGGGAAGCGGTCTTCACAGGTCTCACGCACATTGATGCCCACTTC
AspHisLeuGluPheTrpGluAlaValPheThrGlyLeuThrHisIleAspAlaHisPhe 910       920       930       940       950       960
CTCTCCCAGACAAAGCAAGGAGGAGACAACTTCGCGTATCTAACGGCCTACCAGGCCACA
LeuSerGlnThrLysGlnGlyGlyAspAsnPheAlaTyrLeuThrAlaTyrGlnAlaThr 970       980       990      1000      1010      1020
GTGTGCGCTAGGGCAAAGGCCCCTCCTCCCTCGTGGGATGTGATGTGGAAATGTCTAGCT
ValCysAlaArgAlaLysAlaProProProSerTrpAspValMetTrpLysCysLeuAla 1030      1040      1050      1060      1070      1080
AGGCTGAAGCCTACACTAATTGGTCCTACCCCCCTCCTGTACCGCTTGGGTGCCGTGACC
ArgLeuLysProThrLeuIleGlyProThrProLeuLeuTyrArgLeuGlyAlaValThr 1090      1100      1110      1120      1130      1140
AACGAGGTTACCCTGACGCACCCCGTGACGAAATACATCGCCACGTGCATGCAAGTGAAC
AsnGluValThrLeuThrHisProValThrLysTyrIleAlaThrCysMetGlnValAsn 1150      1160      1170      1180      1190      1200
CTCGAGATCATGACGAGCACATGGGTCCTAGCAGGGGGGGTGCTAGCCGCCGTGGCAGCT
LeuGluIleMetThrSerThrTrpValLeuAlaGlyGlyValLeuAlaAlaValAlaAla 1210      1220      1230      1240      1250      1260
TACTGCCTGGCAACCGGCTGTGTTTCCATCATCGGCCGCCTACACCTGAATGATCAAGTG
TyrCysLeuAlaThrGlyCysValSerIleIleGlyArgLeuHisLeuAsnAspGlnVal 1270      1280      1290      1300      1310      1320
GTTGTGACTCCTGACAAAGAAATCTTATATGAGGCCTTTGATGAGATGGAAGAATGCGCC
ValValThrProAspLysGluIleLeuTyrGluAlaPheAspGluMetGluGluCysAla 1330      1340      1350      1360      1370      1380
TCCAAAGCCGCCCTCATTGAGGAAGGGCAGCGGATGGCGGAGATGCTCAAGTCTAAGATA
SerLysAlaAlaLeuIleGluGluGlyGlnArgMetAlaGluMetLeuLysSerLysIle 1390      1400      1410      1420
CAAGGCCTCCTACAACAGGCCACAAGACAGGCCCAAGACATACAGC
GlnGlyLeuLeuGlnGlnAlaThrArgGlnAlaGlnAspIleGln
```

Fig. 6a

```
         10         20         30         40         50         60
CGCAGACATTCCAAGTGGCCCATCTGCAGCTCCCACTGGTAGGGCAAGAGCACTAAGG
GlnThrPheGlnValAlaHisLeuHisAlaProThrGlySerGlyLysSerThrLysVal 70         80         90        100        110        120
TGCCGGCTGCATATGCGGGCCCAAGGGTACAAGGTACTCGTCCTGAACCCGTCCGTTGCCG
ProAlaAlaTyrAlaAlaAlaGlnGlyTyrLysValLeuValLeuAsnProSerValAlaAla 130        140        150        160        170        180
CCACTTTAGCCTTTGGGGCGTACATGTCTAAGGCACATGGTGTCGACCCTAACATCAGAA
ThrLeuAlaPheGlyAlaTyrMetSerLysAlaHisGlyValAspProAsnIleArgThr 190        200        210        220        230        240
CTGGGGTGAGGACCATCACCACGGGCCGCTCCCATCACGTACTCCACCTATGGTAAGTTCC
GlyValArgThrIleThrThrGlyAlaProIleThrTyrSerThrTyrGlyLysPheLeu 250        260        270        280        290        300
TTGCCGACGGTTGCTCTGGGGGCGCCTATGACATCATAATATGTGATGAGTGCCACT
AlaAspGlyGlyCysSerGlyGlyAlaTyrAspIleIleIleCysAspGluCysHisSer 310        320        330        340        350        360
CAACTGACTCGACATCCATCTTGGGCATCGGCACAGTCCTGACCAAGCGGAGACGGCTG
ThrAspSerThrSerIleLeuGlyIleGlyThrValLeuAspGlnAlaGluThrAlaGly
```

Fig. 6b

```
               370       380       390       400       410       420
         GAGCGCGGCTCGTCGTGCTCGCTACCGCTACGCCTCCGGGATCGGTCACCGTGCCACATC
          AlaArgLeuValValLeuAlaThrAlaThrProProGlySerValThrValProHisPro 430       440       450       460       470       480
         CCAATATCGAGGAGGTGGCCCTGTCCACCACTGGAGAGATTCCCTTCTACGGCAAAGCTA
          AsnIleGluGluValAlaLeuSerThrThrGlyGluIleProPheTyrGlyLysAlaIle 490       500       510       520       530       540
         TCCCCATCGAGACAATCAAGGGGGGGAGGCATCTCATCTTCTGCCGTTCCAAGAAGAAGT
          ProIleGluThrIleLysGlyGlyArgHisLeuIlePheCysArgSerLysLysLysCys 550       560       570       580       590       600
         GTGACGAGCTCGCTGGAAAGCTGTCAGCCCTCGGAATCAACGCTGTAGCGTACTACCGGG
          AspGluLeuAlaGlyLysLeuSerAlaLeuGlyIleAsnAlaValAlaTyrTyrArgGly 610       620       630       640       650       660
         GTCTTGATGTATCCGTCATACCGACCAGCGGAGACGTCGTTGTCGTGGCAACAGACGCTC
          LeuAspValSerValIleProThrSerGlyAspValValValAlaThrAspAlaLeu 670       680       690       700       710       720
         TAATGACGGGCTACACCGGTGACTTTGATTCAGTGATCGACTGCAATACATGTGTCACCC
          MetThrGlyTyrThrGlyAspPheAspSerValIleAspCysAsnThrCysValThrGln 730       740       750       760       770       780
         AGACAGTCGACTTCAGCTTGGACCCTACCTTCACCATTGAGACGACGACCGTGCCTCAAG
          ThrValAspPheSerLeuAspProThrPheThrIleGluThrThrThrValProGlnAsp 790       800       810       820       830       840
         ACGCGGTGTCACGCTCGCAGCGGCGAGGCAGAACTGGTAGGGGTAGAGGGGGCATATACA
          AlaValSerArgSerGlnArgArgGlyArgThrGlyArgGlyArgGlyGlyIleTyrArg

850
         GGTTTGTGACTCCAG
          PheValThrPro
```

Fig. 7

```
         10        20        30        40        50        60
GACGAGCTCGCCGCAAAGCTGTCAGGCCTCGGAGTCAATGCTGTGGCATACTACCGGGGT
AspGluLeuAlaAlaLysLeuSerGlyLeuGlyValAsnAlaValAlaTyrTyrArgGly 70        80        90       100       110       120
CTCGATGTGTCTGTCATACCGACGAGCGGGGACGTCGTTGTTGTGGCAACAGACGCTCTA
LeuAspValSerValIleProThrSerGlyAspValValValValAlaThrAspAlaLeu 130       140       150       160       170       180
ATGACGGGCTATACCGGCGACTTTGACTCGGTGATCGACTGCAATACATGTGTCACCCAA
MetThrGlyTyrThrGlyAspPheAspSerValIleAspCysAsnThrCysValThrGln 190       200       210       220       230       240
ACAGTCGATTTCAGCTTGGACCCTACTTTCACCATTGAGACGACGACCGTGCCCCAAGAC
ThrValAspPheSerLeuAspProThrPheThrIleGluThrThrThrValProGlnAsp 250       260       270       280       290       300
GCGGTGTCGCGCTCGCAGCGGCGAGGCAGGACTGGTAGGGGCAGGGTGGGCATATACAGG
AlaValSerArgSerGlnArgArgGlyArgThrGlyArgGlyArgValGlyIleTyrArg

310
TTTGTGACTCCCGAG
PheValThrProGlu
```

Fig.8a

```
          10        20        30        40        50        60
GTGATGAGCTCGCCGCAAAGCTCTCAAGCCTCGGACTCAACGCTGTAGCATATTACCGGG
  AspGluLeuAlaAlaLysLeuSerSerLeuGlyLeuAsnAlaValAlaTyrTyrArgGly 70        80        90       100       110       120
GTCTTGATGTGTCCGTCATACCGACTAGTGGAGACGTCGTTGTCGTGGCAACAGACGCTC
  LeuAspValSerValIleProThrSerGlyAspValValValValAlaThrAspAlaLeu 130       140       150       160       170       180
TAATGACGGGCTATACCGGCGACTTTGACTCAGTGATCGACTGTAACACATGTGTCACCC
  MetThrGlyTyrThrGlyAspPheAspSerValIleAspCysAsnThrCysValThrGln 190       200       210       220       230       240
AGACAGTTGATTTCAGCTTGGATCCAACCTTCACCATTGAGACGACGACCGTGCCTCAAG
  ThrValAspPheSerLeuAspProThrPheThrIleGluThrThrThrValProGlnAsp 250       260       270       280       290       300
ACGCGGTGTCGCGCTCGCAGCGGCGAGGTAGGACTGGCAGGGGCAGGGGCGGCATCTATA
  AlaValSerArgSerGlnArgArgGlyArgThrGlyArgGlyArgGlyGlyIleTyrArg 310       320       330       340       350       360
GGTTTGTGACTCCAGGAGAACGGCCCTCGGGCATGTTCGATTCCTCGGTCCTGTGTGAGT
  PheValThrProGlyGluArgProSerGlyMetPheAspSerSerValLeuCysGluCys 370       380       390       400       410       420
GTTATGACGCGGGCTGTGCTTGGTATGAGCTCACGCCCGCCGAGACCACGGTTAGGTTGC
  TyrAspAlaGlyCysAlaTrpTyrGluLeuThrProAlaGluThrThrValArgLeuArg 430       440       450       460       470       480
GGGCTTACCTAAATACACCAGGGTTGCCCGTCTGCCAGGACCATCTGGAGTTCTGGGAGG
  AlaTyrLeuAsnThrProGlyLeuProValCysGlnAspHisLeuGluPheTrpGluGly 490       500       510       520       530       540
GCGTCTTCACAGGCCTCACCCACATAGATGCCCATTTCTTGTCTCAGACTAAGCAGGCAG
  ValPheThrGlyLeuThrHisIleAspAlaHisPheLeuSerGlnThrLysGlnAlaGly
```

Fig. 8b

```
       550        560        570        580        590        600
GAGACAACTTTCCCTACCTGGTGGCATACCAAGCTACAGTGTGCGCCAGGGCTCAGGCTC
  AspAsnPheProTyrLeuValAlaTyrGlnAlaThrValCysAlaArgAlaGlnAlaPro 610        620        630        640        650        660
CACCTCCATCGTGGGACCAAATGTGGAAGTGTCTCATACGGCTGAAACCTACGCTGCACG
  ProProSerTrpAspGlnMetTrpLysCysLeuIleArgLeuLysProThrLeuHisGly 670        680        690        700        710        720
GGCCAACACCCCTGCTGTATAGGCTAGGAGCCGTCCAAAATGAGGTCACCCTCACACACC
  ProThrProLeuLeuTyrArgLeuGlyAlaValGlnAsnGluValThrLeuThrHisPro 730        740        750        760        770        780
CCATAACCAAATTCATCATGGCATGCATGTCGGCTGATCTGGAGGTCGTCACCAGCACCT
  IleThrLysPheIleMetAlaCysMetSerAlaAspLeuGluValValThrSerThrTrp 790        800        810        820        830        840
GGGTGCTGGTGGGCGGAGTCCTTGCAGCTCTGGCCGCATATCGCCTGACAACAGGCAGCG
  ValLeuValGlyGlyValLeuAlaAlaLeuAlaAlaTyrArgLeuThrThrGlySerVal 850        860        870        880        890        900
TGGTCATCGTGGGTAGGATCATCTTGTCTGGGAGGCCGGCTGTCATTCCCGACAGGGAAG
  ValIleValGlyArgIleIleLeuSerGlyArgProAlaValIleProAspArgGluVal

910
TCCTTTACCGG
  LeuTyrArg
```

Fig. 9

```
           10        20        30        40        50        60
CGACAACCGTGCCCCAAGACGCGGTGTCGCGCTCACAACGGCGGGGTAGGACAGGTAGGG
  ThrThrValProGlnAspAlaValSerArgSerGlnArgArgGlyArgThrGlyArgGly 70        80        90       100       110       120
GCAGGAGAGGCATCTACAGATTTGTGACTCCGGGAGAACGGCCCTCGGGCATGTTCGATT
  ArgArgGlyIleTyrArgPheValThrProGlyGluArgProSerGlyMetPheAspSer 130       140       150       160       170       180
CTTCGGTCCTGTGTGAGTGCTATGACGCGGGCTGCGCTTGGATCGAGCTCACGCCCGCCG
  SerValLeuCysGluCysTyrAspAlaGlyCysAlaTrpIleGluLeuThrProAlaGlu 190       200       210       220       230       240
AGACCTCAGTTAGGTTGCGGGCTTACCTAAATACACCAGGGTTGCCCGTCTGCCAGGACC
  ThrSerValArgLeuArgAlaTyrLeuAsnThrProGlyLeuProValCysGlnAspHis 250       260       270       280       290       300
ACCTGGAATTCTGGGAGAGCGTCTTCACAGGCCTCACCCATATAGATGCCCACTTCTTGT
  LeuGluPheTrpGluSerValPheThrGlyLeuThrHisIleAspAlaHisPheLeuSer 310       320       330       340       350       360
CCCAGACCAAGCAGGCAGGAGACAACTTCCCCTACCTGGTAGCATACCAAGCTACAGTGT
  GlnThrLysGlnAlaGlyAspAsnPheProTyrLeuValAlaTyrGlnAlaThrValCys 370       380       390       400       410       420
GCGCCAGGGCCCAGGCTCCACCACCATCGTGGGATCAAATGTGGAAGTGTCTCATACGGC
  AlaArgAlaGlnAlaProProProSerTrpAspGlnMetTrpLysCysLeuIleArgLeu 430       440       450       460       470       480
TGAAACCTACGCTACACGGGCCAACACCCCTGTTGTATAGGCTGGGAGCCGTCCAAAATG
  LysProThrLeuHisGlyProThrProLeuLeuTyrArgLeuGlyAlaValGlnAsnGlu

AGGTCACCC
  ValThr
```

Fig. 10a

```
1         10        20        30        40        50        60
GTGGTCTCCTGGGTGCCATCGTGGTCAGCCTAACGGGCCGCGACAAGAACCAGGTCGAGG
  GlyLeuLeuGlyAlaIleValValSerLeuThrGlyArgAspLysAsnGlnValGluG 70        80        90       100       110
GGGAGGTTCAGGTGGTCTCCACCGCAACGCAATCTTTCCTGGCGACCTGCGTCAATGGCGT
lyGluValGlnValValSerThrAlaThrGlnSerPheLeuAlaThrCysValAsnGlyVa 130       140       150       160       170
GTGTTGGACCGTCTACCATGGCGCCGGCTCGAAAACCCTGGCCGGCCCGAAGGGTCCAGTC
lCysTrpThrValTyrHisGlyAlaGlySerLysThrLeuAlaGlyProLysGlyProVal 190       200       210       220       230
ACCCAAATGTACACTAATGTGGACCAGGACCTCGTCGGCTGGCCGGCGCCCTCCGGGGCGC
ThrGlnMetTyrThrAsnValAspGlnAspLeuValGlyTrpProAlaProSerGlyAlaA 250       260       270       280       290
GGTCCTTGACACCATGCACCTGCGGCAGCTCGGACCTTTACTTGGTCACGAGGCATGCTGA
rgSerLeuThrProCysThrCysGlySerSerAspLeuTyrLeuValThrArgHisAlaAs 310       320       330       340       350       360
TGTCATTCCGGTGCGCCGGCGGGGCGATAGCAGGGGGAGCCTGCTTTCCCCCAGGCCCCTC
pValIleProValArgArgArgGlyAspSerArgGlySerLeuLeuSerProArgProLeu 370       380       390       400       410       420
TCCTACTTGAAGGGCTCCTCAGGTGGTCCACTGCTTTGCCCCTCGGGGCACATTGTGGGCA
SerTyrLeuLysGlySerSerGlyGlyProLeuLeuCysProSerGlyHisIleValGlyI 430       440       450       460       470       480
TCTTCCGGGCTGCCGTGTGCACCCGGGGGGTTGCGAAGGCGGTGGACTTTGTACCTGTCGA
lePheArgAlaAlaValCysThrArgGlyValAlaLysAlaValAspPheValProValGl 490       500       510       520       530       540
GTCTATGGAAACTACTATGCGGTCTCCGGTCTTCACGGATAATTCATCCCCCCCGGCCGTA
uSerMetGluThrThrMetArgSerProValPheThrAspAsnSerSerProProAlaVal 550       560       570       580       590       600
CCGCAGACATTCCAAGTGGCCCATCTGCATGCCCCCACTGGCAGCGGCAAGAGCACTAAGG
ProGlnThrPheGlnValAlaHisLeuHisAlaProThrGlySerGlyLysSerThrLysV 610       620       630       640       650       660
TGCCGGCTGCATACGCAGCCCAGGGATACAAGGTACTCGTCCTGAACCCGTCCGTTGCCGC
alProAlaAlaTyrAlaAlaGlnGlyTyrLysValLeuValLeuAsnProSerValAlaAl 680       690       700       710       720
CACCTTAGGTTTTGGAGCATATATGTCCAAGGCACATGGTGTCGACCCTAACATCAGGACT
aThrLeuGlyPheGlyAlaTyrMetSerLysAlaHisGlyValAspProAsnIleArgThr 740       750       760       770       780
GGGGTAAGGACCATCACTACGGGCGCCCCCATTACATACTCCACCTATGGCAAGTTTCTTG
GlyValArgThrIleThrThrGlyAlaProIleThrTyrSerThrTyrGlyLysPheLeuA
```

Fig. 10b

```
       800       810       820       830       840
CCGACGGTGGTTGCTCCGGGGGCGCCTATGACATCATAATATGTGATGAGTGCCACTCAAC
 laAspGlyGlyCysSerGlyGlyAlaTyrAspIleIleIleCysAspGluCysHisSerTh 860       870       880       890       900
TGACTCGACTTCCATTTTGGGCATTGGCACGGTCCTGGACCAAGCGGAGACGGCTGGAGCG
rAspSerThrSerIleLeuGlyIleGlyThrValLeuAspGlnAlaGluThrAlaGlyAla 920       930       940       950       960       970
CGGCTCGTCGTGCTCGCCACCGCTACGCCTCCAGGATCGGTCACTGTGCCTCATCCCAACA
ArgLeuValValLeuAlaThrAlaThrProProGlySerValThrValProHisProAsnI 980       990      1000      1010      1020      1030
TCGAGGAGGTGGCCTTGTCCAGCACTGGAGAGATTCCCTTCTATGGCAAAGCCATCCCCAT
leGluGluValAlaLeuSerSerThrGlyGluIleProPheTyrGlyLysAlaIleProIl 1040      1050      1060      1070
TGAGACCATCAAGGGGGGAAGGCATCTCATTTTCTGCCAC
eGluThrIleLysGlyGlyArgHisLeuIlePheCysHis
```

Fig. 11

```
1         10        20        30        40        50        60
GTCGACCCCAATATTAGAACTGGGGTAAGGACCATCACCACGGGCGCTCCCATTACGTAT
ValAspProAsnIleArgThrGlyValArgThrIleThrThrGlyAlaProIleThrTyr 70        80        90       100       110
TCTACCTATGGCAAATTCCTTGCCGACGGTGGTTGCTCTGGGGGCGCCTATGACATCATAA
SerThrTyrGlyLysPheLeuAlaAspGlyGlyCysSerGlyGlyAlaTyrAspIleIleI 130       140       150       160       170
TCTGTGATGAGTGCCACTCAACTGACTCGACTTCCATCTTGGGTATCGGCACAGCCCTGGA
leCysAspGluCysHisSerThrAspSerThrSerIleLeuGlyIleGlyThrAlaLeuAs 190       200       210       220       230
CCAAGCGGAGACGGCTGGAGCACGGCTTGTCGTGCTCGCCACCGCTACGCCTCCAGGGTCG
pGlnAlaGluThrAlaGlyAlaArgLeuValValLeuAlaThrAlaThrProProGlySer 250       260       270       280
GTCACCGTGCCGCATCCCAACATCGAGGAGGTAGCCTTGCC
ValThrValProHisProAsnIleGluGluValAlaLeu
```

Fig. 12

```
  1       10        20        30        40        50        60
GGACAACTCATCTCCCCCGGCGGTACCGCAGACATTCCAGGTGGCCCATCTACACGCTCC
 AspAsnSerSerProProAlaValProGlnThrPheGlnValAlaHisLeuHisAlaPr 70        80        90       100       110
CACTGGCAGCGGCAAGAGCACTAAGGTGCCGGCTGCATATGCAGCCCAAGGGTACAAAGTA
oThrGlySerGlyLysSerThrLysValProAlaAlaTyrAlaAlaGlnGlyTyrLysVal 130       140       150       160       170
CTCGTCCTGAACCCGTCCGTTGCCGCCACCTTAAGTTTCGGGGCGTATATGTCCAAGGCAC
LeuValLeuAsnProSerValAlaAlaThrLeuSerPheGlyAlaTyrMetSerLysAlaH 190       200       210       220       230
ATGGTGTTGACCCTAATATCAGAACTGGGACAAGGACCATCACCACGGGCGCTCCCATCAC
isGlyValAspProAsnIleArgThrGlyThrArgThrIleThrThrGlyAlaProIleTh 250       260       270       280       290
GTACTCCACCTATGGCAAGTTCCTTGCAGACGGTGGTTGCTCCGGAGGCGCCTATGACATC
rTyrSerThrTyrGlyLysPheLeuAlaAspGlyGlyCysSerGlyGlyAlaTyrAspIle 310       320       330       340       350       360
ATAATATGCGATGAGTGCCACTCAACAGACTCGACTTCCATCTTAGGCATTGGTACGGTCC
IleIleCysAspGluCysHisSerThrAspSerThrSerIleLeuGlyIleGlyThrValL 370       380       390       400       410       420
TGGACCAAGCGGAGACGGCTGGAGCGCGACTCGTCGTGCTCGCCACCGCTACGCCTCCAGG
euAspGlnAlaGluThrAlaGlyAlaArgLeuValValLeuAlaThrAlaThrProProGl 430       440       450       460       470       480
ATCGGTCACTGTGCCACATCCCAACATCGAGGAGGTGGCCCTGTCCAACACTGGAGAGATT
ySerValThrValProHisProAsnIleGluGluValAlaLeuSerAsnThrGlyGluIle 490       500       510       520       530       540
CCCTTCTATGGCAAAGCCATCCCCATTGAGGCCATCAAGGGGGGAGGCATCTCATTTTCT
ProPheTyrGlyLysAlaIleProIleGluAlaIleLysGlyGlyArgHisLeuIlePheC 550       560       570       580       590       600
GCCATTCTAAGAAGAAGTGTGATGAGCTCGCCACGAAGCTGTCGGCCCTCGGACTCAATGC
ysHisSerLysLysLysCysAspGluLeuAlaThrLysLeuSerAlaLeuGlyLeuAsnAl 610       620       630       640
TGTAGCGTACTACCGGGGTCTTGATGTGTCCG
aValAlaTyrTyrArgGlyLeuAspValSer
```

Fig. 13

```
1        10        20        30        40        50        60
CAGGCGAGAGGCCGACAGGGATGTTTGACAGCGTAGTGCTCTGTGAGTGCTATGATGCCG
   GlyGluArgProThrGlyMetPheAspSerValValLeuCysGluCysTyrAspAlaG 70        80        90       100       110
GGGCCGCCTGGTACGAGCTTACGCCTGCTGAGACTACGGTGAGACTCCGGGCTTATTTCAA
lyAlaAlaTrpTyrGluLeuThrProAlaGluThrThrValArgLeuArgAlaTyrPheAs 130       140       150       160       170
CACGCCCGGTTTGCCTGTATGTCAAGACCACCTAGAGTTCTGGGAAGCGGTCTTCACAGGT
nThrProGlyLeuProValCysGlnAspHisLeuGluPheTrpGluAlaValPheThrGly.

190       200       210       220       230
CTCACACACATTGATGCCCACTTCCTCTCCCAGACGAAGCAAGGAGGAGACAACTTTGCGT
LeuThrHisIleAspAlaHisPheLeuSerGlnThrLysGlnGlyGlyAspAsnPheAlaT.

250       260       270       280       290
ATCTAACGGCCTACCAGGCCACAGTATGCGCCAGGGCAAAGGCCCCCCCTCCTTCGTGGGA
yrLeuThrAlaTyrGlnAlaThrValCysAlaArgAlaLysAlaProProProSerTrpAs 310       320       330       340       350       360
CGTGATGTGGAAGTGTCTAATCAGGCTCAAACCTACATTGACTGGTCCTACCCCCCTCCTG.
pValMetTrpLysCysLeuIleArgLeuLysProThrLeuThrGlyProThrProLeuLeu 370       380       390       400       410       420
TACCGCTTGGGTGCCGTGACTAACGAGGTTACCCTGACGCACCCCGTGACGAAATATATCG
TyrArgLeuGlyAlaValThrAsnGluValThrLeuThrHisProValThrLysTyrIleA

430
CCACGT
laThr
```

Fig. 14

```
  1        10        20        30        40        50        60
ATGGGCACGAATCCTAAACCTCAAAGAAAAACCAAAAGAAACACTAACCGTCGCCCACAA
MetGlyThrAsnProLysProGlnArgLysThrLysArgAsnThrAsnArgArgProGln 70        80        90       100       110
GACGTTAAGTTTCCGGGCGGCGGCCAGATCGTTGGCGGAGTATACTTGTTGCCGCGCAGGG
AspValLysPheProGlyGlyGlyGlnIleValGlyGlyValTyrLeuLeuProArgArgG 130       140       150       160       170
GCCCCAGATTGGGTGTGCGCGCGACAAGGAAGACTTCGAAGCGGTCCCAGCCACGTGGGGG
lyProArgLeuGlyValArgAlaThrArgLysThrSerLysArgSerGlnProArgGlyGl 190       200       210       220       230
GCGCCGGCCCATCCCTAAAGATCGGCGCTCCACTGGCAAGTCCTGGGGGAAACCAGGATAC
yArgArgProIleProLysAspArgArgSerThrGlyLysSerTrpGlyLysProGlyTyr 250       260       270       280       290
CCCTGGCCCCTATATGGGAATGAGGGACTCGGCTGGGCAGGGTGGCTTCTGTCCCCCCGAG
ProTrpProLeuTyrGlyAsnGluGlyLeuGlyTrpAlaGlyTrpLeuLeuSerProArgG 310       320       330       340       350       360
GTTCCCGTCCCTCTTGGGGCCCCACTGACCCCCGGCATAGGTCGCGCAATGTGGGTAAGGT
lySerArgProSerTrpGlyProThrAspProArgHisArgSerArgAsnValGlyLysVa

CATC
lIle
```

Fig. 15a

```
1         10        20        30        40        50        60
CGCGCAACTTGGGTAAGGTCATCGATACCCTCACATGCGGCTTCGCCGACCTCATGGGGT
  ArgAsnLeuGlyLysValIleAspThrLeuThrCysGlyPheAlaAspLeuMetGlyT 70        80        90        100       110
ACATTCCGCTTGTCGGCGCCCCCCTAGGGGGTGCTGCCAGGGCCCTGGCACATGGTGTCCG
yrIleProLeuValGlyAlaProLeuGlyGlyAlaAlaArgAlaLeuAlaHisGlyValAr 130       140       150       160       170
GGTTCTGGAGGACGGCGTGAACTATGCAACAGGGAATTTGCCCGGTTGCTCTTTCTCTATC
gValLeuGluAspGlyValAsnTyrAlaThrGlyAsnLeuProGlyCysSerPheSerIle 190       200       210       220       230
TTCCTCTTGGCTTTGCTGTCCTGTTTGACCATCCCAGCTTCCGCTTATGAGGTGCGCAACG
PheLeuLeuAlaLeuLeuSerCysLeuThrIleProAlaSerAlaTyrGluValArgAsnV 250       260       270       280       290
TATCCGGGATATACCATGTCACGAACGACTGCTCCAACTCAAGTATTGTGTATGAGGCAGC
alSerGlyIleTyrHisValThrAsnAspCysSerAsnSerSerIleValTyrGluAlaAl 310       320       330       340       350       360
GGACATGATCATGCATACCCCCGGGTGCGTGCCCTGCGTTCGGGAGAACAACTCCTCCCGT
aAspMetIleMetHisThrProGlyCysValProCysValArgGluAsnAsnSerSerArg 370       380       390       400       410       420
TGCTGGGCAGCGCTCACTCCCACGTTAGCGGCCAGGAACACCAGCGTCCCCACTACGACAA
CysTrpAlaAlaLeuThrProThrLeuAlaAlaArgAsnThrSerValProThrThrThrI 430       440       450       460       470       480
TACGACGGCATGTCGATTTGCTCGTTGGGGCGGCTGCTTTCTGCTCCGCTATGTACGTGGG
leArgArgHisValAspLeuLeuValGlyAlaAlaAlaPheCysSerAlaMetTyrValGl
```

Fig. 15b

```
        490       500       510       520       530       540
   GGATCTCTGTGGATCTGTCTTCCTCGTTTCCCAGCTGTTCACTTTCTCACCTCGTCGGCAT
    yAspLeuCysGlySerValPheLeuValSerGlnLeuPheThrPheSerProArgArgHis 550       560       570       580       590       600
   GAGACAGTACAGGACTGCAACTGCTCAATCTATCCCGGCCACTTGACAGGTCATCGCATGG
    GluThrValGlnAspCysAsnCysSerIleTyrProGlyHisLeuThrGlyHisArgMetA 610       620       630       640       650       660
   CTTGGGATATGATGATGAACTGGTCACCTACAACAGCCCTAGTGGTGTCGCATCTACTCCG
    laTrpAspMetMetMetAsnTrpSerProThrThrAlaLeuValValSerHisLeuLeuAr 680       690       700       710       720
   GATCCCACAAGCTGTCATGGACATGGTGGCGGGGGCTCACTGGGGAGTCCTAGCGGGCCTC
    gIleProGlnAlaValMetAspMetValAlaGlyAlaHisTrpGlyValLeuAlaGlyLeu 740       750       760       770       780
   GCCTACTATTCCATGGTGGGGAACTGGGCTAAGGTTTTGATTGTGATGCTACTCTTCGCCG
    AlaTyrTyrSerMetValGlyAsnTrpAlaLysValLeuIleValMetLeuLeuPheAlaG 800       810       820       830       840
   GCGTTGACGGGACCACCTATGTGACAGGGGGGACGACAGGCCGCACCACCAGCTCGTTCGC
    lyValAspGlyThrThrTyrValThrGlyGlyThrThrGlyArgThrThrSerSerPheAl 860       870       880       890       900
   ATCCCTCTTTACACTTGGGTCGCATCAGAAGGTCCAGCTTATAAATACCAATGGCAGCTGG
    aSerLeuPheThrLeuGlySerHisGlnLysValGlnLeuIleAsnThrAsnGlySerTrp 920       930
   CACATCAACAGGACCGCC
    HisIleAsnArgThrAla
```

Fig. 16

```
1         10        20        30        40        50        60
CGCCGGTATGAGACGGCGCAAGACTGCAATTGCTCACTCTATCCCGGTCACGTATCTGGT
ArgArgTyrGluThrAlaGlnAspCysAsnCysSerLeuTyrProGlyHisValSerGly 70        80        90        100       110
CACCGCATGGCTTGGGATATGATGATGAACTGGTCACCTACAACGGCCCTAGTGGTATCGC
HisArgMetAlaTrpAspMetMetMetAsnTrpSerProThrThrAlaLeuValValSerG 130       140       150       160       170
AGCTACTCCGGATCCCACAAGCCGTCGTGGACATGGTGGCGGGGGCCCACTGGGGAGTCCT
lnLeuLeuArgIleProGlnAlaValValAspMetValAlaGlyAlaHisTrpGlyValLe 190       200       210       220       230
AGCGGGCCTTGCCTACTATTCCATGGTGGCGAACTGGGCTAAGGTCTTGGTTGTGATGCTA
uAlaGlyLeuAlaTyrTyrSerMetValAlaAsnTrpAlaLysValLeuValValMetLeu 250       260       270       280       290
CTCTTTGCCGGCGTTGACGACGGGAAGACCACCGTGACGGGGGGGAGCGCAGCCTTCCAGT
LeuPheAlaGlyValAspAspGlyLysThrThrValThrGlyGlySerAlaAlaPheGlnS 310       320       330       340       350       360
CCAGGAAGTTAGTGTCCTTCTTCTCACCAGGGCCGAAACAAAATATCCAGCTTGATAACAC
erArgLysLeuValSerPhePheSerProGlyProLysGlnAsnIleGlnLeuAspAsnTh 370       380       390       400       410       420
CAACGGCAGCTGGCACATCAACAGGACTGCCCTGAATTGCAATGACTCCCTCCAAACTGGG
rAsnGlySerTrpHisIleAsnArgThrAlaLeuAsnCysAsnAspSerLeuGlnThrGly 430       440       450       460       470       480
TTCATCGCTGCGCTGTTCTACGCGCACAAGTTCAATTCGTCCGGATGCCTAGAGCGCATGG
PheIleAlaAlaLeuPheTyrAlaHisLysPheAsnSerSerGlyCysLeuGluArgMetA 490       500       510       520       530       540
CCAGCTGCCGCCCCATTGACAAGTTCGCGCAGGGGTGGGGTCCCATCACTCACGATACGCC
laSerCysArgProIleAspLysPheAlaGlnGlyTrpGlyProIleThrHisAspThrPr

550
TAAGATCCCGG
oLysIlePro
```

Fig. 17

```
1         10        20        30        40        50        60
GACACCGTATGGCATGGGACATGATGATGAACTGGTCGCCCACGGCTACCATGATTCTGG
   HisArgMetAlaTrpAspMetMetMetAsnTrpSerProThrAlaThrMetIleLeuA 70        80        90        100       110
CGTATGTGATGCGCATCCCCGAGGTCGTCATGGACATCATTGGCGGGGCTCACTGGGGCGT
 laTyrValMetArgIleProGluValValMetAspIleIleGlyGlyAlaHisTrpGlyVa 130       140       150       160       170
CATGTTCGGCTTGGGCTATTTTTCTATGCAGGGGGCTTGGGCAAAAGTCGTTGTCATCCTT
 lMetPheGlyLeuGlyTyrPheSerMetGlnGlyAlaTrpAlaLysValValValIleLeu 190       200       210       220       230
CTGCTGGCCGCTGGGGTGGATGCGACTACCCTCAGCGTTGGGGGCTCTGCCGCGCACACCA
 LeuLeuAlaAlaGlyValAspAlaThrThrLeuSerValGlyGlySerAlaAlaHisThrT 250       260       270
CCGGCGGCCTTGTCGGCTTGTTCAAGCCTGGCG
 hrGlyGlyLeuValGlyLeuPheLysProGly
```

Fig. 18

```
1        10        20        30        40        50        60
CGCTTGTCGGCGCCCCCCTAGGGGGTGCTGCCAGGGCCCTGGCACATGGTGTCCGGGTTC
 LeuValGlyAlaProLeuGlyGlyAlaAlaArgAlaLeuAlaHisGlyValArgValL 70        80        90       100       110
TGGAGGACGGCGTGAACTATGCAACAGGGAATTTGCCCGGTTGCTCTTTCTCTATCTTCCT
 euGluAspGlyValAsnTyrAlaThrGlyAsnLeuProGlyCysSerPheSerIlePheLe 130       140       150       160       170
CTTGGCTTTGCTGTCCTGTTTGACCATCCCAGCTTCCGCTTATGAGGTGCGCAACGTATCC
 uLeuAlaLeuLeuSerCysLeuThrIleProAlaSerAlaTyrGluValArgAsnValSer 190       200       210       220       230
GGGATATACCATGTCACGAACGACTGCTCCAACTCAAGTATTGTGTATGAGGCAGCGGACA
 GlyIleTyrHisValThrAsnAspCysSerAsnSerSerIleValTyrGluAlaAlaAspM 250       260       270       280       290
TGATCATGCATACCCCCGGGTGCGTGCCCTGCGTTCGGGAGAACAACTCCTCCCGTTGCTG
 etIleMetHisThrProGlyCysValProCysValArgGluAsnAsnSerSerArgCysTr 310       320       330       340       350       360
GGCAGCGCTCACTCCCACGTTAGCGGCCAGGAACACCAGCGTCCCCACTACGACAATACGA
 pAlaAlaLeuThrProThrLeuAlaAlaArgAsnThrSerValProThrThrThrIleArg 370       380       390       400       410       420
CGGCATGTCGATTTGCTCGTTGGGGCGGCTGCTTTCTGCTCCGCTATGTACGTGGGGGATC
 ArgHisValAspLeuLeuValGlyAlaAlaAlaPheCysSerAlaMetTyrValGlyAspL 430       440       450       460       470       480
TCTGTGGATCTGTCTTCCTCGTTTCCCAGCTGTTCACTTTCTCACCTCGTCGGCATGAGAC
 euCysGlySerValPheLeuValSerGlnLeuPheThrPheSerProArgArgHisGluTh 490       500       510       520       530       540
AGTACAGGACTGCAACTGCTCAATCTATCCCGGCCACTTGACAGGTCATCGCATGGCTTGG
 rValGlnAspCysAsnCysSerIleTyrProGlyHisLeuThrGlyHisArgMetAlaTrp 550       560       570       580       590       600
GATATGATGATGAACTGGTCACCTACAACAGCCCTAGTGGTGTCGCATCTACTCCGGATCC
 AspMetMetMetAsnTrpSerProThrThrAlaLeuValValSerHisLeuLeuArgIleP 610       620       630       640       650       660
CACAAGCTGTCATGGACATGGTGGCGGGGGCCCACTGGGGAGTCCTAGCGGGCCTTGCCTA
 roGlnAlaValMetAspMetValAlaGlyAlaHisTrpGlyValLeuAlaGlyLeuAlaTy 680       690       700       710       720
CTATTCCATGGTGGGGAACTGGGCTAAGGTTTTGATTGTGATGCTACTCTTCGCCGGCGTT
 rTyrSerMetValGlyAsnTrpAlaLysValLeuIleValMetLeuLeuPheAlaGlyVal

740
GACGGGACCAC
 AspGlyThr
```

NON-A NON-B HEPATITIS-SPECIFIC ANTIGEN AND ITS USE IN HEPATITIS DIAGNOSIS

This is a divisional of copending application Ser. No. 08/081,072 filed on Jun. 22, 1993 which is a FWC of Ser. No. 07/726,141 filed on Jul. 8, 1991, now abandoned.

The present invention relates to a novel DNA fragment encoding non-A non-B hepatitis-specific antigen polypeptide which is found at the time of infection or onset of the non-A non-B hepatitis.

It also relates to an expression vector containing said DNA fragment, to a transformant transformed with said expression vector and to an expressed polypeptide obtained by culturing said transformant.

It further relates to a single strand DNA sequence for PCR primer synthesized on the basis of a partial base sequence of said DNA fragment.

It also relates to the use of said expressed polypeptide and said single strand DNA sequence in detection of the non-A non-B hepatitis virus.

BACKGROUND OF THE INVENTION

Non-A non-B hepatitis is an infectious disease which is caused by a masked virus other than A and B hepatitis viruses, but it is not easy to identify the virus because an amount of the virus-specific antigens is very small in a patient's body as well as of anti-virus antibodies. Accordingly, diagnosis of non-A non-B hepatitis has been made serologically by the well-known "diagnosis by exclusion" method wherein increase in the levels of alanine aminotransferase and aspartate aminotransferase is determined for a serum from a patient to make a diagnosis whether or not the hepatitis belongs to any of hepatitis A, hepatitis B, hepatitis D and other hepatitis symptoms due to the known hepatopathy-causing viruses such as CMV, EBV, etc, and if the result of diagnosis are not applicable to them, then a case is identified as non-A non-B hepatitis. It, however, is difficult to diagnose clinically as being non-A non-B hepatitis by such a method because there is no correlation between ALT value and non-A non-B hepatitis. Also, the lack of trustworthy means for the diagnosis is a serious problem, whereby a secondary infection with the non-A non-B hepatitis virus which may be caused by transfusing blood, especially, from a non-A non-B hepatitis virus-carrying healthy carrier into a person can hardly be prevented. Therefore, it is considered that the non-A non-B hepatitis occupies more than 90% of hepatitis cases caused by blood transfusion, with a total of about one million patients per one year.

In order to improve such situation and to raise a diagnostic accuracy of non-A non-B hepatitis, Alter's panel in which a standard serum is used has been developed by Alter at al at the NIH. Diagnostic materials which can pass the Alter's panel have been obtained by Arima et al [JIKKEN IGAKU (Japan), 7 (2), 196–201 (1989)] and by M. Houghton et al (WO 89/04669, PCT/JP90/500880) of Chiron Corp. almost simultaneously. Arima et al have screened the sera from hepatitis patients using λgt11 (a protein expression vector) which is derived from viral RNA from a non-A non-B hepatitis patient's serum. Also, Chiron Corp. have inoculated the patient's blood plasma into a chimpanzee to develop a chronic hepatitis, blood plasma being obtained from the diseased animal which possesses the anti-virus antibodies with high titer, and then have screened in the same way as Arima et al. Chiron Corp.'s group has also succeed in cloning almost the whole portion of the gene of a hepatitis C virus (HCV, designated by Chiron Corp. ) and developed a kit for diagnosis which comprises an antigen protein obtained by expressing a part of the HCV gene.

In spite of such an effort, however, factors of this disease, even their numbers, have not yet been elucidated to the full.

As described above, the two materials which can pass the Alter's panel has certainly lead to a new technique of diagnosis replaced by said "diagnosis by exclusion", but screening patient's sera separately with the materials gives no results to be satisfied because both the materials from Arima et al and Chiron Corp. react with patient's sera in low positive ratios of about 60 to 80% and about 50 to 70%, respectively. In other words, in some cases, these materials would not react with sera from the patients who have been diagnosed clinically as non-A non-B hepatitis. A virus commonly have a function to cause mutation in their host cells for their surval, and thus the viral genes isolated from American patients by Chiron Corp. had been possibly mutated into various forms acclimated to the chimpanzee as an infection intermediate.

Accordingly, a great demand has been directed to a large scale preparation of the reactive antigens which are capable of probing the non-A non-B hepatitis patients or carriers, therefor it will be necessary to construct effective cDNA clones through the isolation and purification of variously mutated vital RNA from many non-A non-B hepatitis patients.

In addition, in the case of sera which have failed in a trustworthy diagnosis using an antibody detection system, or of sera which are collected immediately after infection and in which antibody titers do not yet raise, a gene amplification method (PCR method) may be useful for the confirmation of the disease because it can detect a trace amount of vital genes. Also, it is possible to clone the genes efficiently by the PCR method. However, since the PCR method is carried out using primers which are synthesized from a known gene sequence, it is not always possible to detect a gene of the non-A non-B hepatitis virus in a patient's fluid using a primer(s) which can be constructed on the basis of the HCV gene sequences determined by Chiron Corp., if a difference in mutation between said HCV gene of Chiron Corp. and said patient-carried vital gene is significant.

In consequence, to detect efficiently infection with the non-A non-B hepatitis virus, it is necessary to prepare at least one primer capable of detecting the viral gene with a high specificity. Such a purpose may be accomplished by isolating a great number of cDNA clones, synthesizing primers from relatively preserved regions among their gene sequences, and subjecting the primers obtained to screening through the PCR method.

SUMMARY OF THE INVENTION

This invention provides a novel DNA fragment which encodes a non-A non-B hepatitis-specific antigen polypeptide originated from a non-structural or structural protein of the non-A non-B hepatitis virus, the polypeptide being formed at the time of the infection or onset of the non-A non-B hepatitis.

This invention also provides an expression vector containing the DNA fragment, a transformant transformed with the expression vector, an expressed polypeptide obtained by culturing the transformant, and a process for its production.

This invention further provides a primer for use in the detection of non-A non-B type hepatitis virus genes.

This invention further yet provides use of the expressed polypeptide or single strand DNA primer in detection of the non-A non-B hepatitis virus, and a method for the detection of non-A non-B type hepatitis virus genes and anti-non-A non-B type hepatitis virus antibodies.

BRIEF DESCRIPTION OF THE DRAWINGS

FIGS. 1a and 1b show a nucleotide sequence of non-A non-B hepatitis-specific cDNA which is encoded in a clone C11-7 and an amino acid sequence deduced from the sequence. These sequences are equivalent to SEQ ID NO. 1.

FIG. 2 shows a nucleotide sequence of non-A non-B hepatitis specific-cDNA which is encoded in a clone C10-11 and an amino acid sequence deduced from the sequence. These sequences are equivalent to SEQ ID NO. 2.

FIGS. 3a and 3b show a nucleotide sequence of non-A non-B hepatitis specific-cDNA which is encoded in a clone C10-13 and an amino acid sequence deduced from the sequence. These sequences are equivalent to SEQ ID NO. 3.

FIG. 4 shows a nucleotide sequence of non-A non-B hepatitis. specific-cDNA which is encoded in a clone C10-14 and an amino acid sequence deduced from the sequence. These sequences are equivalent to SEQ ID NO. 4.

FIGS. 5a and 5c show a nucleotide sequence of non-A non-B hepatitis-specific cDNA which is encoded in a clone C10-15 and an amino acid sequence deduced from the sequence. These sequences are equivalent to SEQ ID NO. 5.

FIGS. 6a and 6b show a nucleotide sequence of non-A non-B hepatitis specific-cDNA which is encoded in a clone C10-16 and an amino acid sequence deduced from the sequence. These sequences are equivalent to SEQ ID NO. 6.

FIG. 7 shows a nucleotide sequence of non-A non-B hepatitis specific-cDNA which is encoded in a clone C10-17 and an amino acid sequence deduced from the sequence. These sequences are equivalent to SEQ ID NO. 7.

FIGS. 8a and 8b show a nucleotide sequence of non-A non-B hepatitis-specific cDNA which is encoded in a clone C10-18 and an amino acid sequence deduced from the sequence. These sequences are equivalent to SEQ ID NO. 8.

FIG. 9 shows a nucleotide sequence of non-A non-B hepatitis-specific cDNA which is encoded in a clone C10-19 and an amino acid sequence deduced from the sequence. These sequences are equivalent to SEQ ID NO. 9.

FIGS. 10a and 10b show a nucleotide sequence of non-A non-B hepatitis-specific cDNA which is encoded in a clone C10-21 and an amino acid sequence deduced from the sequence. These sequences are equivalent to SEQ ID NO. 10.

FIG. 11 shows a nucleotide sequence of non-A non-B hepatitis-specific cDNA which is encoded in a clone C10-22 and an amino acid sequence deduced from the sequence. These sequences are equivalent to SEQ ID NO. 11.

FIG. 12 shows a nucleotide sequence of non-A non-B hepatitis-specific cDNA which is encoded in a clone C10-23 and an amino acid sequence deduced from the sequence. These sequences are equivalent to SEQ ID NO. 12.

FIG. 13 shows a nucleotide sequence of non-A non-B hepatitis-specific cDNA which is encoded in a clone C10-35 and an amino acid sequence deduced from the sequence. These sequences are equivalent to SEQ ID NO. 13.

FIG. 14 shows a nucleotide sequence, of non-A non-B hepatitis-specific cDNA which is encoded in a clone C11-C21 and an amino acid sequence deduced from the sequence. These sequences are equivalent to SEQ ID NO. 14.

FIGS. 15a and 15b show a nucleotide sequence of non-A non-B hepatitis-specific cDNA which is encoded in a clone C10-E12 and an amino acid sequence deduced from the sequence. These sequences are equivalent to SEQ ID NO. 15.

FIG. 16 shows a nucleotide sequence of non-A non-B hepatitis-specific cDNA which is encoded in a clone C10-E13 and an amino acid sequence deduced from the sequence. These sequences are equivalent to SEQ ID NO. 16.

FIG. 17 shows a nucleotide sequence of non-A non-B hepatitis-specific cDNA which is encoded in a clone C10-E24 and an amino acid sequence deduced from the sequence. These sequences are equivalent to SEQ ID NO. 17.

FIG. 18 shows a nucleotide sequence of non-A non-B hepatitis-specific cDNA which is encoded in a clone C10-E15 and an amino acid sequence deduced from the sequence. These sequences are equivalent to SEQ ID NO. 18.

DETAILED DESCRIPTION OF THE INVENTION

Figure 19:
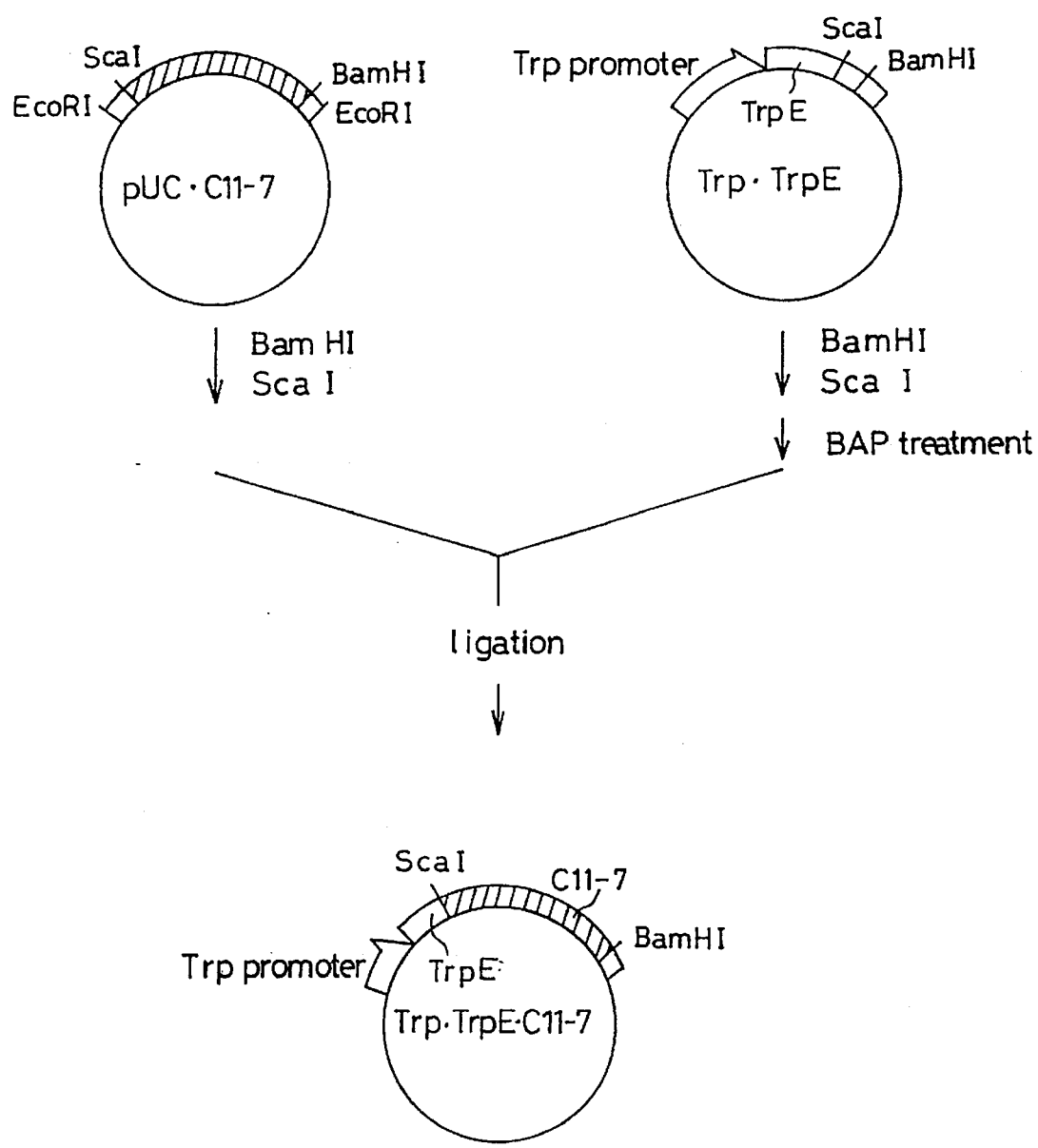
FIG. 19 shows a flow sheet for the construction of an expression plasmid Trp·TrpE·C11-7.

Many aspects and advantages of the present invention will be made apparent to those skilled in the art by the following detailed description about preferred embodiments of the invention.

The present invention provides a specified DNA fragment comprising a base sequence which encodes a non-A non-B hepatitis-specific antigen polypeptide from a non-structural or structural protein of the non-A non-B type hepatitis virus.

In preparation of the DNA fragment of the present invention, it is characterized that variously mutated genes of pathogenic viruses were directly collected from fresh blood plasma pools of a number of non-A non-B hepatitis patients. More particularly, the preparation comprises the steps in which total RNA molecules including non-A non-B hepatitis virus RNA are isolated from the blood plasma pool, cDNAs are synthesized based on the isolated RNA molecules by the well-known random primer method, and then the cDNAs obtained are incorporated into λ phage to prepare a cDNA library. The cDNA library is subsequently immunoscreened using sera from a non-A non-B hepatitis patient to obtain the DNA fragments of interest. Thereafter, using the resulting DNA fragments as probe, cDNA libraries obtained from the blood plasma from several chronic non-A non-B hepatitis patients were subjected to hybridization assay in order to isolate a cDNA which has different homology from the known counterparts and which is specific for the non-A non-B hepatitis patient.

Such a process makes it possible to provide the vital antigens which are markedly useful for the diagnosis of non-A non-B hepatitis patients carrying the variously mutated viruses and for the improvement of detection accuracy of the hepatitis viruses contained in blood for transfusion which was collected from many latent carriers carrying non-A non-B type hepatitis viruses.

The following describes the present invention in detail with regard to the preparation of cDNA library, isolation and sequencing of DNA fragments, expression and isolation of polypeptides, and their application to diagnosis of non-A non-B hepatitis using enzyme-linked immunosorbent assay (ELISA) or PCR method.

Preparation of cDNA library

Firstly, cell debris is removed from each of freshly collected blood plasma samples of several non-A non-B hepatitis patients by centrifugation and the resulting supernatant is again subjected to centrifugation at a higher speed of rotation to obtain a pellet. The pellet is subjected to an equilibrium density gradient centrifugation using cesium trifluoroacetate to isolate total RNA as a precipitate, and the total RNA is purified by phenol/chloroform extraction and ethanol precipitation.

By the method of Gubler and Hoffman using random primers, cDNA is synthesized from the above RNA fraction. The cDNA is methylated by treating it with a DNA methylase (for example, EcoRI methylase), connected with a DNA linker (for example, EcoRI linker) or DNA adapter (for example, EcoRI adapter), and then cloned into a cloning vector such as λ phage (for example, λgt10 or λgt11) to prepare a cDNA library.

Isolation and sequencing of DNA fragments

Next, *Escherichia coli* is infected with the λ phage cDNA library and cultured on an agar plate to form plaques. These plaques are transferred on a nitrocellulose filter, and subjected to blocking followed by immunoscreening using a non-A non-B hepatitis serum in order to detect positive clones. Alternatively, to improve efficiency of the screening, each positive clone obtained is cloned into a cloning vector such as plasmid and a $^{32}$P-labeled DNA probe is prepared by random primer technique, and then positive plaques are detected from the aforementioned cDNA library using the probe.

Eighteen clones in total were obtained by the above procedure and designated as C11-7, C10-11, C10-13, C10-14, C10-15, C10-16, C10-17, C10-18, C10-19, C10-21, C10-22, C10-23, C10-35, C11C21, C10-E12, C10-E13, C10-E24 and C10-E15.

A cDNA sample is obtained from k phage DNA of each 18 clones in a traditional manner and digested with appropriate restriction enzymes such as EcoRI and BamHI. Each cDNA fragment obtained is purified by agarose gel electrophoresis, incorporated into a sequencing vector (M13 phage), and then subjected to the dideoxy chain termination method [Sanger et al; *Proc. Natl. Acad. Sci.*, U.S.A., 74, 5463 (1977)] in order to determine a base sequence of each cDNA fragment.

Nucleotide sequences of these clones and deduced amino acid sequences are shown in FIGS. 1 to 18 and in a Sequence Listing which will be described later as SEQ ID NOS. 1 to 18. That is, the SEQ ID NOs. 1 to 18 respectively represent the nucleotide and deduced amino acid sequences determined from clones C11-7, C10-11, C10-13, C10-14, C10-15, C10-16, C10-17, C10-18, C10-19, C10-21, C10-22, C10-23, C10-35, C11-C21, C10-E12, C10-E13, C10-E24 and C10-E15. Also, the base pair (BP) number of their DNA fragments is 763 BP, 615 BP, 771 BP, 630 BP, 1426 BP, 855 BP, 315 BP, 911 BP, 489 BP, 1076 BP, 284 BP, 641 BP, 432 BP, 369 BP, 932 BP, 559 BP, 276 BP and 742BP, respectively.

All the 18 clones contained a continuous open reading frame but with no termination codon.

Analysis of genomic RNA has revealed that hepatitis C virus (HCV) is a class of virus similar to the genus Flavivirus such as Japanese encephalitis virus [Protein, *Nucleic Acid and Enzyme* (Japan), 35 (12), 2117–2127 (1990)]. From the comparison of homology between the reported gene and polypeptide of Flavivirus and those of the present invention, it was found that clones C11C12, C10-E12, C10-E13, C10-E24 and C10-E15 encode a structural protein of the non-A non-B type hepatitis virus. More particularly, clone C11-C21 is a gene which encodes the core of non-A non-B hepatitis virus, and clones C10-E12, C10-E13, C10-E24 and C10-E15 are genes encoding a region from the latter half of the virus core to the env or a region downstream from the env. Other clones were found to be genes encoding non-structural proteins of the virus.

The nucleotide sequences of the above 18 clones and the amino acid sequences translated along the open reading frames showed homologies with those of hepatitis C virus (HCV) reported by Houghton et al (EP-A-318,216, 1988). In other words, clones C11-7, C10-16, C10-17, C10-18, C10-19, C10-21, C10-22 and C10-23 showed relatively high homologies with HCV: 80 to 82% homology at nucleic acid level and 91 to 94% at amino acid level. In addition, these clones showed more higher homologies with the sequence J1 reported by Miyamura et al. (*Nuc. Aci. Res.*, 17, 10367–10372, 1989): 85 to 95% homology at nucleic acid level and 87 to 100% at amino acid level. These clones were classified as group 1 because of high homology in their overlapped portion. On the contrary, clones C10-11, C10-13, C10-14, C10-15 and C10-35 showed low homologies when compared to the nucleotide and amino acid sequences of HCV and J1, i.e., 69 to 70% homology at nucleic acid level and 75 to 80% at amino acid level they were therefore classified as group 2.

In addition, when the 369 BP nucleotide and deduced 123-amino acid sequences, indicated as SEQ ID NO. 14, for the C11-C21 clone encoding a structural protein of the virus were compared with the portions overlapped with HCV reported by Houghton et al (WO 90/11089), a nucleic acid homology of 81.8% and an amino acid homology of 87% were found. Also, when compared with HCV clones, HC-J1 and HC-J4, obtained from a Japanese patient (Okamoto et al.; *Japan J. Exp. Med.*, 60, 3, p. 167–177, 1990), homologies of 82.1% and 82.7% at nucleic acid level and 87.8% and 89.4% at amino acid level were shown. Since the same regions among the reported three clones (HCV by Houghton et al. and HC-J1 and HC-J4 by Okamoto et al.) have high homologies of 92.1 to 97.6% at nucleic acid level and 95.5 to 96.7% at amino acid level, it has been found that the clone C11-C21 obtained by the present inventors has a certain distance from the reported clones in terms of homology and therefore is a different group of viral gene therefrom. The remaining 4 clones, C10-E12, C10-E13 and C10-E15, showed homologies of 83 to 93% at nucleic acid level and 82 to 95% at amino acid level when compared with the HCV, HC-J1 and HC-J4, while C10-E24 showed around 63% of homology at nucleic acid level and around 60% of homology at amino acid level.

However, no homology was found either at nucleic acid level or amino acid level, when the DNA fragments of the present invention were compared with any DNA fragment encoding non-A non-B hepatitis antigens which have been disclosed in Japanese patent Application Laying-Open (KOKAI) Nos. 89/2576 and 89/124387.

Consequently, the clones C10-11, C10-13, C10-14, C10-15, C10-35, C11-C21, and C10-E24 have low homologies with the reported clones both at nucleic acid and amino acid levels. Other clones are also distinguishable from the reported clones.

Therefore, the present invention provides a DNA fragment comprising a base sequence which encodes a non-A non-B hepatitis-specific antigen polypeptide, said polypeptide consisting of the whole or a part of the amino acid sequence which is encoded along the open reading frame and represented by any one of the SEQ ID NOs. 1 to 18.

Naturally, the base sequences according to the present invention include any other base sequence which comprises other codons corresponding to each amino acid.

Among the aforementioned clones, C11-7, C10-11, C10-13, C10-14, C10-15, C10-16, C10-17, C10-18 and C10-19 were transformed into E. coli HB101 strain and deposited on Jul. 6, 1990 with Fermentation Research Institute, Agency of Industrial Science and Technology, 1-3 Higashi 1-chome, Tsukuba-shi, Ibaraki-ken, 305, Japan, respectively as E. coil HB101/C11-7 (Accession Number: FERM P-11589), E. coli HB101/C10-11 (FERM P-11581), E. coli HB101/C10-13 (FERM P-11582), E. coli HB101/C10-14 (FERM P-11583), E. coli HB101/C10-15 (FERM P-11584), E. coli HB101/C10-16 (FERM P-11585), E. coli HB101/C10-17 (FERM P-11586), E. coli HB101/C10-18 (FERM P-11587) and E. coli HB101/C10-19 (FERM P-11588). These depositions were subsequently converted on Jun. 13, 1991 to an international deposition under Budapest Treaty by the same depositary institution as an international depositary authority set forth in Budapest Treaty to be given the following new Accession Numbers:

| E. coli HB101 | Accession No. (FERM BP-) |
| --- | --- |
| Clone C11-7 | 3442 |
| Clone C10-11 | 3434 |
| Clone C10-13 | 3435 |
| Clone C10-14 | 3436 |
| Clone C10-15 | 3437 |
| Clone C10-16 | 3438 |
| Clone C10-17 | 3439 |
| Clone C10-18 | 3440 |
| Clone C10-19 | 3441 |

Also, clones C11-C21, C10-E12, C10-E13, C10-E24 and C10-E15 were transformed into E. coli JM109 strain and deposited on Dec. 11, 1990 with Fermentation Research Institute, Agency of Industrial Science and Technology, the same address, respectively under Accession Numbers FERM P-11892, FERM P-11894, FERM P-11895, FERMP-11896 and FERMP-11897. These depositions were also subsequently converted on Jun. 17, 1991 for clone C11-C12 and on Jun. 13, 1991 for other clones to an international deposition under Budapest Treaty in the same way. The following new Accession Numbers were given:

| E. coli JM109 | Accession No. (FERM BP-) |
| --- | --- |
| Clone C11-C21 | 3450 |
| Clone C10-E12 | 3444 |
| Clone C10-E13 | 3445 |
| Clone C10-E24 | 3446 |
| Clone C10-E15 | 3447 |

As described in the foregoing, the DNA fragments according to the present invention are different from any other prior DNA fragment. Though non-A non-B hepatitis virus is generally divided into two classes, namely groups 1 and 2, on the basis of the comparison of homology between the clones encoding a non-structural region of the hepatitis virus, there is a possibility of existing an intermediate group or even a third group because the virus is very susceptible to mutation in its host cells. It may be accordingly difficult to correctly diagnose all the non-A non-B hepatitis patients using an antigen protein prepared from only one kind of DNA fragment. In order to overcome such a problem and to improve an efficiency of the diagnosis, it is necessary to establish such a useful process for the preparation of DNA that a number of effective clones can easily be obtained, and to use several types of clones in combination in diagnosis
Expression of non-A non-B hepatitis specific antigen polypeptide The present invention also provides an expression vector which is constructed by introducing the above-mentioned DNA fragment into a cloning site downstream of a promoter gene in a vector.

Any conventional vector may be used such as plasmid, phage or the like. An expression vector may be constructed by the well-known techniques in the art. The following describes some processes for constructing the expression vectors of the invention.

Construction of expression plasmid Trp·TrpE·C11-7:

A flow sheet for the construction of the expression plasmid Trp·TrpE·C11-7 is shown in FIG. 19. Firstly, a plasmid pUC·C11-7 DNA obtained by incorporating the clone C11-7 into pUC119 is digested with restriction enzymes BamHI and ScaI, and the resulting BamHI-ScaI fragment is isolated by agarose gel electrophoresis and then purified by a glass powder technique. Separately from this, an expression vector Trp·TrpE DNA is digested with BamHI and ScaI, treated with a bacterial alkaline phosphatase (BAP), and then extracted with phenol. The aqueous layer obtained is subsequently subjected to ethanol precipitation to obtain a treated vector DNA. By connecting the vector DNA with the aforementioned C11-7 DNA fragment in the presence of T4 DNA ligase, the expression plasmid Trp·TrpE·C11-7 is obtained in which the DNA encoding the non-A non-B hepatitis-specific antigen is located downstream of a promoter so that transcription of the DNA can be controlled by the promoter.

Figure 20:
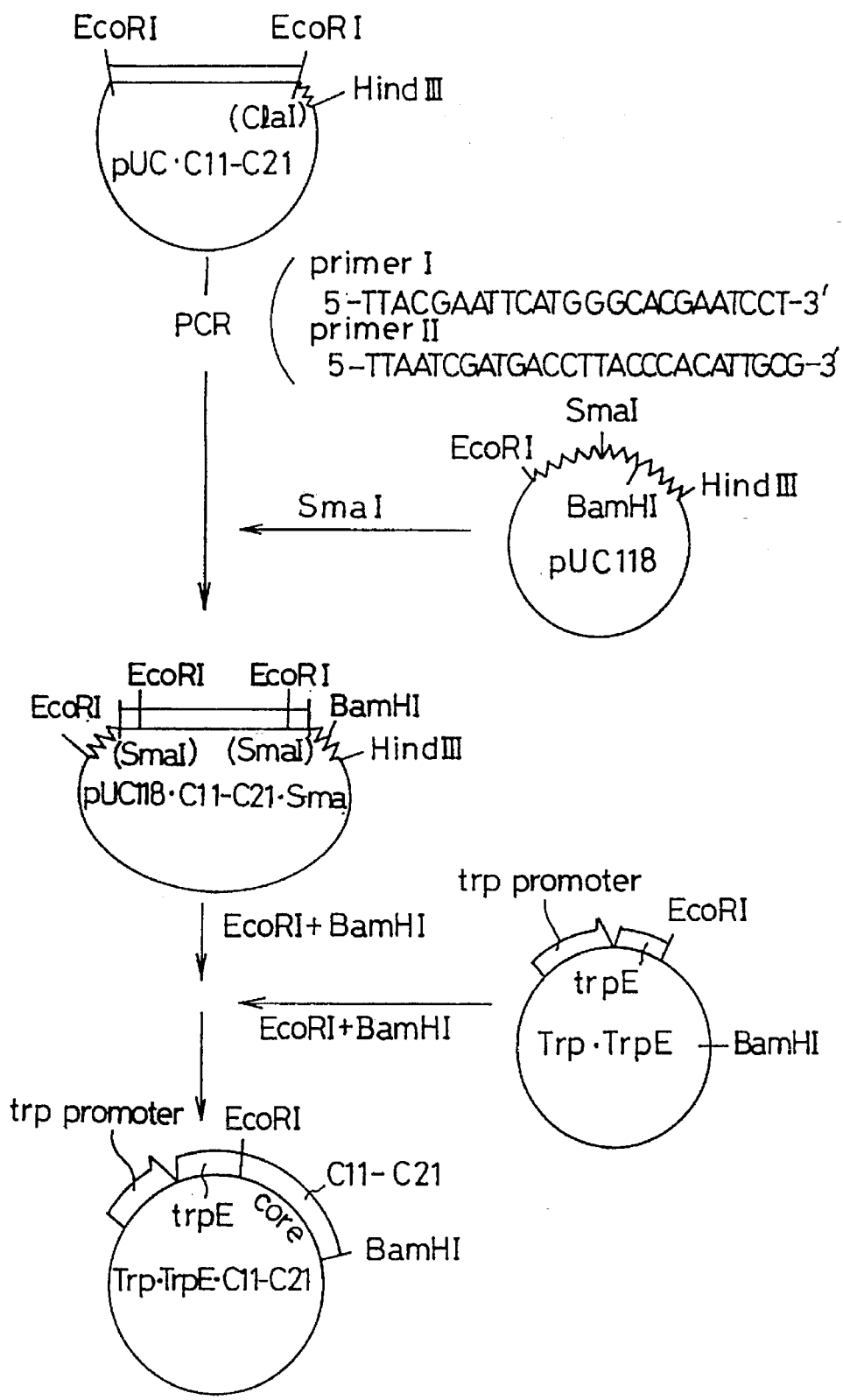
FIG. 20 shows a flow sheet for the construction of an expression plasmid Trp·TrpE·C11-C21.

Construction of expression plasmid Trp·TrpE·C11-C21:

A flow sheet for the construction of the expression plasmid Trp·TrpE·C11-21 is shown in FIG. 20.

Firstly, a DNA fragment containing a stop codon in its 3' SEQ ID NO: 23 terminal is prepared from a plasmid pUC·C11-C21 DNA which is obtained by incorporating the C11-C21 clone into pUC119, by a gene amplification method (PCR) using two primers (5'-TTACGAATTCATGGGCACGAATCCT-3' and 5'-TTAATCGATGACCTTACCCACATTGCG-3'SEQ ID NO: 24). By ligating the thus-prepared DNA fragment with pUC118 which is predigested with SmaI, a plasmid pUC118·C11-C21·Sma is obtained. This plasmid is then digested with EcoRI and BamHI; and the resulting DNA fragment is isolated by agarose gel electrophoresis and then purified by glass powder technique. Separately from this, an expression vector Trp·TrpE DNA (Japanese Patent Application No. 90/180889) is digested with BamHI and EcoRI, treated with a bacterial alkaline phosphatase (BAP), and then extracted with phenol. The aqueous layer obtained is subsequently subjected to ethanol precipitation to obtain a treated vector DNA. By connecting the vector DNA with the aforementioned C11-C21 DNA fragment by the action of T4 DNA ligase in a ligation buffer solution, the expression plasmid Trp·TrpE·C11-C21 is obtained in which the DNA-encoded polypeptide from a structural protein of the non-A non-B hepatitis virus is located downstream of a promoter so that transcription of the DNA can be controlled by the promoter.

Other clones can also be made into corresponding expression plasmids by treating each clone with appropriate restriction enzymes and introducing the treated fragment into an expression vector.

When a procaryote is used as the host cell, a promoter eligible for use in the present invention may be selected from promoters originated from E. coli, phage and the like, such as tryptophan synthase operon (trp), lactose operon (lac), λ phage $P_L$, λ phage $P_R$ and the like. When an eucaryote such as yeast is used as the host cell, promoters for 3-phosphoglycerate kinase and other glycolysis-related enzymes (Holland et al; Biochemistry, 17: 4900, 1978) may be useful. Though not always required, a transcription termination factor may preferably be located in the expression vector.

The vector may further contain a marker sequence, such as an ampicillin or a tetracycline resistance gene, which makes it possible to effect a phenotype selection in transformed cells.

The present invention also provides a transformant which is obtained by introducing the expression vector of the invention into a host cell. Microorganisms used commonly in this field, such as E. coli, B. subtilis, a yeast strain and the like, may be used as a host cell.

Transformation may be effected by any usually used means for the incorporation of an expression vector into host cells. When a bacterium (for example, E. coli) is used as host cell, a direct incorporation technique with the use of calcium chloride (Mandel, M. and Higa, A; J. Mol. Bio., 53, 159–162, 1970) may be employed.

In addition, the polypeptide of the present invention may be produced by inoculating and culturing a suitable host cell carrying the expression vector in an appropriate medium such as ampicillin,containing 2YT medium and then propagating expression cells by subculturing them in an ampicillin-containing phosphate medium.

Production and purification of recombinant non-A non-B hepatitis-specific antigen polypeptide The present invention also provides a process for producing a non-A non-B hepatitis-specific antigen polypeptide, which comprises the following steps of:

constructing a replicable expression vector which can express the aforementioned DNA fragment of the present invention in an appropriate host cell;

obtaining a transformant by incorporating said expression vector into the host cell;

producing a recombinant polypeptide by culturing said transformant under such conditions that said DNA fragment can be expressed; and recovering said recombinant polypeptide.

The crude polypeptide product from host cells may be purified by disintegration of the host cells, for example by ultrasonic disintegration, subjecting the disintegrated cells to centrifugation to obtain an insoluble fraction containing a fused polypeptide between TrpE as signal peptide and a polypeptide encoded by cDNA synthesized from a non-A non-B hepatitis virus RNA, extracting the fused polypeptide in a soluble form with a urea-containing buffer, and then purifying the extracted polypeptide by subjecting it to an ion exchange column chromatography (S-Sepharose, for example).

Accordingly, the present invention also provides a recombinant non-A non-B hepatitis-specific antigen polypeptide obtained by such a expression process, said polypeptide consisting of the whole or a part of the amino acid sequence represented by any one of the SEQ ID NOs. 1 to 18.

The term "recombinant non-A non-B hepatitis-specific antigen polypeptide" as used herein is intended to include a polypeptide itself which is obtained by expressing in a vector a DNA fragment encoding a non-A non-B hepatitis-specific antigen polypeptide, and a fused polypeptide obtained by fusing said polypeptide with other peptide such as a signal peptide.

Application to diagnosis of non-A non-B hepatitis

Figure 21:
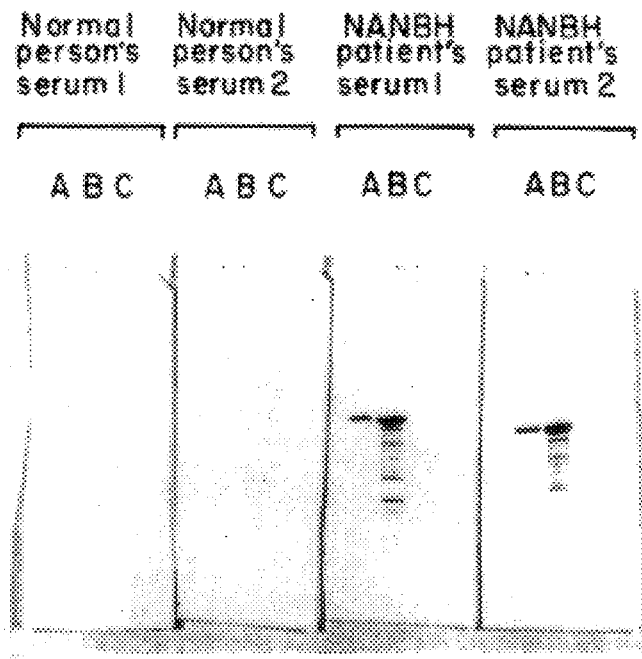
FIG. 21 is a photograph showing the results of western blotting analysis of an expressed product, TrpE-C11-7, with serum from a normal person or non-A non-B hepatitis patient, wherein the antigens used are a purified antigen in A, an extract of expressed cells in B, and an extract of non-expressed cells in C.
Figure 22:
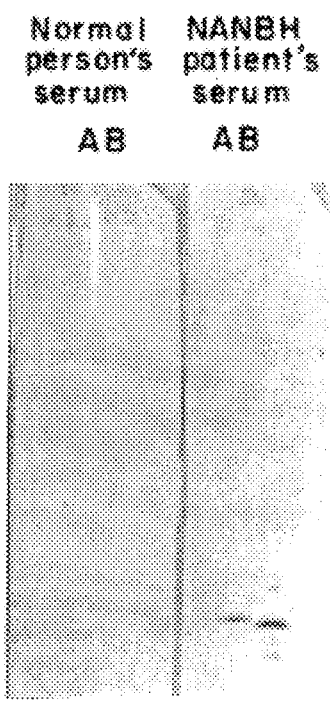
FIG. 22 is a photograph showing the results of western blotting of an expressed product, TrpE·C11-C21, with sera (A, B) from two normal persons or non-A non-B hepatitis patients.

The expressed polypeptide of the present invention was subjected to SDS-polyacrylamide gel electrophoresis and then allowed to perform antigen-antibody reaction with each two serum samples from normal persons or non-A non-B hepatitis patients by means of western blotting, whereby this polypeptide reacted strongly with only the patient's sera as shown in FIGS. 21 and 22. It was confirmed therefore that the expressed polypeptide functions as a non-A non-B hepatitis-specific antigen.

Accordingly, the present invention also provides a method for immunological detection to detect an antibody directed against the non-A non-B hepatitis virus antigen, which comprises the following steps of:

incubating a sample possibly containing an anti-non-A non-B hepatitis virus antibody together with at least one recombinant non-A non-B hepatitis-specific antigen polypeptide of the present invention under such conditions that the antigen is capable of reacting immunologically with the antibody; and detecting an antigen-antibody complex.

Figure 23:
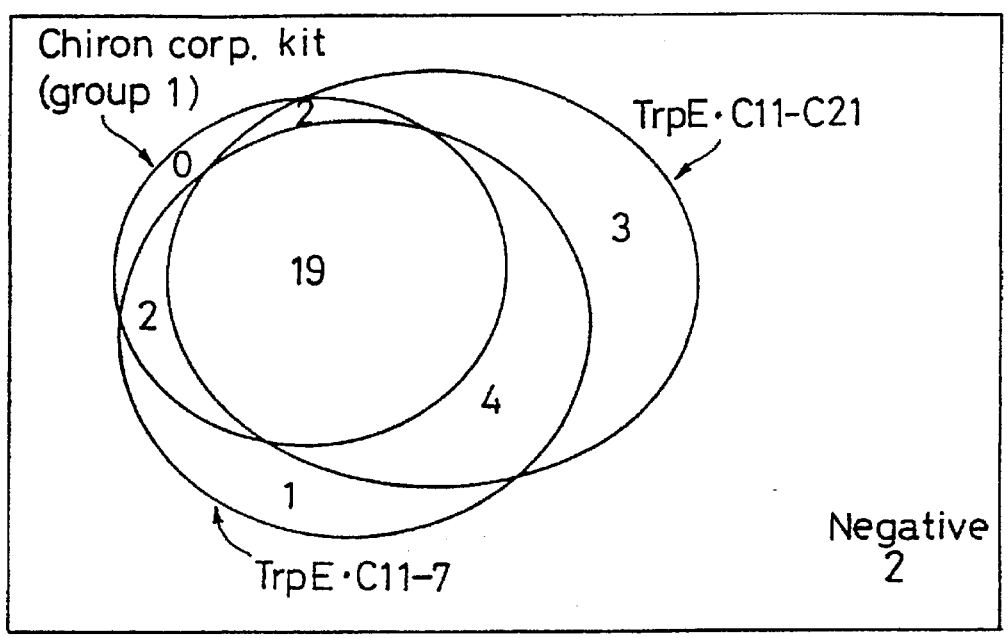
FIG. 23 is a graphical representation of the ELISA-determined positive numbers in Table 4.

Diagnostic effects (positiveness) of the expressed polypeptide TrpE·C11-C21 obtained by expressing the expression plasmid Trp·TrpE·C11-C21, another expressed polypeptide TrpE·C11-7 obtained by expressing the corresponding expression plasmid Trp·TrpE·C11-7, and an assay kit of Chiron Corp. (ORTHO HCV Ab ELISA kit) were examined by the conventional enzyme immunoassay through the reaction of the above expressed antigens with a serum sample from a patient who has been diagnosed clinically as being non-A non-B hepatitis. As the results, positiveness of the kit of Chiron Corp. was found to be 69.7% (23/33 cases) while the TrpE·C11-7 which belongs to group 1 showed a positiveness of 78.8% (26/33 cases). In the case of the expressed polypeptide TrpE·C11-C21, it showed a positiveness of 84.8% (28/33 cases) which is higher than the case of the Chiron's kit. When the expressed polypeptide TrpE·C11-7 as a member of group 1 and the TrpE·C11-C21 as a member of group 2 were used in combination, the positiveness increased to 93.9% (30/31 cases; see Table 1 and FIG. 23).

Therefore, according to an embodiment of the present invention, there is provided a combination of the group 1 and group 2-relating expressed polypeptides as a hepatitis-specific antigen polypeptide for use in the immunological detection.

The present invention further provides a method for gene amplification which comprises amplifying a non-A non-B hepatitis virus gene using sense and/or antisense sequence synthesized on the basis of the DNA sequences of the present invention.

As the synthetic base sequence for PCR primer, the following single strand DNA sequences may be employed:

5'-GGATACACCGGTGACTTTGA-3' (sense, SEQ ID NO. 19);

5'-TGCATGCACGTGGCGATGTA-3' (antisense, SEQ ID NO. 20);

5'-GATGCCCACTTCCTCTCCCA-3' (sense, SEQ ID NO. 21); and

5'-GTCAGGGTAACCTCGTTGGT-3' (antisense, SEQ ID NO. 22), said sequences being sense or antisense of the partial base sequence represented by the SEQ ID NO. 5 for the former two primers and by the SEQ ID NOs. 2, 4, 5 or 13 for the latter two primers. These specified primers are also within a scope of the invention.

The single strand DNA sequences may be synthesized by the usual methods such as phosphorous acid method, phosphotriester method, solid phase method and the like, though the use of a DNA synthesizer is most convenient.

When used as a PCR primer, the above single strand DNA sequences show higher specificity for the group 2 virus genes than for the group 1 virus genes (see Tables 2 and 3).

Therefore, the present invention also provides a method for detecting the genes from the non-A non-B type hepatitis virus in a fluid sample such as serum which comprises the following steps of:

isolating RNA from the sample, synthesizing cDNA by treating the obtained RNA with a reverse transcriptase, subjecting the obtained cDNA to polymerase chain reaction using at least one the above-mentioned primer;

detecting an amplified non-A non-B type hepatitis virus gene.

The present invention further provides use of the expressed polypeptides or single strand DNA sequences for PCR primer of the present invention in the detection of the non-A non-B hepatitis virus.

The following examples are given to further illustrate the present invention in detail, but it is not intended to limit the invention thereby.

EXAMPLE 1

Preparation of cDNA library from blood plasma of non-A non-B hepatitis patient

A cDNA library was prepared using λgt10 and λgt11 phages after preparing an RNA fraction in the following manner from fresh blood plasma pools obtained from several Japanese patients of chronic stage non-A non-B hepatitis.

Five liter of blood plasma was diluted with the equal volume of 50 mM Tris-HCl (pH 8.0) containing 1 mM EDTA, cell debris in the diluted sample was removed by centrifugation at 3,500 g for 20 minutes and then the resulting supernatant was again subjected to centrifugation at 45,000 rpm (about 100,000 g) for 4 hours at a temperature of 4° C. to obtain pellet. The pellet was dissolved, according to the conventional procedure, in 6M guanidium thiocyanate as a protein denaturating agent, layered over a solution of cesium trifluoroacetate, and then subjected to centrifugation using Beckman SW50 rotor at 33,000 rpm for 18 hours at a temperature of 20° C. The resulting pellet was dissolved in 10 mM Tris-HCl (pH 7.5) containing 1 mM EDTA and extracted twice with a solvent system of 1:1 phenol:chloroform, after which the organic layer was mixed with 1/10 volume of 5M NaCl and 2.5 volumes of ethanol. After standing the mixture for 2 hours at −20° C., it was centrifuged at 15,000 g for 20 minutes and the pellet was then dissolved in diethylpyrocarbonate-treated water to use as an RNA sample.

In accordance with the method of Gubler and Hoffman, cDNA was synthesized from the thus obtained RNA sample by means of random primer technique using a commercially available kit (from Amersham or BRL). The cDNA was subsequently treated with EcoRI methylase, ligated with an EcoRI linker or an EcoRI adapter and then cloned into the EcoRI site of λgt10 and λgt 11 phages. The cDNA library thus prepared contained $10^6$ to $10^7$ PFU of recombinant phages in average.

EXAMPLE 2

Isolation of non-A non-B hepatitis-specific cDNA

An attempt was made to isolate cDNA specific for non-A non-B hepatitis from the cDNA library prepared in Example 1, by immunoscreening and hybridization assay.

Firstly, immunoscreening of λgt11 library was carried out using two serum samples from non-A non-B hepatitis patients which are negative for HBc and HBs antibodies and which contain antibodies specific for the hepatitis-causing virus. Immunoscreening was performed in the usual way by examining specific reaction of a β-galactosidase-fused recombinant peptide with a serum sample of non-A non-B hepatitis (to be referred to as "NANBH" herein after) patient.

Cells of *E. coli* Y1090 strain were mixed with λgt11 cDNA library at a predetermined ratio, plated on an agar medium at an appropriate density, and then incubated at 43° C. for 3 hours to form plaques. Next, the agar plate was covered with a Hybond-C nitrocellulose filter which has been soaked with 10 mM IPTG and the filter-covered plate was incubated again at 37° C. for 3 hours to induce expression. Subsequently, the nitrocellulose filter was subjected to blocking using 3% gelatin solution, reacted with a serum sample of NANBH patient overnight at 4° C., and then, after washing, reacted with a peroxidase-labeled anti-human IgG (goat antibody). A positive signal was found when the resulting filter was reacted with a mixture of diaminobenzidine and $H_2O_2$. This clone, C11-7, did not react with HBc and HBs antibodies.

Next, in order to improve efficiency of the screening, the clone C11-7 was re-cloned into pUC119 and made into a probe by random primer method. Using the probe, λgt10 cDNA library was screened by means of hybridization assay. Screening was carried out according to the conventional method by plating $5×10^4$ PFU of recombinant phages with *E. coli* C-600 hfl(−) on an L-plate (150 mm dish). When plaques appeared after overnight incubation of the plate at 37° C., the plate was stored at 4° C. for 1 hour and thereafter the plate was covered with a Hybond-N filter for a period of 30 seconds. The resulting filter was superposed for 1 minute on a filter prewetted with a denaturating solution (0.5M NaOH and 1.5M NaCl), soaked for 5 minutes in a neutralizing solution (0.5M Tris-HCl pH 7.0 and 1.5M NaCl), washed with 2×SSC, and then dried. The filter was subjected to UV-crosslinking by exposing it to UV rays (304 nm) for 2 minutes. Thereafter, as described below, the resulting filter was subjected to screening by hybridization assay using a $^{32}$p-labeled DNA probe which has been prepared by random primer method from the C11-7 clone obtained by immunoscreening with a serum from NANBH patient.

The filter was incubated overnight at 65° C. in 1×SSC, washed twice with 1×SSC at 65° C. (10 minutes for each) and then subjected to autoradiography at −70° C. for the detection of positive plaques. Each positive plaque was transferred into SM buffer and used as a phage stock. Clones obtained were used as marker probe to carry out a series of screening. As the results, 13 clones in total were isolated and designated as C10-11, C10-13, C10-14, C10-15, C10-16, C10-i7, C10-18, C10-21, C10-22, C10-23 and C10-35.

EXAMPLE 3

Selective isolation of group 2 non-A non-B hepatitis-specific cDNA

A blood plasma sample which can react only with C10-14 clone was obtained by subjecting fresh blood plasma of a Japanese patient in a chronic phase of the non-A non-B hepatitis to an ELISA-based screening system, using expressed products of the group 1 cDNA clone C11-7 and the group 2 CDNA clone C10-14 isolated in Examples 1 and 2. This blood plasma sample was subjected to a gene amplification method (PCR method) using well preserved primers of group 1 and those of group 2. PCR method was carried out using Gene Amp™(DNA Amplification Reagent Kit, Perkin Elmer Cetus) under conditions of: DNA denaturation, 95° C. for 1.5 minutes; annealing, 55° C. for 2 minutes; and DNA synthesis, 70° C. for 3 minutes. Blood plasma samples in which gene amplification was found only with the use of the group 2 primers under these conditions were pooled for further use. An RNA fraction was prepared from one liter of this fresh blood plasma sample in the same manner as in Example 1, and a cDNA library (referred to as "cDNA library A" hereinafter) was constructed using λgt10 and λgt11 phages. The cDNA library A contained $10^6$ to $10^7$ PFU of recombinant phages in average.

On the other hand, a cDNA library B was constructed using λgt10 phage from five liters of fresh blood plasma samples which have been collected as starting material from several patients of non-A non-B hepatitis and have not been subjected to the ELISA/PCR method, in the same manner as described above. The cDNA library B also contained $10^6$ to $10^7$ PFU of recombinant phages in average.

Cloning of non-A non-B hepatitis-specific cDNA from cDNA library A was carried out by immunoscreening in the same manner as in Example 2, and a positive plaque (clone C11-C21) was obtained. The clone C11-C21 showed no positive reaction with HBc and HBs antibodies.

In order to improve efficiency of the screening, the thus obtained clone C11-C21 was re-cloned into pUC19, digested with restriction enzymes, and then made into a $^{32}$P-labeled probe by random primer labeling method in the same manner as in Example 2. Using the probe obtained, the cDNA library B was screened by hybridization assay. After a series of the screening efforts, 4 clones were isolated and named C10-E12, C10-E13, C10-E24 and C10-E15.

EXAMPLE 4

Sequencing of non-A non-B hepatitis-specific cDNA

E. coli cells were infected with the λgt11 or λgt10 phase of each of the 18 clones obtained in Examples 2 and 3 to recover respective phage in a large quantity. DNA was extracted from the phage by the conventional alkali method, digested with a restriction enzyme EcoRI, BamHI or KpnI, and the resulting DNA fragments were purified by agarose gel electrophoresis. Separately from this, sequencing vectors mp18 and mp19 of M13 phage (Messing, J.; *Methods in Enzymology*, 101, 20–78) or pUC118 and pUC119 (Vieira, J. and Messing, J.; *Methods in Enzymology*, 153, 3–11) were digested with a restriction enzyme EcoRI, BamHI or KpnI to obtain linear vector fragments. The cDNA fragment and the vector DNA were linked together Using T4 ligase in a buffer solution, and the resulting reaction product was incorporated into E. coli HB101 or JM109 strain by transformation or transfection. Resulting E. coli cells were cultured and DNA was recovered by alkali method. Nucleotide sequence of the DNA obtained was determined according to the dideoxy chain termination method of Sanger et al.

The nucleotide sequences of clones C10-11, C10-13, C10-14, C10-15, C10-16, C10-17, C10-18, C10-19, C10-21, C10-22, C10-23, C10-35, C10-C21, C10-E12, C10-E13, C10-E24 and C10-E15 and the amino acid sequences deduced from these nucleotide sequences are shown in a sequence table as SEQ ID NOs. 1 to 18 and also in FIGS. 1 to 18.

On the basis of the comparison of homologies among these sequences and the nucleotide and deduced amino acid sequences disclosed by Houghton et al.(WO89/04669, PCT/JP90/500880) and Miyamura et al (*Nuc. Aci. Res.*, 17, 10367–10372(1989)), clones C11-7, C10-17, C10-18, C10-19, C10-21, C10-22 and C10-23 obtained in Example 2 were classified as group 1 clone as defined hereabove while clones C10-11, C10-13, C10-14, C10-15 and C10-35 were classified as group 2 clones. Evry of these 13 clones encoded non-structural protein of the non-A non-B type hepatitis virus. Moreover, clone C10-C21 in Example 3 was classified as group 2 from the comparison of homology with the sequences described by Houghton et al (WO90/11089) and Okamoto et al (Japan *J. Exp. Med.*, 60, 3, pp.167–177 (1990)), but classification of the clones C10-E12, C10-E13, C10-E24 and C10-E15 in Example 3 is not still clear. However, it was found that these 5 clones encode the structural protein of non-A non-B hepatitis virus from the comparison of homology with the reported genome of Flavivirus (Protein, *Nucleic Acid and Enzyme* (Japan), 35 (12), 2117–2127 (1990)).

EXAMPLE 5

Expression and purification of polypeptide encoded by non-A non-B type hepatitis virus cDNA (i) Construction of expression plasmid Trp-TrpE-C11-7:

One of the clones isolated, C11-7, was expressed as a fused polypeptide with TrpE in E. coli under the control of Trp promoter(see FIG. 19).

Firstly, 1 μg of a plasmid pUC-C11-7 DNA which has been obtained by incorporating the C11-7 clone into pUC119 was digested by incubating it at 37° C. for 1 hour in 20 μl of a restriction enzyme reaction solution [150 mM NaCl, 6 mM Tris-HCl (pH 7.9), 6 mM $MgCl_2$, 15 units of ScaI enzyme]. Thereafter, a BamHI-ScaI fragment of about 700 bp was obtained by subjecting the resulting reaction solution to 0.8% agarose gel electrophoresis, and the fragment was purified by glass powder method (Gene Clean™, Bio-101).

One μg of Trp-TrpE DNA which is an expression vector was digested by incubating it at 37° C. for 1 hour in 20 μl of a reaction solution [150 mM NaCl, 6 mM Tris-HCl (pH 7.5), 6 mM $MgCl_2$, 15 units of BamHI enzyme and 15 units of ScaI enzyme]. After adding 39 μl of water, the resulting reaction solution was heat-treated at 70° C. for 5 minutes, mixed with 1 μl (250 U/μl) of a bacterial alkaline phosphatase (BAP) and then incubated at 37° C. for 1 hour. The reaction solution was subsequently extracted with phenol, the aqueous layer was subjected to ethanol precipitation followed by drying of the precipitate. One μg of the BamHI-ScaI-treated vector DNA obtained and the above C11-7 DNA fragment was added to 5 μl of 10×ligase buffer [660 mM Tris-HCl (pH 7.5), 66 mM $MgCl_2$, 100 mM dithiothreitol and 1 mM ATP] and 1 μl of T4 DNA ligase (350 U/μl), and water was then added to the mixture to 50 μl of the final volume. Thereafter, the thus prepared mixture was incubated overnight at 16° C. to complete ligation.

E. coli HB101 strain was transformed with 10 μl of the resulting reaction solution. Competent E. coli strain for use in the transformation was prepared by calcium chloride technique [Mandel, M. and Higa, A.; *J. Mol. Biol.*, 53, 159–162 (1970)]. The transformed *E. coli* strain cells were spread on an LB-plate (1% trypton, 0.5% yeast extracts, 0.5% NaCl and 1.5% agar) containing 25 µg/ml of ampicillin and incubated overnight at 37° C. One loopful of each colony grown on the plate was transferred into a liquid LB medium containing 25 µg/ml of ampicillin and cultured overnight at 37° C. Cells in 1.5 ml of the cultured medium were collected by centrifugation, and Miniprep of plasmid DNA was carried out by alkali method (Maniatis et al; *Molecular Cloning: A Laboratory Manual*, 1982). One µg of the plasmid DNA obtained was digested at 37° C. for 1 hour in 20 µl of a reaction solution [150 mM NaCl, 6 mM Tris-HCl (pH 7.5), 6 mM MgCl$_2$, 15 units of BamHI and 15 units of ScaI]. Thereafter, the digested solution was subjected to agarose gel electrophoresis to obtain an expression plasmid Trp·TrpE·C11-7 which can produce the 700 bp BamHI-ScaI fragment. This plasmid was transformed into *E. coli* HB101 strain and deposited on Jul. 6, 1990 with Fermentation Research Institute, 1-3 Higashi 1-chome, Tsukuba-shi, Ibaraki-ken, 305, Japan, under the Accession Number FERM P-11590 (named *E. coli* HB101/Trp·TrpE·C11-7). This deposition was subsequently converted on Jun. 13, 1991 to an international deposition under Budapest Treaty by the same depositary institution as an international depositary authority set forth in Budapest Treaty to be given the new Accession Number FERM BP-3443.

(ii) Expression and purification of polypeptide encoded by clone C11-7:

*E. coli* HB101 Strain transformed with the expression plasmid Trp·TrpE·C11-7 was inoculated into 3 ml of a liquid 2YT medium (1.6% trypton, 1% yeast extracts and 0.5% NaCl) containing 50 µg/ml of ampicillin and cultured at 37° C. for 9 hours. One ml portion of the cultured broth was inoculated into 100 ml of a liquid M9-CA medium (0.6% Na$_2$HPO$_4$, 0.5% KH$_2$PO$_4$, 0.5% NaCl, 0.1% NH$_4$Cl, 0.1 mM CaCl$_2$, 2 mM MgSO$_4$, 0.5% casamino acid and 0.2% glucose) containing 50 µg/ml of ampicillin and cultured at 37° C. for 21 hours. A 18-ml portion of the resulting culture broth was then inoculated into 1.2 l of the M9-CA medium and cultured at 37° C. When turbidity at OD$_{600}$ of the culture broth reached 0.3, indole acrylate was added to a final concentration of 40 mg/l, and the culturing was continued for additional 16 hours. Cells collected from the final culture broth by centrifugation were suspended in 20 ml of buffer A [50 mM Tris-HCl (pH 8.0), 1 mM EDTA and 30 mM NaCl] and the cell suspension was again subjected to centrifugation to obtain 2.6 g of expressed cells. The thus obtained cells were suspended in 10 ml of the buffer A, disintegrated by ultrasonic treatment, and then subjected to centrifugation to obtain an insoluble fraction containing a fused polypeptide of TrpE with a polypeptide which is encoded by the non-A non-B type hepatitis virus cDNA. The fused polypeptide in the insoluble fraction was solubilized and extracted using 10 ml of the buffer A containing 9M urea. Thereafter, the solubilized extract was subjected to an S-Sepharose ion exchange column chromatography with an NaCl gradient of from 0M to 0.5M to purify the fused polypeptide.

(iii) Construction of expression plasmid Trp·TrpE·C11-C21:

The clone C11-C21 was expressed as a fused polypeptide with TrpE in *E. coli* under the control of a promoter (see FIG. 20).

Firstly, 1 ng of plasmid pUC·C11-C21 DNA which has been obtained by incorporating C11-C21 clone into pUC119 was subjected to PCR method using two primers (5'-TTACGAATTCATGGGCACGAATCCT-3'SEQ ID NO: 3 and 5'TTAATCGATGACCTTACCCACATTGCG-3'SEQ ID NO: 24). PCR method was carried out using Gene Amp™ kit (DNA Amplification Reagent Kit, Perkin Elmer Cetus) under reaction conditions of: DNA denaturation, 95° C. for 1.5 minutes; annealing, 50° C. for 2 minutes; and DNA synthesis, 70° C. for 3 minutes. DNA fragments thus obtained were separated by 0.8% agarose gel electrophorests and purified by glass powder technique. Separately from this, pUC118 was digested with a restriction enzyme SmaI and then ligated with the DNA fragment obtained by PCR method in a buffer solution containing T4 ligase to obtain a plasmid pUC118-C11-C21-Sma. One µg of the plasmid DNA obtained was digested at 37° C. for 1 hour in a restriction enzyme reaction solution [150 mM NaCl, 6 mM Tris-HCl (pH 7.9), 6 mM MgCl$_2$, 15 units of EcoRI enzyme and 15 units of BamHI enzyme]. Thereafter, the resulting reaction mixture was subjected to 0.8% agarose gel electrophoresis to isolate an EcoRI-BamHI fragment of about 380 bp which was then purified by glass powder technique (Gene Clean™, Bio-101).

Next, ligation and transformation were carried out substantially in the same manner as in the aforementioned procedure (i) except that restriction digestion of the expression vector Trp·TrpE DNA was carried out using EcoRI and BamHI instead of BamHI and ScaI. Thereafter, an expression plasmid Trp·TrpE·C11-C21 which can produce the EcoRI-BamHI fragment of about 380 bp was selected by agarose gel electrophoresis purification. This plasmid was transformed into *E. coli* HB101 strain and deposited on Dec. 11, 1990 with Fermentation Research Institute, Agency of Industrial Science and Technology, the same address, under the Accession Number FERM P-11893 (named *E. coli* HB101/Trp·TrpE·C11-C21). The deposition was also subsequently converted on Jun. 17, 1991 to an international deposition under Budapest Treaty by the same depositary institution as an international depositary authority set forth in Budapest Treaty to be given the Accession Number FERM BP-3451.

(iv) Expression and purification of polypeptide encoded by clone C11-C21:

Expression and purification of a fused polypeptide were carried out substantially in the same manner as in the aforementioned procedure (ii), except that the expression plasmid Trp·TrpE·C11-C21 obtained by the above procedure (iii) was used instead of Trp·TrpE·C11-7.

EXAMPLE 6

Measurement of anti-non-A non-B type hepatitis virus antibody in serum from non-A non-B hepatitis patient (i) Measurement by western blotting:

The expressed product obtained and purified in Example 5 was subjected in turn to SDS-polyacrylamide gel electrophoresis [Laemmli; *Nature*, 277, 680 (1970)] and to blotting on a nitrocellulose filter (Bio-Rad, Trans-blot) in usual way. The filter was blocked with a 3% gelatin solution and then reacted with each serum samples from normal persons or non-A non-B hepatitis patients. After washing, the resulting filter was reacted with a peroxidase-labeled human IgG (goat antibody). Thereafter, the filter was washed again and soaked in a solution containing diaminobenzidine as reaction substrate to confirm color development.

The results are shown in FIGS. 21 and 22. In FIG. 21, the expressed polypeptide TrpE·C11-7 (group 1) obtained in Example 5-(ii) was used as antigen, and in FIG. 22, the expressed polypeptide TrpE·C11-C21 (group 2) in Example 5-(iv) was used. In each case, no reaction was observed with a normal serum sample, but a strong reaction with a patient's serum sample was found with a specific band.

(ii) Measurement by enzyme-linked immunosorbent assay (ELISA):

ELISA can be used as a means to make diagnosis of a large number of serum samples as compared to the case of western blotting method. ELISA was carried out as follows:.

A purified antigen sample was diluted with PBS(−) to a concentration of 5 μg/ml and fixed to a micro-plate at 4° C. or room temperature. After washing several times with a washing solution, a diluted serum sample to be detected was added to the resulting plate and incubated for 1 hour at 37° C. or room temperature. After washing, peroxidase-labeled anti-human IgG (goat antibody) was added and incubated at 37° C. or room temperature to complete the reaction. After washing several times, 50 μl of a diaminobenzidine solution was added and incubated at 37° C. to develop color. Thereafter, the coloring reaction was stopped with 2M $H_2SO_4$ and the color was measured by a colorimeter.

Positive ratios in the case of the use of the expressed polypeptide antigens, TrpE·C11-7 (group 1) and TrpE·C11-C21 (group 2), of the present invention were compared with the case of the use of a commercially available kit of Chiron Corp. (Ortho HCV Ab ELISA Test). As shown in Table 1, the use of the Chiron's kit resulted in 69.7% of the positive ratio, while positive ratios in the case of the use of the TrpE·C11-7 and TrpE·C11-C21 were 78.8% and 84.8%, respectively. Moreover, the positive ratio increased to 98.9% (30 of 31 cases) when these two expressed polypeptides of the present invention were used in combination (see FIG. 23).

EXAMPLE 7

Detection of non-A non-B type hepatitis virus group 2 gene in blood plasma from non-A non-B hepatitis patient by RT-PCR RT-PCR was carried out as follows:

To 100 μl of a blood plasma sample collected from a non-A non-B hepatitis patient was added 300 μl of a 6M GTC solution (6M guanidine thiocyanate, 25 mM sodium citrate, 0.5% sarcosyl and 0.2M 2-mercaptoethanol), and the mixture was stirred. To this were further added 40 μl of 2M sodium acetate (pH 5.2), 400 μl of phenol and 80 μl of chloroform/isoamyl alcohol (49:1), and then thoroughly stirred. Aqueous solution layer separated from the mixture was mixed with isopropyl alcohol and then subjected to centrifugation. Synthesis of cDNA was carried out using the pellet as a source of RNA. For the cDNA synthesis, an RNase inhibitor and a reverse transcriptase were added to a reaction solution containing 10 mM Tris-HCl, 0.01% gelatin, 1 mM each dNTP, 4 mM $MgCl_2$, 1 mM DTT and 100 pmole each primer, and the mixture was incubated at 37° C. for 2 hours to complete the reaction. Then, PCR was carried out using the cDNA obtained. In order to increase sensitivity and specificity for the detection of bands, a two step PCR method was employed, that is, first PCR using two primers (1st step PCR) and subsequent PCR using two primers which exist inside the first PCR product (2nd step PCR). For the PCR reaction, each amplification cycle was carried out using 100 μl of a reaction solution containing cDNA, 10 mM Tris-HCl, 0.01% gelatin, 2 mM each dNTP, 1.5 mM MgCl2 and 50 pmol each primer, under reaction conditions of: denaturation, 94° C. for 1.5 minutes; annealing, 50° C. for 2 minutes; and chain elongation, 70° C. for 2 minutes. The amplification cycle was repeated 35 times. Effects of several primers were evaluated. As the results, it was found that the group 2-specific DNA fragments are capable of being detected by the use of the following 4 primers:

1st step PCR

| | |
|---|---|
| kk21: 5'-GGATACACCGGTGACTTTGA-3' | 19 |
| kk22: 5'-TGCATGCACGTGGCGATGTA-3' | 20 |

2nd step PCR

| | |
|---|---|
| kk26: 5'-GATGCCCACTTCCTCTCCCA-3' | 21 |
| kk27: 5'-GTCAGGGTAACCTCGTTGGT-3' | 22 |

By applying these 4 primers to the PCR method, a DNA fragment of 206 bp can be detected. As a control, primers were synthesized from the base sequence of J1 and detection of group 1 DNA fragments was attempted. Results of the PCR from blood plasma samples of non-A non-B hepatitis patient are shown in Table 2.

It was known that DNA fragments from the non-A non-B hepatitis virus can be detected by both the PCRs using group 1 primers (i.e., group 1 PCR) and group 2 primers (i.e., group 2 PCR), and therefor two samples, Nos. 3 and 5, which are considered to include both groups 1- and 2-relating viruses were sequenced for their viral genes. As shown in Table 3, when nucleotide sequences of DNA fragments obtained by group 2 PCR were compared with C10-13 which is a group 2 clone, homologies of 85% and 88% were observed, indicating effective detection of group 2 genes. When these two nucleotide sequences were compared with the aforementioned group 1 clone J1 (Miyamura et al, supra), only 64.8% and 68% homologies were observed. Results of the homology evaluation indicate that the primers used in the group 2 PCR can selectively detect group 2 viral genes.

TABLE 1

| Sample No. | TrpE · C11-7 (group 1) | TrpE · C11-C21 (group 2) | Kit of Chiron Corp. (group 1) |
|---|---|---|---|
| 1 | +++ | +++ | +++ |
| 2 | +++ | +++ | ++ |
| 3 | + | +++ | +++ |
| 4 | +++ | + | +++ |
| 5 | − | +++ | +++ |
| 6 | +++ | + | ++ |
| 7 | +++ | +++ | +++ |
| 8 | +++ | +++ | +++ |
| 9 | +++ | ++ | +++ |
| 10 | ± | ± | − |
| 11 | +++ | − | ++ |
| 12 | +++ | +++ | − |
| 13 | +++ | − | + |
| 14 | +++ | +++ | +++ |
| 15 | +++ | +++ | +++ |
| 16 | +++ | + | +++ |
| 17 | − | − | − |
| 18 | + | + | + |
| 19 | + | +++ | − |
| 20 | ++ | ++ | +++ |
| 21 | +++ | +++ | ++ |
| 22 | − | ++ | − |
| 23 | − | − | − |
| 24 | + | + | + |
| 25 | +++ | +++ | +++ |
| 26 | − | ++ | − |
| 27 | +++ | +++ | ++ |
| 28 | + | + | +++ |
| 29 | +++ | +++ | +++ |
| 30 | +++ | ++ | +++ |
| 31 | − | ++ | +++ |
| 32 | − | ++ | − |
| 33 | + | − | − |
| NK | − | − | − |
| NP | − | − | − |

Note: NK and NP are negative controls.

TABLE 2

| Sample No. | Group 1 PCR | Group 2 PCR |
| --- | --- | --- |
| 1 | + | − |
| 2 | + | ± |
| 3 | + | + |
| 4 | + | − |
| 5 | + | + |
| 6 | + | − |
| 7 | + | − |
| 8 | + | − |
| 9 | + | − |
| 10 | + | − |
| 11 | + | + |
| 13 | − | + |
| 42 | − | + |
| 169 | + | + |
| 260 | − | + |
| 244 | − | − |
| 248 | − | + |
| NC | − | − |

TABLE 3

| Sample No. | Nucleotide homology with clone C10-13 |
| --- | --- |
| 3 | 85% |
| 5 | 88% |

As seen from the foregoing examples, the present invention has the following advantages:

The cDNA sequences according to the present invention are specific to non-A non-B hepatitis, and polypeptides which are produced by incorporating these genes into a protein expression system in microbial host cells such as *E. coli* can react immunologically with sera samples from a number of non-A non-B hepatitis patients, whereby a kit for diagnosing non-A non-B hepatitis is capable of preparing with markedly high sensitivity and judging accuracy. Also, it is possible to make diagnosis of this disease using said sequences as a probe directly or other probes with higher specificity synthesized on the basis of the sequences. In addition, not only diagnosis of the disease but also isolation of non-A non-B hepatitis-specific genes can be accomplished by employing a gene amplification method (PCR method).

---

What is claimed is:

1. A recombinant non-A non-B hepatitis-specific antigen polypeptide consisting of the amino acid sequence shown in SEQ ID NOS: 1 or 14.

2. A mixture of recombinant non-A non-B hepatitis-specific antigenic polypeptides, which mixture consists essentially of polypeptides, each polypeptide consisting of the amino acid sequence shown in SEQ ID Nos. 1 or 14.

* * * * *

SEQUENCE LISTING ( 1 ) GENERAL INFORMATION:

( i i i ) NUMBER OF SEQUENCES:24

( 2 ) INFORMATION FOR SEQ ID NO:1:

( i ) SEQUENCE CHARACTERISTICS:
        ( A ) LENGTH:763 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:1:

```
CG  CAG  TCA  TTC  CAA  GTG  GCC  CAT  CTA  CAC  GCT  CCC  ACT  GGC  AGC  GGC         47
    Gln  Ser  Phe  Gln  Val  Ala  His  Leu  His  Ala  Pro  Thr  Gly  Ser  Gly
     1              5                       10                      15

AAG  AGT  ACT  AAA  GTG  CCG  GCT  GCA  TAT  GCC  AGC  CAA  GGG  TAC  AAG  GTG         95
Lys  Ser  Thr  Lys  Val  Pro  Ala  Ala  Tyr  Ala  Ser  Gln  Gly  Tyr  Lys  Val
                    20                      25                      30

CTC  GTC  CTC  AAC  CCG  TCC  GTT  GCC  GCC  ACC  TTA  GGT  TTT  GGA  GCG  TAT        143
Leu  Val  Leu  Asn  Pro  Ser  Val  Ala  Ala  Thr  Leu  Gly  Phe  Gly  Ala  Tyr
               35                      40                      45

ATG  TCT  AAG  GCA  CAT  GGC  ACC  GAC  CCC  AAC  ATC  AGA  ACT  GGG  GTA  AGG        191
Met  Ser  Lys  Ala  His  Gly  Thr  Asp  Pro  Asn  Ile  Arg  Thr  Gly  Val  Arg
          50                      55                      60

ACT  ATC  ACC  ACA  GGC  GCC  CCC  ATC  ACG  TAC  TCC  ACC  TAC  GGC  AAG  TTC        239
Thr  Ile  Thr  Thr  Gly  Ala  Pro  Ile  Thr  Tyr  Ser  Thr  Tyr  Gly  Lys  Phe
     65                      70                      75

CTT  GCC  GAC  GGT  GGT  TGT  TCT  GGG  GGC  GCT  TAT  GAC  ATC  ATA  ATG  TGT        287
Leu  Ala  Asp  Gly  Gly  Cys  Ser  Gly  Gly  Ala  Tyr  Asp  Ile  Ile  Met  Cys
80                       85                      90                      95

GAT  GAG  TGC  CAC  TCA  ACT  GAC  GCG  ACT  TCC  ATC  TTG  GGC  ATC  GGC  ACG        335
```

```
        Asp Glu Cys His Ser Thr Asp Ala Thr Ser Ile Leu Gly Ile Gly Thr
                    100                 105                 110

GTC CTG GAC CAA GCG GAG ACG GCT GGA GCA CGG CTC GTC GTG CTC GCC         383
Val Leu Asp Gln Ala Glu Thr Ala Gly Ala Arg Leu Val Val Leu Ala
            115                 120                 125

ACC GCT ACG CCT CCG GGA TCG GTC ACC GTG CCA CAC CCG AAT ATT GAG         431
Thr Ala Thr Pro Pro Gly Ser Val Thr Val Pro His Pro Asn Ile Glu
            130                 135                 140

GAG GTG GCC CTG TCT AAC ACT GGA GAG ATC CCC TTC TAT GGC AAA GGC         479
Glu Val Ala Leu Ser Asn Thr Gly Glu Ile Pro Phe Tyr Gly Lys Gly
        145                 150                 155

ATC CCC ATT GAA GTC ATC AAG GGG GGA AGG CAT CTC ATT TTC TGC CAT         527
Ile Pro Ile Glu Val Ile Lys Gly Gly Arg His Leu Ile Phe Cys His
160                 165                 170                 175

TCC AAG AAG AAG TGC GAC GAG CTC GCC GCG AAG TTG TCA GGC CTC GGG         575
Ser Lys Lys Lys Cys Asp Glu Leu Ala Ala Lys Leu Ser Gly Leu Gly
                180                 185                 190

ATT AAT GCT GTG GCA TAC TAC CGG GGT CTT GAT GTG TCC GTC ATA CCG         623
Ile Asn Ala Val Ala Tyr Tyr Arg Gly Leu Asp Val Ser Val Ile Pro
                195                 200                 205

ACC AGC GGA GAC GTC GTT GTC GTG GCA ACA GAC GCT CTA ATG ACG GGC         671
Thr Ser Gly Asp Val Val Val Val Ala Thr Asp Ala Leu Met Thr Gly
            210                 215                 220

TAT ACC GGC GAT TTT GAC TCA GTG ATC GAC TGT AAC ACA TGC GTC ACC         719
Tyr Thr Gly Asp Phe Asp Ser Val Ile Asp Cys Asn Thr Cys Val Thr
        225                 230                 235

CAG ACA GTC GAC TTC AGC TTG GAC CCC ACC TTC ACC ATT GAG AC              763
Gln Thr Val Asp Phe Ser Leu Asp Pro Thr Phe Thr Ile Glu
240                 245                 250
```

( 2 ) INFORMATION FOR SEQ ID NO:2:

( i ) SEQUENCE CHARACTERISTICS:
        ( A ) LENGTH:615 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:2:

```
C ACG CCC GGT TTG CCC GTG TGT CAA GAC CAC CTG GAG TTC TGG GAA GCG       49
  Thr Pro Gly Leu Pro Val Cys Gln Asp His Leu Glu Phe Trp Glu Ala
   1               5                   10                  15

GTC TTC ACA GGT CTC ACG CAC ATT GAT GCC CAC TTC CTC TCC CAG ACA         97
Val Phe Thr Gly Leu Thr His Ile Asp Ala His Phe Leu Ser Gln Thr
            20                  25                  30

AAG CAA GGA GGA GAC AAC TTC GCG TAT CTA ACG GCC TAC CAG GCC ACA         145
Lys Gln Gly Gly Asp Asn Phe Ala Tyr Leu Thr Ala Tyr Gln Ala Thr
            35                  40                  45

GTG TGC GCT AGG GCA AAG GCC CCT CCT CCC TCG TGG GAT GTG ATG TGG         193
Val Cys Ala Arg Ala Lys Ala Pro Pro Pro Ser Trp Asp Val Met Trp
        50                  55                  60

AAA TGT CTA GCT AGG CTG AAG CCT ACA CTA ATT GGT CCT ACC CCC CTC         241
Lys Cys Leu Ala Arg Leu Lys Pro Thr Leu Ile Gly Pro Thr Pro Leu
65                  70                  75                  80

CTG TAC CGC TTG GGT GCC GTG ACC AAC GAG GTT ACC CTG ACG CAC CCC         289
Leu Tyr Arg Leu Gly Ala Val Thr Asn Glu Val Thr Leu Thr His Pro
                85                  90                  95

GTG ACG AAA TAC ATC GCC ACG TGC ATG CAA GCT GAC CTC GAG ATC ATG         337
Val Thr Lys Tyr Ile Ala Thr Cys Met Gln Ala Asp Leu Glu Ile Met
                100                 105                 110
```

```
ACG AGC ACA TGG GTC CTA GCA GGG GGG GTG CTA GCC GCC GTG GCA GCT     385
Thr Ser Thr Trp Val Leu Ala Gly Gly Val Leu Ala Ala Val Ala Ala
        115                 120                 125

TAC TGC CTG GCA ACC GGC TGT GTT TCC ATC ATC GGC CGC CTA CAC CTG     433
Tyr Cys Leu Ala Thr Gly Cys Val Ser Ile Ile Gly Arg Leu His Leu
    130                 135                 140

AAT GAT CAA GTG GTT GTG ACT CCT GAC AAA GAA ATC TTA TAT GAG GCC     481
Asn Asp Gln Val Val Val Thr Pro Asp Lys Glu Ile Leu Tyr Glu Ala
145                 150                 155                 160

TTT GAT GAG ATG GAA GAA TGC GCC TCC AAA GCC GCC CTC ATT GAG GAA     529
Phe Asp Glu Met Glu Glu Cys Ala Ser Lys Ala Ala Leu Ile Glu Glu
                165                 170                 175

GGG CAG CGG ATG GCG GAG ATG CTC AAG TCT AAG ATA CAA GGC CTC CTA     577
Gly Gln Arg Met Ala Glu Met Leu Lys Ser Lys Ile Gln Gly Leu Leu
            180                 185                 190

CAA CAG GCC ACA AGA CAG GCC CAA GAC ATA CAG CCA GC                  615
Gln Gln Ala Thr Arg Gln Ala Gln Asp Ile Gln Pro
        195                 200
```

( 2 ) INFORMATION FOR SEQ ID NO:3:

( i ) SEQUENCE CHARACTERISTICS:
        ( A ) LENGTH:771 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:3:

```
GT GAG CGA GCC TCA GGA ATG TTT GAC AGT GTA GTG CTC TGT GAG TGC       47
   Glu Arg Ala Ser Gly Met Phe Asp Ser Val Val Leu Cys Glu Cys
   1               5                   10                  15

TAT GAC GCA GGG GCT GCA TGG TAC GAG CTT ACA CCA GCG GAG ACC ACC      95
Tyr Asp Ala Gly Ala Ala Trp Tyr Glu Leu Thr Pro Ala Glu Thr Thr
                20                  25                  30

GTC AGG CTC AGA GCG TAT TTC AAC ACA CCT GGC TTG CCT GTG TGT CAA     143
Val Arg Leu Arg Ala Tyr Phe Asn Thr Pro Gly Leu Pro Val Cys Gln
            35                  40                  45

GAC CAT CTT GAG TTC TGG GAG GCA GTT TTC ACC GGC CTC ACA CAC ATA     191
Asp His Leu Glu Phe Trp Glu Ala Val Phe Thr Gly Leu Thr His Ile
        50                  55                  60

GAT GCC CAC TTC CTT TCC CAG ACA AAG CAA GCA GGG GAC AAT TTC GCA     239
Asp Ala His Phe Leu Ser Gln Thr Lys Gln Ala Gly Asp Asn Phe Ala
    65                  70                  75

TAC TTG ACA GCC TAC CAG GCT ACA GTG TGC GCC AGA GCC AAA GCC CCT     287
Tyr Leu Thr Ala Tyr Gln Ala Thr Val Cys Ala Arg Ala Lys Ala Pro
80                  85                  90                  95

CCC CCG TCC TGG GAC GTC ATG TGG AAG TGC CTG ACT CGG CTC AAG CCC     335
Pro Pro Ser Trp Asp Val Met Trp Lys Cys Leu Thr Arg Leu Lys Pro
                100                 105                 110

ACG CTT GTG GCC CCT ACA CCC CTT CTG TAC CGT TTA GGC TCT GTT ACT     383
Thr Leu Val Ala Pro Thr Pro Leu Leu Tyr Arg Leu Gly Ser Val Thr
            115                 120                 125

AAC GAG GTC ACC CTC ACA CAT CCT GTG ACG AAA TAC ATC GCC ACT TGC     431
Asn Glu Val Thr Leu Thr His Pro Val Thr Lys Tyr Ile Ala Thr Cys
        130                 135                 140

ATG CAA GCT GAC CTT GAG GTC ATG ACC AGC ACG TGG GTC CTA GCT GGG     479
Met Gln Ala Asp Leu Glu Val Met Thr Ser Thr Trp Val Leu Ala Gly
145                 150                 155

GGG GTC TTG GCA GCC GTC GCC GCG TAT TGC CTG GCG ACT GGG TGT GTC     527
```

```
Gly  Val  Leu  Ala  Ala  Val  Ala  Ala  Tyr  Cys  Leu  Ala  Thr  Gly  Cys  Val
160            165                      170                      175

TCC  ATC  ATC  GGC  CGC  TTG  CAC  ATC  AAT  CAG  CGA  GCC  GTC  GTT  GCA  CCA        575
Ser  Ile  Ile  Gly  Arg  Leu  His  Ile  Asn  Gln  Arg  Ala  Val  Val  Ala  Pro
               180                      185                      190

GAC  AAG  GAG  GTC  CTT  TAT  GAG  GCT  TTT  GAT  GAG  ATG  GAG  GAG  TGT  GCC        623
Asp  Lys  Glu  Val  Leu  Tyr  Glu  Ala  Phe  Asp  Glu  Met  Glu  Glu  Cys  Ala
               195                      200                      205

TCT  AAA  GCG  GCT  CTC  ATT  GAA  GAG  GGG  CAG  CGG  ATA  GCC  GAG  ATG  CTG        671
Ser  Lys  Ala  Ala  Leu  Ile  Glu  Glu  Gly  Gln  Arg  Ile  Ala  Glu  Met  Leu
          210                      215                      220

AAG  TCC  AAG  ATC  CAA  GGC  TTA  TTG  CAG  CAA  GCC  TCT  AAA  CAG  GCC  CAG        719
Lys  Ser  Lys  Ile  Gln  Gly  Leu  Leu  Gln  Gln  Ala  Ser  Lys  Gln  Ala  Gln
     225                      230                      235

GAC  ATA  CAA  CCC  GCT  GTG  CAG  CCT  CAT  GGC  CCA  AGG  TGG  AGC  AAT  TCT        767
Asp  Ile  Gln  Pro  Ala  Val  Gln  Pro  His  Gly  Pro  Arg  Trp  Ser  Asn  Ser
240                      245                      250                      255

GGG  C                                                                                 771
Gly
```

( 2 ) INFORMATION FOR SEQ ID NO:4:

( i ) SEQUENCE CHARACTERISTICS:
        ( A ) LENGTH:630 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:4:

```
C  TGG  TAT  GAA  CTT  ACG  CCT  GCT  GAG  ACT  ACG  GTG  AGA  CTC  CGG  GCC  TAT     49
   Trp  Tyr  Glu  Leu  Thr  Pro  Ala  Glu  Thr  Thr  Val  Arg  Leu  Arg  Ala  Tyr
   1              5                        10                       15

TTC  AAC  ACG  CCC  GGC  CTG  CCT  GTG  TGT  CAA  GAC  CAC  CTG  GAA  TTC  TGG        97
Phe  Asn  Thr  Pro  Gly  Leu  Pro  Val  Cys  Gln  Asp  His  Leu  Glu  Phe  Trp
               20                       25                       30

GAG  GCG  GTC  TTC  ACA  GGT  CTC  ACA  CAC  ATC  GAT  GCC  CAC  TTC  CTC  TCC        145
Glu  Ala  Val  Phe  Thr  Gly  Leu  Thr  His  Ile  Asp  Ala  His  Phe  Leu  Ser
          35                       40                       45

CAG  ACG  AAG  CAA  GGA  GGA  GAT  AAC  TTT  GCA  TAT  TTA  ACA  GCC  TAC  CAG        193
Gln  Thr  Lys  Gln  Gly  Gly  Asp  Asn  Phe  Ala  Tyr  Leu  Thr  Ala  Tyr  Gln
     50                       55                       60

GCC  ACA  GTC  TGC  GCT  AGG  GCA  AAG  GCT  CCC  CCT  CCT  TCG  TGG  GAC  GTG        241
Ala  Thr  Val  Cys  Ala  Arg  Ala  Lys  Ala  Pro  Pro  Pro  Ser  Trp  Asp  Val
65                       70                       75                       80

ATG  TGG  AAG  TGT  TTG  ATT  AGG  CTC  AAA  CCT  ACA  CTG  ACT  GGT  CCT  ACC        289
Met  Trp  Lys  Cys  Leu  Ile  Arg  Leu  Lys  Pro  Thr  Leu  Thr  Gly  Pro  Thr
               85                       90                       95

CCC  CTC  CTG  TAC  CGC  TTG  GGT  GCC  GTG  ACC  AAC  GAG  GTT  ACC  CTG  ACT        337
Pro  Leu  Leu  Tyr  Arg  Leu  Gly  Ala  Val  Thr  Asn  Glu  Val  Thr  Leu  Thr
               100                      105                      110

CAC  CCC  ATG  ACG  AAA  TAT  ATC  GCC  ACT  TGT  ATG  CAA  GCT  GAT  CTT  GAG        385
His  Pro  Met  Thr  Lys  Tyr  Ile  Ala  Thr  Cys  Met  Gln  Ala  Asp  Leu  Glu
          115                      120                      125

ATC  ATG  ACA  AGC  ACA  TGG  GTC  TTG  GCG  GGG  GGG  GTG  CTA  GCC  GCT  GTG        433
Ile  Met  Thr  Ser  Thr  Trp  Val  Leu  Ala  Gly  Gly  Val  Leu  Ala  Ala  Val
          130                      135                      140

GCA  GCT  TAC  TGC  CTA  GCG  ACC  GGC  TGC  ATT  TCC  ATC  ATT  GGC  CGC  CTT        481
Ala  Ala  Tyr  Cys  Leu  Ala  Thr  Gly  Cys  Ile  Ser  Ile  Ile  Gly  Arg  Leu
145                      150                      155                      160
```

| | | | | | | | | | | | | | | | | |
|---|---|---|---|---|---|---|---|---|---|---|---|---|---|---|---|---|
| CAC | CTG | AAT | GAT | CGG | GTG | GTC | GTG | ACC | CCT | GAT | AAG | GAA | ATT | TTA | TAT | 529 |
| His | Leu | Asn | Asp | Arg | Val | Val | Val | Thr | Pro | Asp | Lys | Glu | Ile | Leu | Tyr | |
| | | | | 165 | | | | | 170 | | | | | 175 | | |
| GAG | GCC | TTT | GAT | GAG | ATG | GAA | GAG | TGC | GCC | TCC | AAA | GCC | GCC | CTC | ATT | 577 |
| Glu | Ala | Phe | Asp | Glu | Met | Glu | Glu | Cys | Ala | Ser | Lys | Ala | Ala | Leu | Ile | |
| | | | 180 | | | | | 185 | | | | | 190 | | | |
| GAG | GAA | GGG | CAG | CGG | ATG | GCG | GAG | ATG | CTG | AAG | TCT | AAA | ATA | CAA | GGC | 625 |
| Glu | Glu | Gly | Gln | Arg | Met | Ala | Glu | Met | Leu | Lys | Ser | Lys | Ile | Gln | Gly | |
| | | 195 | | | | | 200 | | | | 205 | | | | | |
| CTC | TT | | | | | | | | | | | | | | | 630 |
| Leu | | | | | | | | | | | | | | | | |

( 2 ) INFORMATION FOR SEQ ID NO:5:

( i ) SEQUENCE CHARACTERISTICS:
        ( A ) LENGTH:1426 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:5:

| | | | | | | | | | | | | | | | | |
|---|---|---|---|---|---|---|---|---|---|---|---|---|---|---|---|---|
| GGG | ATC | AAC | CCT | AAC | ATC | AGG | ACC | GGA | GTA | CGG | ACC | GTG | ACC | ACC | GGG | 48 |
| Gly | Ile | Asn | Pro | Asn | Ile | Arg | Thr | Gly | Val | Arg | Thr | Val | Thr | Thr | Gly | |
| 1 | | | | 5 | | | | | 10 | | | | | 15 | | |
| GAC | TCC | ATC | ACC | TAC | TCC | ACT | TAT | GGC | AAG | TTT | ATC | GCA | GAT | GGA | GGT | 96 |
| Asp | Ser | Ile | Thr | Tyr | Ser | Thr | Tyr | Gly | Lys | Phe | Ile | Ala | Asp | Gly | Gly | |
| | | | 20 | | | | | 25 | | | | | 30 | | | |
| TGC | GCA | CAT | GGT | GCC | TAT | GAC | GTC | ATC | ATA | TGC | GAC | GAA | TGC | CAT | TCA | 144 |
| Cys | Ala | His | Gly | Ala | Tyr | Asp | Val | Ile | Ile | Cys | Asp | Glu | Cys | His | Ser | |
| | | 35 | | | | | 40 | | | | | 45 | | | | |
| GTG | GAC | GCT | ACT | ACC | ATC | CTT | GGC | ATT | GGA | ACA | GTC | CTT | GAC | CAG | GCT | 192 |
| Val | Asp | Ala | Thr | Thr | Ile | Leu | Gly | Ile | Gly | Thr | Val | Leu | Asp | Gln | Ala | |
| | 50 | | | | | 55 | | | | | 60 | | | | | |
| GAG | ACC | GCA | GGT | GCC | AGG | CTA | GTG | GTT | TTA | GCC | ACA | GCC | ACG | CCA | CCC | 240 |
| Glu | Thr | Ala | Gly | Ala | Arg | Leu | Val | Val | Leu | Ala | Thr | Ala | Thr | Pro | Pro | |
| 65 | | | | | 70 | | | | | 75 | | | | | 80 | |
| GGT | ACG | GTA | ACA | ACT | CCC | CAC | GCT | AAC | ATA | GAG | GAG | GTG | GCC | CTT | GGT | 288 |
| Gly | Thr | Val | Thr | Thr | Pro | His | Ala | Asn | Ile | Glu | Glu | Val | Ala | Leu | Gly | |
| | | | | 85 | | | | | 90 | | | | | 95 | | |
| CAC | GAA | GGC | GAG | ATT | CCT | TTT | TAT | GGC | AAG | GCT | ATT | CCC | CTA | GCT | TTC | 336 |
| His | Glu | Gly | Glu | Ile | Pro | Phe | Tyr | Gly | Lys | Ala | Ile | Pro | Leu | Ala | Phe | |
| | | | 100 | | | | | 105 | | | | | 110 | | | |
| ATC | AAG | GGG | GGC | AGA | CAC | CTA | ATT | TTT | TGC | CAT | TCA | AAG | AAG | AAG | TGC | 384 |
| Ile | Lys | Gly | Gly | Arg | His | Leu | Ile | Phe | Cys | His | Ser | Lys | Lys | Lys | Cys | |
| | | 115 | | | | | 120 | | | | | 125 | | | | |
| GAC | GAG | CTC | GCA | GCA | GCC | CTT | CGG | GGC | ATG | GGT | ATC | AAT | GCC | GTT | GCC | 432 |
| Asp | Glu | Leu | Ala | Ala | Ala | Leu | Arg | Gly | Met | Gly | Ile | Asn | Ala | Val | Ala | |
| | 130 | | | | | 135 | | | | | 140 | | | | | |
| TAC | TAC | AGG | GGT | CTC | GAC | GTC | TCC | GTT | ATA | CCA | ACT | CAA | GGA | GAC | GTG | 480 |
| Tyr | Tyr | Arg | Gly | Leu | Asp | Val | Ser | Val | Ile | Pro | Thr | Gln | Gly | Asp | Val | |
| 145 | | | | | 150 | | | | | 155 | | | | | 160 | |
| GTG | GTT | GTC | GCC | ACC | GAT | GCC | CTA | ATG | ACT | GGA | TAC | ACC | GGT | GAC | TTT | 528 |
| Val | Val | Val | Ala | Thr | Asp | Ala | Leu | Met | Thr | Gly | Tyr | Thr | Gly | Asp | Phe | |
| | | | | 165 | | | | | 170 | | | | | 175 | | |
| GAC | TCT | GTC | ATC | GAC | TGC | AAC | GTT | GCA | GTC | ACT | CAG | ATT | GTT | GAC | TTT | 576 |
| Asp | Ser | Val | Ile | Asp | Cys | Asn | Val | Ala | Val | Thr | Gln | Ile | Val | Asp | Phe | |
| | | | 180 | | | | | 185 | | | | | 190 | | | |
| AGC | CTA | GAC | CCA | ACT | TTT | ACC | ATC | ACC | ACT | CAA | ACC | GTC | CCT | CAG | GAG | 624 |
| Ser | Leu | Asp | Pro | Thr | Phe | Thr | Ile | Thr | Thr | Gln | Thr | Val | Pro | Gln | Glu | |
| | | 195 | | | | | 200 | | | | | 205 | | | | |

-continued

| | | | | | | | | | | | | | | | | |
|---|---|---|---|---|---|---|---|---|---|---|---|---|---|---|---|---|
| GCT | GTC | TCC | CGT | AGT | CAA | CGT | AGA | GGG | AGA | ACT | GGG | AGG | GGG | CGA | CTG | 672 |
| Ala | Val | Ser | Arg | Ser | Gln | Arg | Arg | Gly | Arg | Thr | Gly | Arg | Gly | Arg | Leu | |
| | 210 | | | | 215 | | | | | 220 | | | | | | |
| GGC | ACT | TAC | AGG | TAT | GTC | TCG | TCA | GGC | GAG | AGG | CCG | TCT | GGG | ATG | TTC | 720 |
| Gly | Thr | Tyr | Arg | Tyr | Val | Ser | Ser | Gly | Glu | Arg | Pro | Ser | Gly | Met | Phe | |
| 225 | | | | 230 | | | | | 235 | | | | | 240 | | |
| GAC | AGC | GTA | GTA | CTC | TGC | GAG | TGC | TAT | GAT | GCC | GGG | GCA | GCC | TGG | TAC | 768 |
| Asp | Ser | Val | Val | Leu | Cys | Glu | Cys | Tyr | Asp | Ala | Gly | Ala | Ala | Trp | Tyr | |
| | | | | 245 | | | | | 250 | | | | | 255 | | |
| GAG | CTT | ACA | CCT | GCT | GAG | ACC | ACA | GTG | AGA | CTC | CGG | GCT | TAT | TTC | AAC | 816 |
| Glu | Leu | Thr | Pro | Ala | Glu | Thr | Thr | Val | Arg | Leu | Arg | Ala | Tyr | Phe | Asn | |
| | | | 260 | | | | | 265 | | | | | 270 | | | |
| ACG | CCC | GGT | TTG | CCC | GTG | TGT | CAA | GAC | CAC | CTG | GAG | TTC | TGG | GAA | GCG | 864 |
| Thr | Pro | Gly | Leu | Pro | Val | Cys | Gln | Asp | His | Leu | Glu | Phe | Trp | Glu | Ala | |
| | | 275 | | | | | 280 | | | | | 285 | | | | |
| GTC | TTC | ACA | GGT | CTC | ACG | CAC | ATT | GAT | GCC | CAC | TTC | CTC | TCC | CAG | ACA | 912 |
| Val | Phe | Thr | Gly | Leu | Thr | His | Ile | Asp | Ala | His | Phe | Leu | Ser | Gln | Thr | |
| | 290 | | | | | 295 | | | | | 300 | | | | | |
| AAG | CAA | GGA | GGA | GAC | AAC | TTC | GCG | TAT | CTA | ACG | GCC | TAC | CAG | GCC | ACA | 960 |
| Lys | Gln | Gly | Gly | Asp | Asn | Phe | Ala | Tyr | Leu | Thr | Ala | Tyr | Gln | Ala | Thr | |
| 305 | | | | | 310 | | | | | 315 | | | | | 320 | |
| GTG | TGC | GCT | AGG | GCA | AAG | GCC | CCT | CCT | CCC | TCG | TGG | GAT | GTG | ATG | TGG | 1008 |
| Val | Cys | Ala | Arg | Ala | Lys | Ala | Pro | Pro | Pro | Ser | Trp | Asp | Val | Met | Trp | |
| | | | | 325 | | | | | 330 | | | | | 335 | | |
| AAA | TGT | CTA | GCT | AGG | CTG | AAG | CCT | ACA | CTA | ATT | GGT | CCT | ACC | CCC | CTC | 1056 |
| Lys | Cys | Leu | Ala | Arg | Leu | Lys | Pro | Thr | Leu | Ile | Gly | Pro | Thr | Pro | Leu | |
| | | | 340 | | | | | 345 | | | | | 350 | | | |
| CTG | TAC | CGC | TTG | GGT | GCC | GTG | ACC | AAC | GAG | GTT | ACC | CTG | ACG | CAC | CCC | 1104 |
| Leu | Tyr | Arg | Leu | Gly | Ala | Val | Thr | Asn | Glu | Val | Thr | Leu | Thr | His | Pro | |
| | | 355 | | | | | 360 | | | | | 365 | | | | |
| GTG | ACG | AAA | TAC | ATC | GCC | ACG | TGC | ATG | CAA | GTG | AAC | CTC | GAG | ATC | ATG | 1152 |
| Val | Thr | Lys | Tyr | Ile | Ala | Thr | Cys | Met | Gln | Val | Asn | Leu | Glu | Ile | Met | |
| | 370 | | | | | 375 | | | | | 380 | | | | | |
| ACG | AGC | ACA | TGG | GTC | CTA | GCA | GGG | GGG | GTG | CTA | GCC | GCC | GTG | GCA | GCT | 1200 |
| Thr | Ser | Thr | Trp | Val | Leu | Ala | Gly | Gly | Val | Leu | Ala | Ala | Val | Ala | Ala | |
| 385 | | | | | 390 | | | | | 395 | | | | | 400 | |
| TAC | TGC | CTG | GCA | ACC | GGC | TGT | GTT | TCC | ATC | ATC | GGC | CGC | CTA | CAC | CTG | 1248 |
| Tyr | Cys | Leu | Ala | Thr | Gly | Cys | Val | Ser | Ile | Ile | Gly | Arg | Leu | His | Leu | |
| | | | | 405 | | | | | 410 | | | | | 415 | | |
| AAT | GAT | CAA | GTG | GTT | GTG | ACT | CCT | GAC | AAA | GAA | ATC | TTA | TAT | GAG | GCC | 1296 |
| Asn | Asp | Gln | Val | Val | Val | Thr | Pro | Asp | Lys | Glu | Ile | Leu | Tyr | Glu | Ala | |
| | | | 420 | | | | | 425 | | | | | 430 | | | |
| TTT | GAT | GAG | ATG | GAA | GAA | TGC | GCC | TCC | AAA | GCC | GCC | CTC | ATT | GAG | GAA | 1344 |
| Phe | Asp | Glu | Met | Glu | Glu | Cys | Ala | Ser | Lys | Ala | Ala | Leu | Ile | Glu | Glu | |
| | | 435 | | | | | 440 | | | | | 445 | | | | |
| GGG | CAG | CGG | ATG | GCG | GAG | ATG | CTC | AAG | TCT | AAG | ATA | CAA | GGC | CTC | CTA | 1392 |
| Gly | Gln | Arg | Met | Ala | Glu | Met | Leu | Lys | Ser | Lys | Ile | Gln | Gly | Leu | Leu | |
| | 450 | | | | | 455 | | | | | 460 | | | | | |
| CAA | CAG | GCC | ACA | AGA | CAG | GCC | CAA | GAC | ATA | CAG | C | | | | | 1426 |
| Gln | Gln | Ala | Thr | Arg | Gln | Ala | Gln | Asp | Ile | Gln | | | | | | |
| 465 | | | | 470 | | | | | 475 | | | | | | | |

( 2 ) INFORMATION FOR SEQ ID NO:6:

( i ) SEQUENCE CHARACTERISTICS:
        ( A ) LENGTH:855 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:6:

```
CG CAG ACA TTC CAA GTG GCC CAT CTG CAC GCT CCC ACT GGT AGC GGC                 47
   Gln Thr Phe Gln Val Ala His Leu His Ala Pro Thr Gly Ser Gly
    1               5                  10                  15

AAG AGC ACT AAG GTG CCG GCT GCA TAT GCG GCC CAA GGG TAC AAG GTA                 95
Lys Ser Thr Lys Val Pro Ala Ala Tyr Ala Ala Gln Gly Tyr Lys Val
                 20                  25                  30

CTC GTC CTG AAC CCG TCC GTT GCC GCC ACT TTA GCC TTT GGG GCG TAC                143
Leu Val Leu Asn Pro Ser Val Ala Ala Thr Leu Ala Phe Gly Ala Tyr
             35                  40                  45

ATG TCT AAG GCA CAT GGT GTC GAC CCT AAC ATC AGA ACT GGG GTG AGG                191
Met Ser Lys Ala His Gly Val Asp Pro Asn Ile Arg Thr Gly Val Arg
         50                  55                  60

ACC ATC ACC ACG GGC GCT CCC ATC ACG TAC TCC ACC TAT GGT AAG TTC                239
Thr Ile Thr Thr Gly Ala Pro Ile Thr Tyr Ser Thr Tyr Gly Lys Phe
     65                  70                  75

CTT GCC GAC GGT GGT TGC TCT GGG GGC GCC TAT GAC ATC ATA ATA TGT                287
Leu Ala Asp Gly Gly Cys Ser Gly Gly Ala Tyr Asp Ile Ile Ile Cys
 80                  85                  90                  95

GAT GAG TGC CAC TCA ACT GAC TCG ACA TCC ATC TTG GGC ATC GGC ACA                335
Asp Glu Cys His Ser Thr Asp Ser Thr Ser Ile Leu Gly Ile Gly Thr
                100                 105                 110

GTC CTG GAC CAA GCG GAG ACG GCT GGA GCG CGG CTC GTC GTG CTC GCT                383
Val Leu Asp Gln Ala Glu Thr Ala Gly Ala Arg Leu Val Val Leu Ala
            115                 120                 125

ACC GCT ACG CCT CCG GGA TCG GTC ACC GTG CCA CAT CCC AAT ATC GAG                431
Thr Ala Thr Pro Pro Gly Ser Val Thr Val Pro His Pro Asn Ile Glu
        130                 135                 140

GAG GTG GCC CTG TCC ACC ACT GGA GAG ATT CCC TTC TAC GGC AAA GCT                479
Glu Val Ala Leu Ser Thr Thr Gly Glu Ile Pro Phe Tyr Gly Lys Ala
    145                 150                 155

ATC CCC ATC GAG ACA ATC AAG GGG GGG AGG CAT CTC ATC TTC TGC CGT                527
Ile Pro Ile Glu Thr Ile Lys Gly Gly Arg His Leu Ile Phe Cys Arg
160                 165                 170

175

TCC AAG AAG AAG TGT GAC GAG CTC GCT GGA AAG CTG TCA GCC CTC GGA                575
Ser Lys Lys Lys Cys Asp Glu Leu Ala Gly Lys Leu Ser Ala Leu Gly
                180                 185                 190

ATC AAC GCT GTA GCG TAC TAC CGG GGT CTT GAT GTA TCC GTC ATA CCG                623
Ile Asn Ala Val Ala Tyr Tyr Arg Gly Leu Asp Val Ser Val Ile Pro
            195                 200                 205

ACC AGC GGA GAC GTC GTT GTC GTG GCA ACA GAC GCT CTA ATG ACG GGC                671
Thr Ser Gly Asp Val Val Val Val Ala Thr Asp Ala Leu Met Thr Gly
        210                 215                 220

TAC ACC GGT GAC TTT GAT TCA GTG ATC GAC TGC AAT ACA TGT GTC ACC                719
Tyr Thr Gly Asp Phe Asp Ser Val Ile Asp Cys Asn Thr Cys Val Thr
    225                 230                 235

CAG ACA GTC GAC TTC AGC TTG GAC CCT ACC TTC ACC ATT GAG ACG ACG                767
Gln Thr Val Asp Phe Ser Leu Asp Pro Thr Phe Thr Ile Glu Thr Thr
240                 245                 250                 255

ACC GTG CCT CAA GAC GCG GTG TCA CGC TCG CAG CGG CGA GGC AGA ACT                815
Thr Val Pro Gln Asp Ala Val Ser Arg Ser Gln Arg Arg Gly Arg Thr
                260                 265                 270

GGT AGG GGT AGA GGG GGC ATA TAC AGG TTT GTG ACT CCA G                          855
Gly Arg Gly Arg Gly Gly Ile Tyr Arg Phe Val Thr Pro
            275                 280
```

( 2 ) INFORMATION FOR SEQ ID NO:7:

( i ) SEQUENCE CHARACTERISTICS:

( A ) LENGTH:315 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:7:

| GAC | GAG | CTC | GCC | GCA | AAG | CTG | TCA | GGC | CTC | GGA | GTC | AAT | GCT | GTG | GCA | 48 |
|---|---|---|---|---|---|---|---|---|---|---|---|---|---|---|---|---|
| Asp | Glu | Leu | Ala | Ala | Lys | Leu | Ser | Gly | Leu | Gly | Val | Asn | Ala | Val | Ala | |
| 1 | | | | 5 | | | | | 10 | | | | | 15 | | |

| TAC | TAC | CGG | GGT | CTC | GAT | GTG | TCT | GTC | ATA | CCG | ACG | AGC | GGG | GAC | GTC | 96 |
|---|---|---|---|---|---|---|---|---|---|---|---|---|---|---|---|---|
| Tyr | Tyr | Arg | Gly | Leu | Asp | Val | Ser | Val | Ile | Pro | Thr | Ser | Gly | Asp | Val | |
| | | | 20 | | | | | 25 | | | | | 30 | | | |

| GTT | GTT | GTG | GCA | ACA | GAC | GCT | CTA | ATG | ACG | GGC | TAT | ACC | GGC | GAC | TTT | 144 |
|---|---|---|---|---|---|---|---|---|---|---|---|---|---|---|---|---|
| Val | Val | Val | Ala | Thr | Asp | Ala | Leu | Met | Thr | Gly | Tyr | Thr | Gly | Asp | Phe | |
| | | 35 | | | | | 40 | | | | | 45 | | | | |

| GAC | TCG | GTG | ATC | GAC | TGC | AAT | ACA | TGT | GTC | ACC | CAA | ACA | GTC | GAT | TTC | 192 |
|---|---|---|---|---|---|---|---|---|---|---|---|---|---|---|---|---|
| Asp | Ser | Val | Ile | Asp | Cys | Asn | Thr | Cys | Val | Thr | Gln | Thr | Val | Asp | Phe | |
| | 50 | | | | | 55 | | | | | 60 | | | | | |

| AGC | TTG | GAC | CCT | ACT | TTC | ACC | ATT | GAG | ACG | ACG | ACC | GTG | CCC | CAA | GAC | 240 |
|---|---|---|---|---|---|---|---|---|---|---|---|---|---|---|---|---|
| Ser | Leu | Asp | Pro | Thr | Phe | Thr | Ile | Glu | Thr | Thr | Thr | Val | Pro | Gln | Asp | |
| 65 | | | | | 70 | | | | | 75 | | | | | 80 | |

| GCG | GTG | TCG | CGC | TCG | CAG | CGG | CGA | GGC | AGG | ACT | GGT | AGG | GGC | AGG | GTG | 288 |
|---|---|---|---|---|---|---|---|---|---|---|---|---|---|---|---|---|
| Ala | Val | Ser | Arg | Ser | Gln | Arg | Arg | Gly | Arg | Thr | Gly | Arg | Gly | Arg | Val | |
| | | | | 85 | | | | | 90 | | | | | 95 | | |

| GGC | ATA | TAC | AGG | TTT | GTG | ACT | CCC | GAG | | | | | | | | 315 |
|---|---|---|---|---|---|---|---|---|---|---|---|---|---|---|---|---|
| Gly | Ile | Tyr | Arg | Phe | Val | Thr | Pro | Glu | | | | | | | | |
| | | | 100 | | | | | 105 | | | | | | | | |

( 2 ) INFORMATION FOR SEQ ID NO:8:

( i ) SEQUENCE CHARACTERISTICS:
( A ) LENGTH:911 base pairs
( B ) TYPE:nucleic acid
( C ) STRANDEDNESS:double
( D ) TOPOLOGY:linear ( i i ) MOLECULE TYPE:cDNA to genomic RNA ( x i ) SEQUENCE DESCRIPTION: SEQ ID NO:8:

| GT | GAT | GAG | CTC | GCC | GCA | AAG | CTC | TCA | AGC | CTC | GGA | CTC | AAC | GCT | GTA | 47 |
|---|---|---|---|---|---|---|---|---|---|---|---|---|---|---|---|---|
| | Asp | Glu | Leu | Ala | Ala | Lys | Leu | Ser | Ser | Leu | Gly | Leu | Asn | Ala | Val | |
| | 1 | | | | 5 | | | | | 10 | | | | | 15 | |

| GCA | TAT | TAC | CGG | GGT | CTT | GAT | GTG | TCC | GTC | ATA | CCG | ACT | AGT | GGA | GAC | 95 |
|---|---|---|---|---|---|---|---|---|---|---|---|---|---|---|---|---|
| Ala | Tyr | Tyr | Arg | Gly | Leu | Asp | Val | Ser | Val | Ile | Pro | Thr | Ser | Gly | Asp | |
| | | | | 20 | | | | | 25 | | | | | 30 | | |

| GTC | GTT | GTC | GTG | GCA | ACA | GAC | GCT | CTA | ATG | ACG | GGC | TAT | ACC | GGC | GAC | 143 |
|---|---|---|---|---|---|---|---|---|---|---|---|---|---|---|---|---|
| Val | Val | Val | Val | Ala | Thr | Asp | Ala | Leu | Met | Thr | Gly | Tyr | Thr | Gly | Asp | |
| | | | 35 | | | | | 40 | | | | | 45 | | | |

| TTT | GAC | TCA | GTG | ATC | GAC | TGT | AAC | ACA | TGT | GTC | ACC | CAG | ACA | GTT | GAT | 191 |
|---|---|---|---|---|---|---|---|---|---|---|---|---|---|---|---|---|
| Phe | Asp | Ser | Val | Ile | Asp | Cys | Asn | Thr | Cys | Val | Thr | Gln | Thr | Val | Asp | |
| | | 50 | | | | | 55 | | | | | 60 | | | | |

| TTC | AGC | TTG | GAT | CCA | ACC | TTC | ACC | ATT | GAG | ACG | ACG | ACC | GTG | CCT | CAA | 239 |
|---|---|---|---|---|---|---|---|---|---|---|---|---|---|---|---|---|
| Phe | Ser | Leu | Asp | Pro | Thr | Phe | Thr | Ile | Glu | Thr | Thr | Thr | Val | Pro | Gln | |
| | 65 | | | | | 70 | | | | | 75 | | | | | |

| GAC | GCG | GTG | TCG | CGC | TCG | CAG | CGG | CGA | GGT | AGG | ACT | GGC | AGG | GGC | AGG | 287 |
|---|---|---|---|---|---|---|---|---|---|---|---|---|---|---|---|---|
| Asp | Ala | Val | Ser | Arg | Ser | Gln | Arg | Arg | Gly | Arg | Thr | Gly | Arg | Gly | Arg | |
| 80 | | | | | 85 | | | | | 90 | | | | | 95 | |

| GGC | GGC | ATC | TAT | AGG | TTT | GTG | ACT | CCA | GGA | GAA | CGG | CCC | TCG | GGC | ATG | 335 |
|---|---|---|---|---|---|---|---|---|---|---|---|---|---|---|---|---|
| Gly | Gly | Ile | Tyr | Arg | Phe | Val | Thr | Pro | Gly | Glu | Arg | Pro | Ser | Gly | Met | |
| | | | | 100 | | | | | 105 | | | | | 110 | | |

| TTC | GAT | TCC | TCG | GTC | CTG | TGT | GAG | TGT | TAT | GAC | GCG | GGC | TGT | GCT | TGG | 383 |

|     |     |     |     |     |     |     |     |     |     |     |     |     |     |     |     |
|-----|-----|-----|-----|-----|-----|-----|-----|-----|-----|-----|-----|-----|-----|-----|-----|
|     | Phe | Asp | Ser | Ser<br>115 | Val | Leu | Cys | Glu<br>120 | Cys | Tyr | Asp | Ala | Gly<br>125 | Cys | Ala | Trp |

```
TAT GAG CTC ACG CCC GCC GAG ACC ACG GTT AGG TTG CGG GCT TAC CTA      431
Tyr Glu Leu Thr Pro Ala Glu Thr Thr Val Arg Leu Arg Ala Tyr Leu
        130                     135                 140

AAT ACA CCA GGG TTG CCC GTC TGC CAG GAC CAT CTG GAG TTC TGG GAG      479
Asn Thr Pro Gly Leu Pro Val Cys Gln Asp His Leu Glu Phe Trp Glu
    145                     150                 155

GGC GTC TTC ACA GGC CTC ACC CAC ATA GAT GCC CAT TTC TTG TCT CAG      527
Gly Val Phe Thr Gly Leu Thr His Ile Asp Ala His Phe Leu Ser Gln
160                 165                 170                 175

ACT AAG CAG GCA GGA CAC AAC TTT CCC TAC CTG GTG GCA TAC CAA GCT      575
Thr Lys Gln Ala Gly His Asn Phe Pro Tyr Leu Val Ala Tyr Gln Ala
                180                 185                 190

ACA GTG TGC GCC AGG GCT CAG GCT CCA CCT CCA TCG TGG GAC CAA ATG      623
Thr Val Cys Ala Arg Ala Gln Ala Pro Pro Pro Ser Trp Asp Gln Met
            195                 200                 205

TGG AAG TGT CTC ATA CGG CTG AAA CCT ACG CTG CAC GGG CCA ACA CCC      671
Trp Lys Cys Leu Ile Arg Leu Lys Pro Thr Leu His Gly Pro Thr Pro
        210                 215                 220

CTG CTG TAT AGG CTA GGA GCC GTG GAA AAT GAG GTC ACC CTC ACA CAC      719
Leu Leu Tyr Arg Leu Gly Ala Val Glu Asn Glu Val Thr Leu Thr His
    225                 230                 235

CCC ATA ACC AAA TTC ATC ATG GCA TGC ATG TCG GCT GAT CTG GAG GTC      767
Pro Ile Thr Lys Phe Ile Met Ala Cys Met Ser Ala Asp Leu Glu Val
240                 245                 250                 255

GTC ACC AGC ACC TGG GTG CTG GTG GGC GGA GTC CTT GCA GCT CTG GCC      815
Val Thr Ser Thr Trp Val Leu Val Gly Gly Val Leu Ala Ala Leu Ala
                260                 265                 270

GCA TAT CGC CTG ACA ACA GGC AGC GTG GTC ATC GTG GGT AGG ATC ATC      863
Ala Tyr Arg Leu Thr Thr Gly Ser Val Val Ile Val Gly Arg Ile Ile
            275                 280                 285

TTG TCT GGG AGG CCG GCT GTC ATT CCC GAC AGG GAA GTC CTT TAC CGG      911
Leu Ser Gly Arg Pro Ala Val Ile Pro Asp Arg Glu Val Leu Tyr Arg
        290                 295                 300
```

(2) INFORMATION FOR SEQ ID NO:9:

(i) SEQUENCE CHARACTERISTICS:
    (A) LENGTH:489 base pairs
    (B) TYPE:nucleic acid
    (C) STRANDEDNESS:double
    (D) TOPOLOGY:linear (ii) MOLECULE TYPE:cDNA to genomic RNA (xi) SEQUENCE DESCRIPTION: SEQ ID NO:9:

```
CG ACA ACC GTG CCC CAA GAC GCG GTG TCG CGC TCA CAA CGG CGG GGT        47
   Thr Thr Val Pro Gln Asp Ala Val Ser Arg Ser Gln Arg Arg Gly
   1               5                   10                  15

AGG ACA GGT AGG GGC AGG AGA GGC ATC TAC AGA TTT GTG ACT CCG GGA       95
Arg Thr Gly Arg Gly Arg Arg Gly Ile Tyr Arg Phe Val Thr Pro Gly
                20                  25                  30

GAA CGG CCC TCG GGC ATG TTC GAT TCT TCG GTC CTG TGT GAG TGC TAT      143
Glu Arg Pro Ser Gly Met Phe Asp Ser Ser Val Leu Cys Glu Cys Tyr
            35                  40                  45

GAC GCG GGC TGC GCT TGG ATC GAG CTC ACG CCC GCC GAG ACC TCA GTT      191
Asp Ala Gly Cys Ala Trp Ile Glu Leu Thr Pro Ala Glu Thr Ser Val
        50                  55                  60

AGG TTG CGG GCT TAC CTA AAT ACA CCA GGG TTG CCC GTC TGC CAG GAC      239
Arg Leu Arg Ala Tyr Leu Asn Thr Pro Gly Leu Pro Val Cys Gln Asp
    65                  70                  75
```

| | | | | | | | | | | | | | | | | |
|---|---|---|---|---|---|---|---|---|---|---|---|---|---|---|---|---|
| CAC | CTG | GAA | TTC | TGG | GAG | AGC | GTC | TTC | ACA | GGC | CTC | ACC | CAT | ATA | GAT | 287 |
| His | Leu | Glu | Phe | Trp | Glu | Ser | Val | Phe | Thr | Gly | Leu | Thr | His | Ile | Asp | |
| 80 | | | | | 85 | | | | | 90 | | | | | 95 | |
| GCC | CAC | TTC | TTG | TCC | CAG | ACC | AAG | CAG | GCA | GGA | GAC | AAC | TTC | CCC | TAC | 335 |
| Ala | His | Phe | Leu | Ser | Gln | Thr | Lys | Gln | Ala | Gly | Asp | Asn | Phe | Pro | Tyr | |
| | | | | 100 | | | | | 105 | | | | | 110 | | |
| CTG | GTA | GCA | TAC | CAA | GCT | ACA | GTG | TGC | GCC | AGG | GCC | CAG | GCT | CCA | CCA | 383 |
| Leu | Val | Ala | Tyr | Gln | Ala | Thr | Val | Cys | Ala | Arg | Ala | Gln | Ala | Pro | Pro | |
| | | | 115 | | | | | 120 | | | | | 125 | | | |
| CCA | TCG | TGG | GAT | CAA | ATG | TGG | AAG | TGT | CTC | ATA | CGG | CTG | AAA | CCT | ACG | 431 |
| Pro | Ser | Trp | Asp | Gln | Met | Trp | Lys | Cys | Leu | Ile | Arg | Leu | Lys | Pro | Thr | |
| | | 130 | | | | | 135 | | | | | 140 | | | | |
| CTA | CAC | GGG | CCA | ACA | CCC | CTG | TTG | TAT | AGG | CTG | GGA | GCC | GTC | CAA | AAT | 479 |
| Leu | His | Gly | Pro | Thr | Pro | Leu | Leu | Tyr | Arg | Leu | Gly | Ala | Val | Gln | Asn | |
| | 145 | | | | 150 | | | | | 155 | | | | | | |
| GAG | GTC | ACC | C | | | | | | | | | | | | | 489 |
| Glu | Val | Thr | | | | | | | | | | | | | | |
| 160 | | | | | | | | | | | | | | | | |

( 2 ) INFORMATION FOR SEQ ID NO:10:

( i ) SEQUENCE CHARACTERISTICS:
     ( A ) LENGTH:1076 base pairs
     ( B ) TYPE:nucleic acid
     ( C ) STRANDEDNESS:double
     ( D ) TOPOLOGY:linear ( i i ) MOLECULE TYPE:cDNA to genomic RNA ( x i ) SEQUENCE DESCRIPTION: SEQ ID NO:10:

| | | | | | | | | | | | | | | | | |
|---|---|---|---|---|---|---|---|---|---|---|---|---|---|---|---|---|
| GT | GGT | CTC | CTG | GGT | GCC | ATC | GTG | GTC | AGC | CTA | ACG | GGC | CGC | GAC | AAG | 47 |
| | Gly | Leu | Leu | Gly | Ala | Ile | Val | Val | Ser | Leu | Thr | Gly | Arg | Asp | Lys | |
| | 1 | | | | 5 | | | | | 10 | | | | | 15 | |
| AAC | CAG | GTC | GAG | GGG | GAG | GTT | CAG | GTG | GTC | TCC | ACC | GCA | ACG | CAA | TCT | 95 |
| Asn | Gln | Val | Glu | Gly | Glu | Val | Gln | Val | Val | Ser | Thr | Ala | Thr | Gln | Ser | |
| | | | 20 | | | | | 25 | | | | | 30 | | | |
| TTC | CTG | GCG | ACC | TGC | GTC | AAT | GGC | GTG | TGT | TGG | ACC | GTC | TAC | CAT | GGC | 143 |
| Phe | Leu | Ala | Thr | Cys | Val | Asn | Gly | Val | Cys | Trp | Thr | Val | Tyr | His | Gly | |
| | | | 35 | | | | | 40 | | | | | 45 | | | |
| GCC | GGC | TCG | AAA | ACC | CTG | GCC | GGC | CCG | AAG | GGT | CCA | GTC | ACC | CAA | ATG | 191 |
| Ala | Gly | Ser | Lys | Thr | Leu | Ala | Gly | Pro | Lys | Gly | Pro | Val | Thr | Gln | Met | |
| | | 50 | | | | | 55 | | | | | 60 | | | | |
| TAC | ACT | AAT | GTG | GAC | CAG | GAC | CTC | GTC | GGC | TGG | CCG | GCG | CCC | TCC | GGG | 239 |
| Tyr | Thr | Asn | Val | Asp | Gln | Asp | Leu | Val | Gly | Trp | Pro | Ala | Pro | Ser | Gly | |
| | | 65 | | | | | 70 | | | | | 75 | | | | |
| GCG | CGG | TCC | TTG | ACA | CCA | TGC | ACC | TGC | GGC | AGC | TCG | GAC | CTT | TAC | TTG | 287 |
| Ala | Arg | Ser | Leu | Thr | Pro | Cys | Thr | Cys | Gly | Ser | Ser | Asp | Leu | Tyr | Leu | |
| 80 | | | | | 85 | | | | | 90 | | | | | 95 | |
| GTC | ACG | AGG | CAT | GCT | GAT | GTC | ATT | CCG | GTG | CGC | CGG | CGG | GGC | GAT | AGC | 335 |
| Val | Thr | Arg | His | Ala | Asp | Val | Ile | Pro | Val | Arg | Arg | Arg | Gly | Asp | Ser | |
| | | | 100 | | | | | 105 | | | | | 110 | | | |
| AGG | GGG | AGC | CTG | CTT | TCC | CCC | AGG | CCC | CTC | TCC | TAC | TTG | AAG | GGC | TCC | 383 |
| Arg | Gly | Ser | Leu | Leu | Ser | Pro | Arg | Pro | Leu | Ser | Tyr | Leu | Lys | Gly | Ser | |
| | | | 115 | | | | | 120 | | | | | 125 | | | |
| TCA | GGT | GGT | CCA | CTG | CTT | TGC | CCC | TCG | GGG | CAC | ATT | GTG | GGC | ATC | TTC | 431 |
| Ser | Gly | Gly | Pro | Leu | Leu | Cys | Pro | Ser | Gly | His | Ile | Val | Gly | Ile | Phe | |
| | | 130 | | | | | 135 | | | | | 140 | | | | |
| CGG | GCT | GCC | GTG | TGC | ACC | CGG | GGG | GTT | GCG | AAG | GCG | GTG | GAC | TTT | GTA | 479 |
| Arg | Ala | Ala | Val | Cys | Thr | Arg | Gly | Val | Ala | Lys | Ala | Val | Asp | Phe | Val | |
| | 145 | | | | 150 | | | | | 155 | | | | | | |
| CCT | GTC | GAG | TCT | ATG | GAA | ACT | ACT | ATG | CGG | TCT | CCG | GTC | TTC | ACG | GAT | 527 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     | Pro 160 | Val | Glu | Ser | Met | Glu 165 | Thr | Thr | Met | Arg | Ser 170 | Pro | Val | Phe | Thr | Asp 175 |
| AAT | TCA | TCC | CCC | CCG | GCC | GTA | CCG | CAG | ACA | TTC | CAA | GTG | GCC | CAT | CTG | 575 |
| Asn | Ser | Ser | Pro 180 | Pro | Ala | Val | Pro | Gln 185 | Thr | Phe | Gln | Val | Ala 190 | His | Leu |     |
| CAT | GCC | CCC | ACT | GGC | AGC | GGC | AAG | AGC | ACT | AAG | GTG | CCG | GCT | GCA | TAC | 623 |
| His | Ala | Pro | Thr 195 | Gly | Ser | Gly | Lys | Ser 200 | Thr | Lys | Val | Pro | Ala 205 | Ala | Tyr |     |
| GCA | GCC | CAG | GGA | TAC | AAG | GTA | CTC | GTC | CTG | AAC | CCG | TCC | GTT | GCC | GCC | 671 |
| Ala | Ala | Gln 210 | Gly | Tyr | Lys | Val | Leu 215 | Val | Leu | Asn | Pro | Ser 220 | Val | Ala | Ala |     |
| ACC | TTA | GGT | TTT | GGA | GCA | TAT | ATG | TCC | AAG | GCA | CAT | GGT | GTC | GAC | CCT | 719 |
| Thr | Leu 225 | Gly | Phe | Gly | Ala | Tyr 230 | Met | Ser | Lys | Ala | His 235 | Gly | Val | Asp | Pro |     |
| AAC | ATC | AGG | ACT | GGG | GTA | AGG | ACC | ATC | ACT | ACG | GGC | GCC | CCC | ATT | ACA | 767 |
| Asn 240 | Ile | Arg | Thr | Gly | Val 245 | Arg | Thr | Ile | Thr | Thr 250 | Gly | Ala | Pro | Ile | Thr 255 |     |
| TAC | TCC | ACC | TAT | GGC | AAG | TTT | CTT | GCC | GAC | GGT | GGT | TGC | TCC | GGG | GGC | 815 |
| Tyr | Ser | Thr | Tyr | Gly 260 | Lys | Phe | Leu | Ala | Asp 265 | Gly | Gly | Cys | Ser | Gly 270 | Gly |     |
| GCC | TAT | GAC | ATC | ATA | ATA | TGT | GAT | GAG | TGC | CAC | TCA | ACT | GAC | TCG | ACT | 863 |
| Ala | Tyr | Asp | Ile 275 | Ile | Ile | Cys | Asp | Glu 280 | Cys | His | Ser | Thr | Asp 285 | Ser | Thr |     |
| TCC | ATT | TTG | GGC | ATT | GGC | ACG | GTC | CTG | GAC | CAA | GCG | GAG | ACG | GCT | GGA | 911 |
| Ser | Ile | Leu 290 | Gly | Ile | Gly | Thr | Val 295 | Leu | Asp | Gln | Ala | Glu 300 | Thr | Ala | Gly |     |
| GCG | CGG | CTC | GTC | GTG | CTC | GCC | ACC | GCT | ACG | CCT | CCA | GGA | TCG | GTC | ACT | 959 |
| Ala | Arg 305 | Leu | Val | Val | Leu | Ala 310 | Thr | Ala | Thr | Pro | Pro 315 | Gly | Ser | Val | Thr |     |
| GTG | CCT | CAT | CCC | AAC | ATC | GAG | GAG | GTG | GCC | TTG | TCC | AGC | ACT | GGA | GAG | 1007 |
| Val 320 | Pro | His | Pro | Asn | Ile 325 | Glu | Glu | Val | Ala | Leu 330 | Ser | Ser | Thr | Gly | Glu 335 |     |
| ATT | CCC | TTC | TAT | GGC | AAA | GCC | ATC | CCC | ATT | GAG | ACC | ATC | AAG | GGG | GGA | 1055 |
| Ile | Pro | Phe | Tyr | Gly 340 | Lys | Ala | Ile | Pro | Ile 345 | Glu | Thr | Ile | Lys | Gly 350 | Gly |     |
| AGG | CAT | CTC | ATT | TTC | TGC | CAC |     |     |     |     |     |     |     |     |     | 1076 |
| Arg | His | Leu | Ile 355 | Phe | Cys | His |     |     |     |     |     |     |     |     |     |     |

( 2 ) INFORMATION FOR SEQ ID NO:11:

( i ) SEQUENCE CHARACTERISTICS:
        ( A ) LENGTH:284 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:11:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| GTC | GAC | CCC | AAT | ATT | AGA | ACT | GGG | GTA | AGG | ACC | ATC | ACC | ACG | GGC | GCT | 48 |
| Val 1 | Asp | Pro | Asn | Ile 5 | Arg | Thr | Gly | Val | Arg 10 | Thr | Ile | Thr | Thr | Gly 15 | Ala |     |
| CCC | ATT | ACG | TAT | TCT | ACC | TAT | GGC | AAA | TTC | CTT | GCC | GAC | GGT | GGT | TGC | 96 |
| Pro | Ile | Thr | Tyr 20 | Ser | Thr | Tyr | Gly | Lys 25 | Phe | Leu | Ala | Asp | Gly 30 | Gly | Cys |     |
| TCT | GGG | GGC | GCC | TAT | GAC | ATC | ATA | ATC | TGT | GAT | GAG | TGC | CAC | TCA | ACT | 144 |
| Ser | Gly | Gly 35 | Ala | Tyr | Asp | Ile | Ile 40 | Ile | Cys | Asp | Glu | Cys 45 | His | Ser | Thr |     |
| GAC | TCG | ACT | TCC | ATC | TTG | GGT | ATC | GGC | ACA | GCC | CTG | GAC | CAA | GCG | GAG | 192 |
| Asp | Ser 50 | Thr | Ser | Ile | Leu | Gly 55 | Ile | Gly | Thr | Ala | Leu 60 | Asp | Gln | Ala | Glu |     |

```
ACG GCT GGA GCA CGG CTT GTC GTG CTC GCC ACC GCT ACG CCT CCA GGG      240
Thr Ala Gly Ala Arg Leu Val Val Leu Ala Thr Ala Thr Pro Pro Gly
65                  70                  75                  80

TCG GTC ACC GTG CCG CAT CCC AAC ATC GAG GAG GTA GCC TTG CC           284
Ser Val Thr Val Pro His Pro Asn Ile Glu Glu Val Ala Leu
                    85                  90
```

( 2 ) INFORMATION FOR SEQ ID NO:12:

( i ) SEQUENCE CHARACTERISTICS:
        ( A ) LENGTH:641 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:12:

```
G GAC AAC TCA TCT CCC CCG GCG GTA CCG CAG ACA TTC CAG GTG GCC CAT    49
  Asp Asn Ser Ser Pro Pro Ala Val Pro Gln Thr Phe Gln Val Ala His
  1               5                   10                  15

CTA CAC GCT CCC ACT GGC AGC GGC AAG AGC ACT AAG GTG CCG GCT GCA      97
Leu His Ala Pro Thr Gly Ser Gly Lys Ser Thr Lys Val Pro Ala Ala
                20                  25                  30

TAT GCA GCC CAA GGG TAC AAA GTA CTC GTC CTG AAC CCG TCC GTT GCC      145
Tyr Ala Ala Gln Gly Tyr Lys Val Leu Val Leu Asn Pro Ser Val Ala
                35                  40                  45

GCC ACC TTA AGT TTC GGG GCG TAT ATG TCC AAG GCA CAT GGT GTT GAC      193
Ala Thr Leu Ser Phe Gly Ala Tyr Met Ser Lys Ala His Gly Val Asp
        50                  55                  60

CCT AAT ATC AGA ACT GGG ACA AGG ACC ATC ACC ACG GGC GCT CCC ATC      241
Pro Asn Ile Arg Thr Gly Thr Arg Thr Ile Thr Thr Gly Ala Pro Ile
65                  70                  75                  80

ACG TAC TCC ACC TAT GGC AAG TTC CTT GCA GAC GGT GGT TGC TCC GGA      289
Thr Tyr Ser Thr Tyr Gly Lys Phe Leu Ala Asp Gly Gly Cys Ser Gly
                85                  90                  95

GGC GCC TAT GAC ATC ATA ATA TGC GAT GAG TGC CAC TCA ACA GAC TCG      337
Gly Ala Tyr Asp Ile Ile Ile Cys Asp Glu Cys His Ser Thr Asp Ser
                100                 105                 110

ACT TCC ATC TTA GGC ATT GGT ACG GTC CTG GAC CAA GCG GAG ACG GCT      385
Thr Ser Ile Leu Gly Ile Gly Thr Val Leu Asp Gln Ala Glu Thr Ala
            115                 120                 125

GGA GCG CGA CTC GTC GTG CTC GCC ACC GCT ACG CCT CCA GGA TCG GTC      433
Gly Ala Arg Leu Val Val Leu Ala Thr Ala Thr Pro Pro Gly Ser Val
        130                 135                 140

ACT GTG CCA CAT CCC AAC ATC GAG GAG GTG GCC CTG TCC AAC ACT GGA      481
Thr Val Pro His Pro Asn Ile Glu Glu Val Ala Leu Ser Asn Thr Gly
145                 150                 155                 160

GAG ATT CCC TTC TAT GGC AAA GCC ATC CCC ATT GAG GCC ATC AAG GGG      529
Glu Ile Pro Phe Tyr Gly Lys Ala Ile Pro Ile Glu Ala Ile Lys Gly
                165                 170                 175

GGG AGG CAT CTC ATT TTC TGC CAT TCT AAG AAG AAG TGT GAT GAG CTC      577
Gly Arg His Leu Ile Phe Cys His Ser Lys Lys Lys Cys Asp Glu Leu
                180                 185                 190

GCC ACG AAG CTG TCG GCC CTC GGA CTC AAT GCT GTA GCG TAC TAC CGG      625
Ala Thr Lys Leu Ser Ala Leu Gly Leu Asn Ala Val Ala Tyr Tyr Arg
            195                 200                 205

GGT CTT GAT GTG TCC G                                                641
Gly Leu Asp Val Ser
210
```

( 2 ) INFORMATION FOR SEQ ID NO:13:

( i ) SEQUENCE CHARACTERISTICS:
   ( A ) LENGTH: 432 base pairs
   ( B ) TYPE: nucleic acid
   ( C ) STRANDEDNESS: double
   ( D ) TOPOLOGY: linear ( i i ) MOLECULE TYPE: cDNA to genomic RNA ( x i ) SEQUENCE DESCRIPTION: SEQ ID NO:13:

```
CA  GGC  GAG  AGG  CCG  ACA  GGG  ATG  TTT  GAC  AGC  GTA  GTG  CTC  TGT  GAG        47
    Gly  Glu  Arg  Pro  Thr  Gly  Met  Phe  Asp  Ser  Val  Val  Leu  Cys  Glu
     1              5                        10                         15

TGC  TAT  GAT  GCC  GGG  GCC  GCC  TGG  TAC  GAG  CTT  ACG  CCT  GCT  GAG  ACT        95
Cys  Tyr  Asp  Ala  Gly  Ala  Ala  Trp  Tyr  Glu  Leu  Thr  Pro  Ala  Glu  Thr
                    20                   25                        30

ACG  GTG  AGA  CTC  CGG  GCT  TAT  TTC  AAC  ACG  CCC  GGT  TTG  CCT  GTA  TGT       143
Thr  Val  Arg  Leu  Arg  Ala  Tyr  Phe  Asn  Thr  Pro  Gly  Leu  Pro  Val  Cys
               35                        40                   45

CAA  GAC  CAC  CTA  GAG  TTC  TGG  GAA  GCG  GTC  TTC  ACA  GGT  CTC  ACA  CAC       191
Gln  Asp  His  Leu  Glu  Phe  Trp  Glu  Ala  Val  Phe  Thr  Gly  Leu  Thr  His
          50                        55                        60

ATT  GAT  GCC  CAC  TTC  CTC  TCC  CAG  ACG  AAG  CAA  GGA  GGA  GAC  AAC  TTT       239
Ile  Asp  Ala  His  Phe  Leu  Ser  Gln  Thr  Lys  Gln  Gly  Gly  Asp  Asn  Phe
     65                        70                        75

GCG  TAT  CTA  ACG  GCC  TAC  CAG  GCC  ACA  GTA  TGC  GCC  AGG  GCA  AAG  GCC       287
Ala  Tyr  Leu  Thr  Ala  Tyr  Gln  Ala  Thr  Val  Cys  Ala  Arg  Ala  Lys  Ala
 80                        85                        90                         95

CCC  CCT  CCT  TCG  TGG  GAC  GTG  ATG  TGG  AAG  TGT  CTA  ATC  AGG  CTC  AAA       335
Pro  Pro  Pro  Ser  Trp  Asp  Val  Met  Trp  Lys  Cys  Leu  Ile  Arg  Leu  Lys
                    100                       105                       110

CCT  ACA  TTG  ACT  GGT  CCT  ACC  CCC  CTC  CTG  TAC  CGC  TTG  GGT  GCC  GTG       383
Pro  Thr  Leu  Thr  Gly  Pro  Thr  Pro  Leu  Leu  Tyr  Arg  Leu  Gly  Ala  Val
               115                       120                       125

ACT  AAC  GAG  GTT  ACC  CTG  ACG  CAC  CCC  GTG  ACG  AAA  TAT  ATC  GCC  ACG  T    432
Thr  Asn  Glu  Val  Thr  Leu  Thr  His  Pro  Val  Thr  Lys  Tyr  Ile  Ala  Thr
          130                       135                       140
```

( 2 ) INFORMATION FOR SEQ ID NO:14:

( i ) SEQUENCE CHARACTERISTICS:
      ( A ) LENGTH: 369 base pairs
      ( B ) TYPE: nucleic acid
      ( C ) STRANDEDNESS: double
      ( D ) TOPOLOGY: linear ( i i ) MOLECULE TYPE: cDNA to genomic RNA ( x i ) SEQUENCE DESCRIPTION: SEQ ID NO:14:

```
ATG  GGC  ACG  AAT  CCT  AAA  CCT  CAA  AGA  AAA  ACC  AAA  AGA  AAC  ACT  AAC        48
Met  Gly  Thr  Asn  Pro  Lys  Pro  Gln  Arg  Lys  Thr  Lys  Arg  Asn  Thr  Asn
 1              5                        10                        15

CGT  CGC  CCA  CAA  GAC  GTT  AAG  TTT  CCG  GGC  GGC  GGC  CAG  ATC  GTT  GGC        96
Arg  Arg  Pro  Gln  Asp  Val  Lys  Phe  Pro  Gly  Gly  Gly  Gln  Ile  Val  Gly
               20                        25                        30

GGA  GTA  TAC  TTG  TTG  CCG  CGC  AGG  GGC  CCC  AGA  TTG  GGT  GTG  CGC  GCG       144
Gly  Val  Tyr  Leu  Leu  Pro  Arg  Arg  Gly  Pro  Arg  Leu  Gly  Val  Arg  Ala
               35                        40                        45

ACA  AGG  AAG  ACT  TCG  AAG  CGG  TCC  CAG  CCA  CGT  GGG  GGG  CGC  CGG  CCC       192
Thr  Arg  Lys  Thr  Ser  Lys  Arg  Ser  Gln  Pro  Arg  Gly  Gly  Arg  Arg  Pro
          50                        55                        60

ATC  CCT  AAA  GAT  CGG  CGC  TCC  ACT  GGC  AAG  TCC  TGG  GGG  AAA  CCA  GGA       240
Ile  Pro  Lys  Asp  Arg  Arg  Ser  Thr  Gly  Lys  Ser  Trp  Gly  Lys  Pro  Gly
 65                        70                        75                         80
```

```
TAC CCC TGG CCC CTA TAT GGG AAT GAG GGA CTC GGC TGG GCA GGG TGG    288
Tyr Pro Trp Pro Leu Tyr Gly Asn Glu Gly Leu Gly Trp Ala Gly Trp
            85                  90                  95

CTT CTG TCC CCC CGA GGT TCC CGT CCC TCT TGG GGC CCC ACT GAC CCC    336
Leu Leu Ser Pro Arg Gly Ser Arg Pro Ser Trp Gly Pro Thr Asp Pro
            100                 105                 110

CGG CAT AGG TCG CGC AAT GTG GGT AAG GTC ATC                        369
Arg His Arg Ser Arg Asn Val Gly Lys Val Ile
        115                 120
```

( 2 ) INFORMATION FOR SEQ ID NO:15:

( i ) SEQUENCE CHARACTERISTICS:
        ( A ) LENGTH:932 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:15:

```
CG CGC AAC TTG GGT AAG GTC ATC GAT ACC CTC ACA TGC GGC TTC GCC      47
   Arg Asn Leu Gly Lys Val Ile Asp Thr Leu Thr Cys Gly Phe Ala
   1               5                   10                  15

GAC CTC ATG GGG TAC ATT CCG CTT GTC GGC GCC CCC CTA GGG GGT GCT     95
Asp Leu Met Gly Tyr Ile Pro Leu Val Gly Ala Pro Leu Gly Gly Ala
            20                  25                  30

GCC AGG GCC CTG GCA CAT GGT GTC CGG GTT CTG GAG GAC GGC GTG AAC    143
Ala Arg Ala Leu Ala His Gly Val Arg Val Leu Glu Asp Gly Val Asn
            35                  40                  45

TAT GCA ACA GGG AAT TTG CCC GGT TGC TCT TTC TCT ATC TTC CTC TTG    191
Tyr Ala Thr Gly Asn Leu Pro Gly Cys Ser Phe Ser Ile Phe Leu Leu
            50                  55                  60

GCT TTG CTG TCC TGT TTG ACC ATC CCA GCT TCC GCT TAT GAG GTG CGC    239
Ala Leu Leu Ser Cys Leu Thr Ile Pro Ala Ser Ala Tyr Glu Val Arg
        65                  70                  75

AAC GTA TCC GGG ATA TAC CAT GTC ACG AAC GAC TGC TCC AAC TCA AGT    287
Asn Val Ser Gly Ile Tyr His Val Thr Asn Asp Cys Ser Asn Ser Ser
80                  85                  90                  95

ATT GTG TAT GAG GCA GCG GAC ATG ATC ATG CAT ACC CCC GGG TGC GTG    335
Ile Val Tyr Glu Ala Ala Asp Met Ile Met His Thr Pro Gly Cys Val
            100                 105                 110

CCC TGC GTT CGG GAG AAC AAC TCC TCC CGT TGC TGG GCA GCG CTC ACT    383
Pro Cys Val Arg Glu Asn Asn Ser Ser Arg Cys Trp Ala Ala Leu Thr
            115                 120                 125

CCC ACG TTA GCG GCC AGG AAC ACC AGC GTC CCC ACT ACG ACA ATA CGA    431
Pro Thr Leu Ala Ala Arg Asn Thr Ser Val Pro Thr Thr Thr Ile Arg
            130                 135                 140

CGG CAT GTC GAT TTG CTC GTT GGG GCG GCT GCT TTC TGC TCC GCT ATG    479
Arg His Val Asp Leu Leu Val Gly Ala Ala Ala Phe Cys Ser Ala Met
            145                 150                 155

TAC GTG GGG GAT CTC TGT GGA TCT GTC TTC CTC GTT TCC CAG CTG TTC    527
Tyr Val Gly Asp Leu Cys Gly Ser Val Phe Leu Val Ser Gln Leu Phe
160                 165                 170                 175

ACT TTC TCA CCT CGT CGG CAT GAG ACA GTA CAG GAC TGC AAC TGC TCA    575
Thr Phe Ser Pro Arg Arg His Glu Thr Val Gln Asp Cys Asn Cys Ser
            180                 185                 190

ATC TAT CCC GGC CAC TTG ACA GGT CAT CGC ATG GCT TGG GAT ATG ATG    623
Ile Tyr Pro Gly His Leu Thr Gly His Arg Met Ala Trp Asp Met Met
            195                 200                 205

ATG AAC TGG TCA CCT ACA ACA GCC CTA GTG GTG TCG CAT CTA CTC CGG    671
```

```
Met Asn Trp Ser Pro Thr Thr Ala Leu Val Val Ser His Leu Leu Arg
    210             215                 220

ATC CCA CAA GCT GTC ATG GAC ATG GTG GCG GGG GCT CAC TGG GGA GTC    719
Ile Pro Gln Ala Val Met Asp Met Val Ala Gly Ala His Trp Gly Val
    225             230                 235

CTA GCG GGC CTC GCC TAC TAT TCC ATG GTG GGG AAC TGG GCT AAG GTT    767
Leu Ala Gly Leu Ala Tyr Tyr Ser Met Val Gly Asn Trp Ala Lys Val
240             245                 250                 255

TTG ATT GTG ATG CTA CTC TTC GCC GGC GTT GAC GGG ACC ACC TAT GTG    815
Leu Ile Val Met Leu Leu Phe Ala Gly Val Asp Gly Thr Thr Tyr Val
                260                 265                 270

ACA GGG GGG ACG ACA GGC CGC ACC ACC AGC TCG TTC GCA TCC CTC TTT    863
Thr Gly Gly Thr Thr Gly Arg Thr Thr Ser Ser Phe Ala Ser Leu Phe
                275             280                 285

ACA CTT GGG TCG CAT CAG AAG GTC CAG CTT ATA AAT ACC AAT GGC AGC    911
Thr Leu Gly Ser His Gln Lys Val Gln Leu Ile Asn Thr Asn Gly Ser
        290                 295                 300

TGG CAC ATC AAC AGG ACC GCC                                        932
Trp His Ile Asn Arg Thr Ala
    305             310
```

( 2 ) INFORMATION FOR SEQ ID NO:16:

( i ) SEQUENCE CHARACTERISTICS:
        ( A ) LENGTH:559 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:16:

```
CGC CGG TAT GAG ACG GCG CAA GAC TGC AAT TGC TCA CTC TAT CCC GGT     48
Arg Arg Tyr Glu Thr Ala Gln Asp Cys Asn Cys Ser Leu Tyr Pro Gly
1               5                   10                  15

CAC GTA TCT GGT CAC CGC ATG GCT TGG GAT ATG ATG ATG AAC TGG TCA     96
His Val Ser Gly His Arg Met Ala Trp Asp Met Met Met Asn Trp Ser
            20                  25                  30

CCT ACA ACG GCC CTA GTG GTA TCG CAG CTA CTC CGG ATC CCA CAA GCC    144
Pro Thr Thr Ala Leu Val Val Ser Gln Leu Leu Arg Ile Pro Gln Ala
        35                  40                  45

GTC GTG GAC ATG GTG GCG GGG GCC CAC TGG GGA GTC CTA GCG GGC CTT    192
Val Val Asp Met Val Ala Gly Ala His Trp Gly Val Leu Ala Gly Leu
    50                  55                  60

GCC TAC TAT TCC ATG GTG GCG AAC TGG GCT AAG GTC TTG GTT GTG ATG    240
Ala Tyr Tyr Ser Met Val Ala Asn Trp Ala Lys Val Leu Val Val Met
Met
65                  70                  75                  80

CTA CTC TTT GCC GGC GTT GAC GAC GGG AAG ACC ACC GTG ACG GGG GGG    288
Leu Leu Phe Ala Gly Val Asp Asp Gly Lys Thr Thr Val Thr Gly Gly
                85                  90                  95

AGC GCA GCC TTC CAG TCC AGG AAG TTA GTG TCC TTC TTC TCA CCA GGG    336
Ser Ala Ala Phe Gln Ser Arg Lys Leu Val Ser Phe Phe Ser Pro Gly
            100                 105                 110

CCG AAA CAA AAT ATC CAG CTT GAT AAC ACC AAC GGC AGC TGG CAC ATC    384
Pro Lys Gln Asn Ile Gln Leu Asp Asn Thr Asn Gly Ser Trp His Ile
        115                 120                 125

AAC AGG ACT GCC CTG AAT TGC AAT GAC TCC CTC CAA ACT GGG TTC ATC    432
Asn Arg Thr Ala Leu Asn Cys Asn Asp Ser Leu Gln Thr Gly Phe Ile
    130                 135                 140

GCT GCG CTG TTC TAC GCG CAC AAG TTC AAT TCG TCC GGA TGC CTA GAG    480
Ala Ala Leu Phe Tyr Ala His Lys Phe Asn Ser Ser Gly Cys Leu Glu
```

```
145                  150                   155                   160
CGC  ATG  GCC  AGC  TGC  CGC  CCC  ATT  GAC  AAG  TTC  GCG  CAG  GGG  TGG  GGT    528
Arg  Met  Ala  Ser  Cys  Arg  Pro  Ile  Asp  Lys  Phe  Ala  Gln  Gly  Trp  Gly
                    165                  170                       175

CCC  ATC  ACT  CAC  GAT  ACG  CCT  AAG  ATC  CCG  G                              559
Pro  Ile  Thr  His  Asp  Thr  Pro  Lys  Ile  Pro
               180                  185
```

( 2 ) INFORMATION FOR SEQ ID NO:17:

( i ) SEQUENCE CHARACTERISTICS:
        ( A ) LENGTH:276 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:17:

```
GA  CAC  CGT  ATG  GCA  TGG  GAC  ATG  ATG  ATG  AAC  TGG  TCG  CCC  ACG  GCT    47
    His  Arg  Met  Ala  Trp  Asp  Met  Met  Met  Asn  Trp  Ser  Pro  Thr  Ala
    1              5                        10                       15

ACC  ATG  ATT  CTG  GCG  TAT  GTG  ATG  CGC  ATC  CCC  GAG  GTC  GTC  ATG  GAC    95
Thr  Met  Ile  Leu  Ala  Tyr  Val  Met  Arg  Ile  Pro  Glu  Val  Val  Met  Asp
               20                       25                       30

ATC  ATT  GGC  GGG  GCT  CAC  TGG  GGC  GTC  ATG  TTC  GGC  TTG  GGC  TAT  TTT   143
Ile  Ile  Gly  Gly  Ala  His  Trp  Gly  Val  Met  Phe  Gly  Leu  Gly  Tyr  Phe
               35                       40                       45

TCT  ATG  CAG  GGG  GCT  TGG  GCA  AAA  GTC  GTT  GTC  ATC  CTT  CTG  CTG  GCC   191
Ser  Met  Gln  Gly  Ala  Trp  Ala  Lys  Val  Val  Val  Ile  Leu  Leu  Leu  Ala
               50                       55                       60

GCT  GGG  GTG  GAT  GCG  ACT  ACC  CTC  AGC  GTT  GGG  GGC  TCT  GCC  GCG  CAC   239
Ala  Gly  Val  Asp  Ala  Thr  Thr  Leu  Ser  Val  Gly  Gly  Ser  Ala  Ala  His
          65                       70                       75

ACC  ACC  GGC  GGC  CTT  GTC  GGC  TTG  TTC  AAG  CCT  GGC  G                    276
Thr  Thr  Gly  Gly  Leu  Val  Gly  Leu  Phe  Lys  Pro  Gly
80                       85                       90
```

( 2 ) INFORMATION FOR SEQ ID NO:18:

( i ) SEQUENCE CHARACTERISTICS:
        ( A ) LENGTH:742 base pairs
        ( B ) TYPE:nucleic acid
        ( C ) STRANDEDNESS:double
        ( D ) TOPOLOGY:linear ( i i ) MOLECULE TYPE:cDNA to genomic RNA ( x i ) SEQUENCE DESCRIPTION: SEQ ID NO:18:

```
CG  CTT  GTC  GGC  GCC  CCC  CTA  GGG  GGT  GCT  GCC  AGG  GCC  CTG  GCA  CAT    47
    Leu  Val  Gly  Ala  Pro  Leu  Gly  Gly  Ala  Ala  Arg  Ala  Leu  Ala  His
    1              5                        10                       15

GGT  GTC  CGG  GTT  CTG  GAG  GAC  GGC  GTG  AAC  TAT  GCA  ACA  GGG  AAT  TTG    95
Gly  Val  Arg  Val  Leu  Glu  Asp  Gly  Val  Asn  Tyr  Ala  Thr  Gly  Asn  Leu
               20                       25                       30

CCC  GGT  TGC  TCT  TTC  TCT  ATC  TTC  CTC  TTG  GCT  TTG  CTG  TCC  TGT  TTG   143
Pro  Gly  Cys  Ser  Phe  Ser  Ile  Phe  Leu  Leu  Ala  Leu  Leu  Ser  Cys  Leu
               35                       40                       45

ACC  ATC  CCA  GCT  TCC  GCT  TAT  GAG  GTG  CGC  AAC  GTA  TCC  GGG  ATA  TAC   191
Thr  Ile  Pro  Ala  Ser  Ala  Tyr  Glu  Val  Arg  Asn  Val  Ser  Gly  Ile  Tyr
               50                       55                       60

CAT  GTC  ACG  AAC  GAC  TGC  TCC  AAC  TCA  AGT  ATT  GTG  TAT  GAG  GCA  GCG   239
His  Val  Thr  Asn  Asp  Cys  Ser  Asn  Ser  Ser  Ile  Val  Tyr  Glu  Ala  Ala
```

```
                    65                          70                          75
GAC  ATG  ATC  ATG  CAT  ACC  CCC  GGG  TGC  GTG  CCC  TGC  GTT  CGG  GAG  AAC    287
Asp  Met  Ile  Met  His  Thr  Pro  Gly  Cys  Val  Pro  Cys  Val  Arg  Glu  Asn
 80                      85                        90                        95

AAC  TCC  TCC  CGT  TGC  TGG  GCA  GCG  CTC  ACT  CCC  ACG  TTA  GCG  GCC  AGG    335
Asn  Ser  Ser  Arg  Cys  Trp  Ala  Ala  Leu  Thr  Pro  Thr  Leu  Ala  Ala  Arg
                    100                      105                      110

AAC  ACC  AGC  GTC  CCC  ACT  ACG  ACA  ATA  CGA  CGG  CAT  GTC  GAT  TTG  CTC    383
Asn  Thr  Ser  Val  Pro  Thr  Thr  Thr  Ile  Arg  Arg  His  Val  Asp  Leu
Leu
               115                           120                       125

GTT  GGG  GCG  GCT  GCT  TTC  TGC  TCC  GCT  ATG  TAC  GTG  GGG  GAT  CTC  TGT    431
Val  Gly  Ala  Ala  Ala  Phe  Cys  Ser  Ala  Met  Tyr  Val  Gly  Asp  Leu  Cys
               130                      135                      140

GGA  TCT  GTC  TTC  CTC  GTT  TCC  CAG  CTG  TTC  ACT  TTC  TCA  CCT  CGT  CGG    479
Gly  Ser  Val  Phe  Leu  Val  Ser  Gln  Leu  Phe  Thr  Phe  Ser  Pro  Arg  Arg
          145                      150                      155

CAT  GAG  ACA  GTA  CAG  GAC  TGC  AAC  TGC  TCA  ATC  TAT  CCC  GGC  CAC  TTG    527
His  Glu  Thr  Val  Gln  Asp  Cys  Asn  Cys  Ser  Ile  Tyr  Pro  Gly  His  Leu
160                      165                      170                      175

ACA  GGT  CAT  CGC  ATG  GCT  TGG  GAT  ATG  ATG  ATG  AAC  TGG  TCA  CCT  ACA    575
Thr  Gly  His  Arg  Met  Ala  Trp  Asp  Met  Met  Met  Asn  Trp  Ser  Pro  Thr
                    180                      185                      190

ACA  GCC  CTA  GTG  GTG  TCG  CAT  CTA  CTC  CGG  ATC  CCA  CAA  GCT  GTC  ATG    623
Thr  Ala  Leu  Val  Val  Ser  His  Leu  Leu  Arg  Ile  Pro  Gln  Ala  Val  Met
                         195                      200                      205

GAC  ATG  GTG  GCG  GGG  GCC  CAC  TGG  GGA  GTC  CTA  GCG  GGC  CTT  GCC  TAC    671
Asp  Met  Val  Ala  Gly  Ala  His  Trp  Gly  Val  Leu  Ala  Gly  Leu  Ala  Tyr
               210                      215                      220

TAT  TCC  ATG  GTG  GGG  AAC  TGG  GCT  AAG  GTT  TTG  ATT  GTG  ATG  CTA  CTC    719
Tyr  Ser  Met  Val  Gly  Asn  Trp  Ala  Lys  Val  Leu  Ile  Val  Met  Leu  Leu
          225                      230                      235

TTC  GCC  GGC  GTT  GAC  GGG  ACC  AC                                             742
Phe  Ala  Gly  Val  Asp  Gly  Thr
240                      245
```

( 2 ) INFORMATION FOR SEQ ID NO:19:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( x i ) SEQUENCE DESCRIPTION: SEQ ID NO:19:

```
GGATACACCG GTGACTTTGA                                                              20
```

( 2 ) INFORMATION FOR SEQ ID NO:20:

( i ) SEQUENCE CHARACTERISTICS:
        ( A ) LENGTH:20 base pairs
        ( B ) TYPE:nucleic acid
        ( C ) STRANDEDNESS:single
        ( D ) TOPOLOGY:linear ( x i ) SEQUENCE DESCRIPTION: SEQ ID NO:20:

```
TGCATGCACG TGGCGATGTA                                                              20
```

( 2 ) INFORMATION FOR SEQ ID NO:21:

( i ) SEQUENCE CHARACTERISTICS:
        ( A ) LENGTH:20 base pairs
        ( B ) TYPE:nucleic acid (C) STRANDEDNESS:single
(D) TOPOLOGY:linear (xi) SEQUENCE DESCRIPTION: SEQ ID NO:21:

GATGCCCACT TCCTCTCCCA 20

(2) INFORMATION FOR SEQ ID NO:22:

(i) SEQUENCE CHARACTERISTICS:
(A) LENGTH:20 base pairs
(B) TYPE:nucleic acid
(C) STRANDEDNESS:single
(D) TOPOLOGY:linear (xi) SEQUENCE DESCRIPTION: SEQ ID NO:22:

GTCAGGGTAA CCTCGTTGGT 20

(2) INFORMATION FOR SEQ ID NO:23:

(i) SEQUENCE CHARACTERISTICS:
(A) LENGTH:25 base pairs
(B) TYPE:nucleic acid
(C) STRANDEDNESS:single
(D) TOPOLOGY:linear (xi) SEQUENCE DESCRIPTION: SEQ ID NO:23:

TTACGAATTC ATGGGCACGA ATCCT 25

(2) INFORMATION FOR SEQ ID NO:24:

(i) SEQUENCE CHARACTERISTICS:
(A) LENGTH:27 base pairs
(B) TYPE:nucleic acid
(C) STRANDEDNESS:single
(D) TOPOLOGY:linear (xi) SEQUENCE DESCRIPTION: SEQ ID NO:24:

TTAATCGATG ACCTTACCCA CATTGCG 27